US009975848B2

(12) United States Patent
Smith, III et al.

(10) Patent No.: US 9,975,848 B2
(45) Date of Patent: May 22, 2018

(54) INHIBITORS OF HIV-1 ENTRY AND METHODS OF USE THEREOF

(71) Applicants: The Trustees of The University of Pennsylvania, Philadelphia, PA (US); Dana-Farber Cancer Institute, Inc., Boston, MA (US); Bryn Mawr College, Bryn Mawr, PA (US)

(72) Inventors: Amos B. Smith, III, Merion, PA (US); Joseph Sodroski, Medford, MA (US); Navid Madani, Newton, MA (US); Bruno Melillo, Philadelphia, PA (US); Judith M. LaLonde, Havertown, PA (US); Amy M. Princiotto, Attleboro, MA (US)

(73) Assignees: The Trustees of the University of Pennsylvania, Philadelphia, PA (US); Dana-Farber Cancer Institute, Inc., Boston, MA (US); Bryn Mawr College, Bryn Mawr, PA (US)

( * ) Notice: Subject to any disclaimer, the term of this patent is extended or adjusted under 35 U.S.C. 154(b) by 0 days. days.

(21) Appl. No.: 15/503,207

(22) PCT Filed: Aug. 13, 2015

(86) PCT No.: PCT/US2015/044998
§ 371 (c)(1),
(2) Date: Feb. 10, 2017

(87) PCT Pub. No.: WO2016/025681
PCT Pub. Date: Feb. 18, 2016

(65) Prior Publication Data
US 2017/0233335 A1 Aug. 17, 2017

Related U.S. Application Data

(60) Provisional application No. 62/036,853, filed on Aug. 13, 2014.

(51) Int. Cl.
*A61K 31/167* (2006.01)
*C07C 279/12* (2006.01)
*C07K 16/10* (2006.01)
*A61K 39/42* (2006.01)
*C07K 14/005* (2006.01)
*C12N 7/00* (2006.01)

(52) U.S. Cl.
CPC .......... *C07C 279/12* (2013.01); *A61K 31/167* (2013.01); *A61K 39/42* (2013.01); *C07K 14/005* (2013.01); *C07K 16/1063* (2013.01); *C12N 7/00* (2013.01); *C07C 2602/08* (2017.05); *C12N 2740/16122* (2013.01)

(58) Field of Classification Search
CPC . C07C 279/12; C07C 2602/08; A61K 31/167; A61K 39/42
See application file for complete search history.

(56) References Cited

U.S. PATENT DOCUMENTS

| | | | |
|---|---|---|---|
| 6,030,772 A | 2/2000 | Devico et al. | |
| 7,811,580 B2 | 10/2010 | Barnett et al. | |
| 9,403,763 B2 | 8/2016 | Sodroski | |
| 2005/0020645 A1 | 1/2005 | Ohta et al. | |
| 2007/0021450 A1 | 1/2007 | Sklarz et al. | |
| 2012/0122834 A1 | 5/2012 | Sodroski et al. | |
| 2014/0350113 A1* | 11/2014 | Sodroski | C07D 233/88 514/578 |
| 2014/0377219 A1 | 12/2014 | Debnath et al. | |
| 2016/0362478 A1 | 12/2016 | Sodroski et al. | |

FOREIGN PATENT DOCUMENTS

| | | |
|---|---|---|
| EP | 1127883 A2 | 8/2001 |
| JP | 2003-300875 A | 10/2003 |
| WO | WO 94/22826 A1 | 10/1994 |
| WO | WO 97/02027 A1 | 1/1997 |
| WO | WO 98/28268 A2 | 7/1998 |
| WO | WO 98/55447 A1 | 12/1998 |
| WO | WO 99/24065 A1 | 5/1999 |
| WO | WO 03/000657 A1 | 1/2003 |
| WO | WO 2004/082687 A1 | 9/2004 |
| WO | WO 2005/032490 A2 | 4/2005 |
| WO | WO 2006/020070 A2 | 2/2006 |
| WO | WO 2006/106963 A1 | 10/2006 |
| WO | WO 2010/053583 A2 | 5/2010 |
| WO | WO 2011/109237 A2 | 9/2011 |
| WO | WO 2013/090696 A1 | 6/2013 |

(Continued)

OTHER PUBLICATIONS

"HIV-1 gp120 Monoclonal Antibody (48d) Data Sheet", https://www.aidsreagent.org/pdfs/ds1756_.32.pdf, accessed Aug. 6, 2015, 1-2.
Andreadis et al., "Toward a More Accurate Quantitation of the Activity of Recombinant Retroviruses: Alternatives to Titer and Multiplicity of Infection", J. Virol., Feb. 2000, 74, 3431-3439.
Babcock et al., "Ligand Binding Characteristics of CXCR4 Incorporated into Paramagnetic Proteoliposomes", J. Biol. Chem., Oct. 2001, 276, 38433-38440.
Chan et al., "Evidence that a prominent cavity in the coiled coil of HIV type 1 gp41 is an attractive drug target", Proc. Natl. Sci., Dec. 1998, 95, 15613-15617.
Chan et al., "HIV entry and Its Inhibition", Cell, May 1998, 93, 681-684.
Chen et al., "Structure-based identification of small molecule compounds targeting cell cyclophilin A with anti-HIV-1 activity", European Journal of Pharmacology, 2007, vol. 565(1-3), 54-59.

(Continued)

Primary Examiner — Pancham Bakshi
(74) Attorney, Agent, or Firm — Baker & Hostetler LLP

(57) ABSTRACT

The disclosure provides compositions and methods for sensitizing primary HIV-1, including transmitted/founder viruses, to neutralization by monoclonal antibodies, e.g., those directed against CD4-

(56) References Cited

FOREIGN PATENT DOCUMENTS

| WO | WO 2015/120440 A2 | 8/2015 |
|---|---|---|
| WO | WO 2016/025681 A1 | 2/2016 |

OTHER PUBLICATIONS

Cheng et al., "Pharmaceutical applications of dendrimers: promising nanocarriers for drug delivery", Front. Biosci., Jan. 1, 2008, 13, 1447-1471.
Choe et al., "Tyrosine Sulfation of Human Antibodies Contributes to Recognition of the CCR5 Binding Region of HIV-1 gp120", Cell, Jul. 2003, 114, 161-170.
Clapham et al., "Human Immunodeficiency Virus Type 2 Infection and Fusion of CD4-Negative Human Cell Lines: Induction and Enhancement by Soluble CD4", J. Virol., Jun. 1992, 66, 3531-3537.
Courter, et al., "Structure-Based Design, Synthesis and Validations of CD4-Mimetic Small Molecule Inhibitors of HIV-1 Entry: Conversion of a Viral Entry Agonist to an Antagonist", Accounts of Chemical Research, Feb. 6, 2014, 47: 1228-1237.
Dey et al., "Elicitation of Neutralizing Antibodies Directed Against CD4-Induced Epitope(s) Using a CD4 Mimetic Cross-Linked to a HIV-1 Envelope Glycoprotein", PLos One, Jan. 24, 2012, vol. 7, No. 1, 1-13.
Dimitrov et al., "Quantitation of Human Immunodeficiency Virus Type 1 Infection Kinetics", J. Virol., Apr. 1993, 67, 2182-2190.
Donzella et al., "AMD3100, a small molecule inhibitor of HIV-1 entry via the CXCR4 co-receptor", Nat. Med., Jan. 1998, 4, 1, 72-77.
Dragic et al., "A binding pocket for a small molecule inhibitor of HIV-1 entry within the transmembrane helices of CCR5", Proc. Natl. Acad. Sci., May 9, 2000, 97(10), 5639-5644.
Dragic et al., "HIV-1 entry into CD4+ cells is mediated by the chemokine receptor CC-CKR-5", Nature, Jun. 1996, 381, 667-673.
Feng et al., "HIV-1 Entry Cofactor: Functional cDNA Cloning of a Seven-Transmembrane, G Protein-Coupled Receptor", Science, May 1996, 272, 872-877.
Fisher et al., "HIV infection is blocked in vitro by recombinant soluble CD4", Nature, Jan. 1988, 331, 76-78.
Friesner et al., "Glide: A New Approach for Rapid, Accurate Docking and Scoring. 1. Method and Assessment of Docking Accuracy", J. Med. Chem., Mar. 2004, 47, 1739-1749.
Haim et al., "Soluble CD4 and CD4-Mimetic Compounds Inhibit HIV-1 Infection by Induction of a Short-Lived Activated State", PLoS Pathogens, Apr. 2009, 5, e1000360, 13 pages.
Haim et al., "Synchronized Infection of Cell Cultures by Magnetically Controlled Virus", J. Virol., Jan. 2005, 79, 622-625.
Haim et al., "Time Frames for Neutralization during the Human Immunodeficiency Virus Type 1 Entry Phase, as Monitored in Synchronously Infected Cell Cultures", J. Virol., Apr. 2007, 81, 3525-3534.
Halford, "Aiming for HIV's Weak Spot", Chemical & Engineering News, At War with HIV, Attacking the Virus Where it's Vulnerable, Chemical & Engineering News, Sep. 1, 2014, 14-21.
Halgren et al., "Glide: A New Approach for Rapid, Accurate Docking and Scoring. 2. Enrichment Factors in Database Screening", J. Med. Chem., Mar. 2004, 1750-1759.
Halgren, "MMFF VI. MMFF94s Option for Energy Minimization Studies", J. Comput. Chem., 1999, 20, 720-729.
Halgren, "MMFF VII. Characterization of MMFF94, MMFF94s, and Other Widely Available Force Fields for Conformational Energies and for Intermolecular-Interaction Energies and Geometries", J. Comput. Chem., 1999, 20, 730-748.
Heegaard et al., "Dendrimer Based Anti-Infective and Anti-Inflammatory Drugs", Recent Patents Anti-Infect. Drug Disc., Nov. 1, 2006, 1, 333-351.
Huang et al., "Scorpion-Toxin Mimics of CD4 in Complex with Human Immunodeficiency Virus gp120: Crystal Structures, Molecular Mimicry, and Neutralization Breadth", Structure, May 2005, 13, 755-768.

International Patent Application No. PCT/US12/60708: International Search Report dated Jan. 24, 2013, 4 pages.
Jones et al., "Development and Validation of a Genetic Algorithm for Flexible Docking", J. Mol. Biol., Aug. 1997, 267, 727-748.
Jorgensen et al., "Development and Testing of the OPLS All-Atom Force Field on Conformational Energetics and Properties of Organic Liquids", J. Am. Chem. Soc., Nov. 1996, 117, 11225-11236.
Karlsson et al., "The Envelope Glycoprotein Ectodomains Determine the Efficiency of CD4+ T Lymphocyte Depletion in Simian-Human Immunodeficiency Virus-Infected Macaques", J. Exp. Med., Sep. 1998, 188, 1159-1171.
Kassa, et al., "Transitions to and from the CD4-Bound Conformation are Modulated by a Single-Residue Change in the Human Immunodeficiency Virus Type 1 gp120 Inner Domain", J. Virol., Sep. 2009, 83(17), 8364-8378.
Korber et al., "Numbering Positions in HIV Relative to HXB2CG", Hum. Retroviruses AIDS III, Dec. 1998, 102-111.
Kunkel et al., "Rapid and Efficient Site-Specific Mutagenesis without Phenotypic Selection", Meth. Enzymol., 1987, 154, 367-382.
Kuntz et al., "Structure-Based Molecular Design", Accounts Chem. Res., May 1994, 27, 117-123.
Kwon, et al., "Crystal Structures of HIV-1 gp120 Envelope Glycoprotein in Complex with NBD Analogues that Target the CD4-Binding Site", PLOS One, Jan. 28, 2014, 9(1), 12 pgs.
Kwong et al., "Structure of an HIV gp120 envelope glycoprotein in complex with the CD4 receptor and a neutralizing human antibody", Nature, Jun. 1998, 393, 648-659.
Kwong et al., "Structures of HIV gp120 envelope glycoproteins from laboratory-adapted and primary isolates", Structure, Dec. 2000, 8, 1329-1339.
LaLonde et al., "Design, synthesis and biological evaluation of small molecule inhibitors of CD4-gp120 binding based on virtual screening", Bioorganic & Medicinal Chemistry, Jan. 2011, 19, 91-101.
LaLonde et al., "Structure-Based Design, Synthesis, and Characterization of Dual Hotspot Small-Molecule HIV-1 Entry Inhibitors", Journal of Medicinal Chemistry, May 2012, 55, 4382-4396.
Lalonde, et al., "Structure-Based Design and Synthesis of an HIV-1 Entry Inhibitor Exploiting X-Ray and Thermodynamic Characterization", ACS Med. Chem. Letter, Mar. 14, 2013, 4(3), 338-343.
Lin et al., "A small molecule HIV-1 inhibitor that targets the HIV-1 envelope and inhibits CD4 receptor binding", Proc. Natl. Acad. Sci., Sep. 2003, 100, 11013-11018.
Lovell et al., "Structure Validation by Cα Geometry: φ, ψ and Cβ Deviation", Proteins: Structure, Function and Genetics, Jan. 2003, 50, 285, 437-450.
Luque et al., "Structure-based prediction of binding affinities and molecular design of peptide ligands", Methods Enzymol, 1998, 295, 100-127.
Luty et al., "A Molecular Mechanics / Grid Method for Evaluation of Ligand-Receptor Interactions", J. Comp. Chem., 1995, 16, 454-464.
Madani et al., "Inhibition of Human Immunodeficiency Virus Envelope Glycoprotein-Mediated Single Cell Lysis by Low-Molecular-Weight Antagonists of Viral Entry", J. Virol., Jan. 2007, 81, 532-538.
Madani, et al., "CD4-Mimetic Small Molecules Sensitize Human Immunodeficiency Virus to Vaccine-Elicited Antibodies", Journal of Virology, Jun. 2014, 88(12):6542-6555.
Madani, et al., "Small-Molecule CD4 Mimics Interact with a Highly Conserved Pocket on HIV-1 gp120", Structure, Nov. 12, 2008, 16(11), 1689-1701.
Martin et al., "Rational design of a CD4 mimic that inhibits HIV-1 entry and exposes cryptic neutralization epitopes", Nat. Biotechnol., Jan. 2003, 21, 71-76.
Munro, et al., "Conformational Dynamics of Single HIV-1 Envelope Trimers on the Surface of Native Virions", Science, Nov. 7, 2014, 46(6210), 759-763.
Myszka et al., "Energetics of the HIV gp120-CD4 binding reaction", Proc. Natl. Acad. Sci., Aug. 2000, 97, 9026-9031.
Olshevsky et al., "Identification of Individual Human Immunodeficiency Virus Type 1 gp120 Amino Acids Important for CD4 Receptor Binding", J. Virol., Dec. 1990, 64, 5701-5707.

(56) References Cited

OTHER PUBLICATIONS

Orloff et al., "Two Mechanisms of Soluble CD4 (sCD4)-Mediated Inhibition of Human Immunodeficiency Virus Type 1 (HIV-1) Infectivity and Their Relation to Primary HIV-1 Isolates with Reduced Sensitivity to sCD4", J. Virol., Mar. 1993, 67, 1461-1471.
Rho et al., "Characterization of the Reverse Transcriptase from a New Retrovirus (HTLV) Produced by a Human Cutaneous T-Cell Lymphoma Cell Line", Virology, Jul. 1981, 112, 355-360.
Richard, et al., "CD4 Mimetics Sensitize HIV-1-Infected Cells to ADCC", PNAS, May 4, 2015, 112(20): E2687-E2694.
Robertson et al., "Protein Structure and the Energetics of Protein Stability", Chem. Rev., May 1997, 97, 1251-1268.
Rupp et al., "ViraGel™ (SPL7013 Gel): A candidate dendrimer—microbicide for the prevention of HIV and HSV infection", Int. J. Nanomedicine, 2007, 2(4), 561-566.
Schenten et al., "Effects of Soluble CD4 on Simian Immunodeficiency Virus Infection of CD4-Positive and CD4-Negative Cells", J. Virol., Jul. 1999, 73, 5373-5380.
Schon et al., "Thermodynamics of binding of a low-molecular-weight CD4 mimetic to HIV gp120", Biochemistry, Sep. 2006, 45, 10973-10980.
Si et al., "Small-molecule inhibitors of HIV-1 entry block receptor-induced conformational changes in the viral envelope glycoproteins", Proc. Natl. Acad. Sci., Apr. 2004, 101, 5036-5041.
Staudinger et al., "Evidence for CD4-enhanced Signaling through the Chemokine Receptor CCR5", J. Biol. Chem., Mar. 2003, 278, 10389-10392.
Stouten et al., "An Effective Solvation Term Based on Atomic Occupancies for Use in Protein Simulations", C Molecular Stimulation, Jan. 1993, 10(2-6), 97-120.
Strizki et al., "SCH-C (SCH 351125), an orally bioavailable, small molecule antagonist of the chemokine receptor CCR5, is a potent inhibitor of HIV-1 infection in vitro and in vivo", Proc. Natl. Acad. Sci., Oct. 23, 2001, 98(22), 12718-12723.
Sullivan et al., "Determinants of Human Immunodeficiency Virus Type 1 Envelope Glycoprotein Activation by Soluble CD4 and Monoclonal Antibodies", J. Virol., Aug. 1998, 72, 6332-6338.
Tagat et al., "Piperazine-Based CCR5 Antagonists as HIV-1 Inhibitors. IV. Discovery of 1-[4,6-Dimethyl-5-pyrimidinyl)carbonyl]-4-[4-{2-methoxy-1(R)-4-(trifluoromethyl)-phenyl}ethyl-3(S)-methyl-1-piperazinyl}-4-methylpiperdine (Sch-417690/Sch-D), a Potent, Highly Selective, and Orally Bioavailable CCR5 Antagonist", J. Med. Chem., May 6, 2004, 47(10, 2405-2408.

Thali et al., "Characterization of a Discontinuous Human Immunodeficiency Virus Type 1 gp120 Epitope Recognized by a Broadly Reactive Neutralizing Human Monoclonal Antibody", J. Virol., Nov. 1991, 65, 6188-6193.
Trikola et al., "CD4-dependent, antibody-sensitive interactions between HIV-1 and its co-receptor CCR-5", Nature, Nov. 1996, 384, 184-187.
Vita et al., "Rational engineering of a miniprotein that reproduces the core of the CD4 site interacting with HIV-1 envelope glycoprotein", Natl. Acad. Sci., Nov. 1999, 96, 13091-13096.
Weissenhorn et al., "Atomic structure of the ectodomain from HIV-1 gp41", Nature, May 1997, 387, 426-430.
Word et al., "Visualizing and Quantifying Molecular Goodness-of-Fit: Small-probe Contact Dots with Explicit Hydrogen Atoms", J. Mol. Biol., Jan. 1999, 285, 1711-1733.
Wu et al., "CD4-induced interaction of primary HIV-1 gp120 glycoproteins with the chemokine receptor-5", Nature, Nov. 1996, 384, 179-183.
Wyatt et al., "The HIV-1 Envelope Glycoproteins: Fusogens, Antigens, and Immunogens", Science, Jun. 1998, 280, 1884-1888.
Wyss et al., "The Highly Conserved C-Terminal Dileucine Motif in the Cytosolic Domain of the Human Immunodeficiency Virus Type 1 Envelope Glycoprotein is Critical for Its Association with the AP-1 Clathrin Adapter", J. Virol., Mar. 2001, 75, 2982-2992.
Xiang et al., "Functional Mimicry of a Human Immunodeficiency Virus Type 1 Coreceptor by a Neutralizing Monoclonal Antibody", J. Virol., May 2005, 79, 6068-6077.
Xiang et al., "Mutagenic stabilization and/or disruption of a CD4-bound state reveals distinct conformations of the human immunodeficiency virus type 1 gp120 envelope glycoprotein", J. Virol., Oct. 2002, 76, 9888-9899.
Xie, et al., "Structure-Activity Relationships in the Binding of Chemically Derivatized CD4 to gp120 from Human Immunodeficiency Virus", J. Med. Chem., Oct. 4, 2007, 50(20), 4898-4908.
Yoshimura et al., "Enhanced Exposure of Human Immunodeficiency Virus Type 1 Primary Isolate Neutralization Epitopes through Binding of CD4 Mimetic Compounds", Journal of Virology, Aug. 2010, vol. 84, No. 15, 7558-7568.
Zhang et al., "Antibody 17b Binding at the Coreceptor Site Weakens the Kinetics of the Interaction of Envelope Glycoprotein gp120 with CD4", Biochemistry, Feb. 2001, 40, 1662-1670.
Zhang et al., "Conformational changes of gp120 in epitopes near the CCR5 binding site are induced by CD4 and a CD4 miniprotein mimetic", Biochemistry, May 1999, 38, 9405-9416.
Zhang et al., "Expression, Purification, and Characterization of Recombinant HIV gp120", J. Biol. Chem., Oct. 2001, 276, 39577-39585.

\* cited by examiner

INHIBITORS OF HIV-1 ENTRY AND METHODS OF USE THEREOF

CROSS-REFERENCE TO RELATED APPLICATIONS

This application is the National Stage Application of International Patent Application No. PCT/US2015/044998, filed Aug. 13, 2015, which claims the benefit of U.S. Provisional Application No. 62/036,853, filed Aug. 13, 2014, the entireties of which are incorporated herein by reference.

GOVERNMENT SUPPORT

This invention was made with government support under Grant No. GM 56550 awarded by the National Institutes of Health. The government has certain rights in the invention.

BACKGROUND OF THE INVENTION

Preventing sexual transmission of human immunodeficiency virus (HIV-1) is critical for altering the course of the global pandemic of acquired immunodeficiency syndrome (AIDS). Currently, approximately 34 million people are living with HIV-1 infection; 2.5 million people are newly infected with the virus annually, and nearly 1.7 million individuals succumb each year to AIDS. Hence, there is an urgent need to develop strategies that can prevent HIV-1 transmission.

Targeting the early phase of HIV-1 infection, including virus entry, as a prophylactic modality is a focus of intense research. HIV-1 entry involves a series of events that include attachment to the host cell and fusion of the viral and target cell membranes. HIV-1 entry is mediated by the viral spike, which is composed of three gp120 envelope glycoproteins and three gp41 transmembrane molecules. In humans, HIV-1 infection begins with two consecutive gp120 binding events, each associated with major conformational changes in the gp120 structure. The first involves gp120 binding to the host CD4 receptor. CD4 binding results in a major gp120 conformational change, thus exposing a site for binding to the chemokine receptor (either CCR5 or CXCR4). Chemokine receptor binding is accompanied by gp41 rearrangement and the insertion of the gp41 fusion peptide into the host cell membrane, permitting fusion and viral entry. The highly conserved gp120-CD4 interface has been revealed by a number of X-ray crystal structures of the gp120 core domain, complexed to the D1D2 fragment of CD4 and a Fab of a human neutralizing antibody 17b, the latter serving as a surrogate for the co-receptors. CD4 binding induces the formation of a large internal cavity at the interface of the three gp120 domains, the inner domain, the outer domain, and the bridging sheet domain. The Phe43$_{CD4}$ and Arg59$_{CD4}$ residues have been shown by both mutagenesis and structural studies to be critical for binding of gp120 to CD4. Residue Phe43$_{CD4}$ is located on the CD4 CDR2-like loop and binds at the vestibule of the large cavity formed upon the CD4-induced gp120 conformational change; Arg59$_{CD4}$ is located on a neighboring β-strand and forms an electrostatic interaction with Asp368$_{gp120}$ at the cavity vestibule. The structure of the unbound form of the simian immunodeficiency virus (SIV) gp120, which has a 35% sequence identity with HIV-1 gp120, indicates an invariant outer domain, with conformational changes occurring in both the bridging sheet and inner domain. Recent studies indicate that the HIV-1 gp120 core exhibits a propensity to assume the CD4-bound conformation, but is restrained from doing so by gp120 variable loops and interactions with gp41 in the context of the trimer spike. The thermodynamic signature of the CD4-induced gp120 conformational change exhibits a highly favorable binding enthalpy balanced with a highly unfavorable entropy associated with molecular ordering.

Two N-phenyl-N'-(2,2,6,6,-tetramethyl-piperidin-4-yl)-oxalamide compounds, NBD-556 and NBD-557, were identified via screening a drug-like small-molecule library for inhibition of gp120-CD4 binding. Mutagenesis, modeling and synthesis of NBD analogues with improved binding affinity revealed that these small molecules bind to the highly conserved gp120 cavity and compete with CD4 binding. Exploration of structure-activity relationships (SAR) demonstrated that compounds with comparable binding affinities act both as CD4 antagonists (i.e., to inhibit HIV-1-infection of CD4+ cells) and as CD4 agonists (i.e., promote CCR5 binding and enhance viral infection in the absence of CD4). Mimicry of CD4 was further demonstrated by the similarity of the NBD and CD4 thermodynamic signatures, both exhibiting a large unfavorable entropy change, $-T\Delta S$, to Gibbs energy (17.1 kcal/mol and 24.1 kcal/mol for NBD-556 and CD4, respectively) compensated by a large favorable enthalpy change (−24.5 kcal/mol and −34.5 kcal/mol for NBD-556 and CD4, respectively). Taken together, these results provided a rationale for further optimization of NBD analogues as inhibitors of HIV-1 viral entry by focusing on both Phe43 cavity and Asp368$_{gp120}$ hotspots.

There exists a need for small molecule inhibitors exhibiting improved thermodynamic and antiviral properties that are useful in treating or preventing HIV.

In addition to small molecule inhibitors of HIV, HIV-1-neutralizing antibodies are an important component of a protective vaccine-induced immune response. Passive administration of HIV-1-neutralizing antibodies protects monkeys from intravenous and mucosal challenge with simian-human immunodeficiency viruses (SHIVs). The trimeric envelope glycoprotein (Env) spike on the virion surface is the only HIV-1-specific target accessible to neutralizing antibodies. The presence of circulating antibodies against a specific region of Env (the gp120 V2 variable region) correlated with the partial protection seen in the RV144 clinical vaccine trial. Thus, the generation of anti-Env antibodies, particularly neutralizing antibodies, may be critical for a successful HIV-1 vaccine.

The HIV-1 Env spike described above, which is composed of three gp120 exterior Envs and three gp41 transmembrane Envs, mediates virus entry into host cells. The unliganded HIV-1 Env is metastable. Binding of gp120 to the initial receptor, CD4, triggers Env conformational changes that result in the formation/exposure of two elements: 1) the gp120 binding site for the second receptor, CCR5 or CXCR4, and 2) the gp41 heptad repeat (HR1) coiled coil. Binding of gp120 to the CCR5 or CXCR4 coreceptor is thought to induce further Env conformational changes that result in the formation of an energetically stable gp41 six-helix bundle that promotes the fusion of the viral and target cell membranes.

As a successful persistent virus, HIV-1 has evolved Env spikes that minimize the elicitation and impact of neutralizing antibodies. These features include surface variability, conformational lability and a heavy coat of glycans. Most anti-Env antibodies elicited during natural infection do not neutralize HIV-1, and those that do are usually strain-restricted, allowing virus escape. Only after several years of infection in some HIV-1-infected individuals are more broadly neutralizing antibodies generated. Broadly HIV-1-neutralizing antibodies typically display unusual features that allow binding to the heavily shielded, conserved Env epitopes. Some neutralizing antibodies with modest breadth bind Env carbohydrate-dependent epitopes. The variable and glycosylated features of the HIV-1 Env spike render the elicitation of neutralizing antibodies difficult, and have presented extreme challenges to the development of effective Env vaccine immunogens. Even the best current HIV-1 Env immunogens elicit antibodies that inhibit the infection only of the small subset of primary viruses that are more prone to neutralization. The sensitivity of HIV-1 strains to antibody neutralization depends upon the integrity of the Env epitope and Env reactivity; the latter property indicates the propensity of unliganded Env to undergo conformational changes. A successful HIV-1 vaccine must cover a range of phylogenetically diverse transmitted/founder viruses, most of which have Envs of low reactivity and thus exhibit low sensitivity to neutralization by antibodies.

One of the major hurdles facing the development of a successful HIV-1/AIDS vaccine is the requirement to elicit antibodies that recognize conserved elements of the native, unliganded conformation of the HIV-1 Env trimer. These conserved elements are often buried or composed partially or in some cases completely of glycans, which render the generation of the cognate antibodies inefficient. Two functionally conserved gp120 elements interact with the HIV-1 host cell receptors, CD4 and CCR5/CXCR4. The CD4-binding site (CD4BS) on gp120 is sterically recessed on the HIV-1 Env trimer and surrounded by regions that exhibit inter-strain variability and glycosylation. Effective neutralizing antibodies directed against the gp120 CD4BS typically engage their epitopes in a manner that does not require the Env trimer to undergo significant conformational changes. Indeed, potently neutralizing antibodies directed against multiple conserved HIV-1 Env epitopes generally require minimal conformational change in the unliganded Env trimer for their binding.

The vast majority of primary HIV-1 isolates, including transmitted/founder viruses, use CCR5 as a second receptor. The CCR5-binding site on gp120 consists of a discontinuous surface of the gp120 core and the tip of the V3 loop, both of which are well conserved among primate immunodeficiency viruses. These elements are not formed and exposed on HIV-1 Env trimers with low envelope reactivity. Antibodies that recognize CD4-induced (CD4i) epitopes in the gp120 core bind near or within the coreceptor-binding site of gp120. Some of these antibodies are specific for CCR5-using HIV-1 variants, whereas other antibodies recognize both CCR5-using and CXCR4-using viruses. CD4i antibodies are routinely generated in HIV-1-infected humans, and can be elicited by HIV-1 gp120 core constructs in which the CD4-bound conformation has been stabilized by disulfide bonds and cavity-filling substitutions. Although both the CD4i epitopes and the V3 tip become exposed after HIV-1 binding to cell-surface CD4, steric factors (e.g., the target cell membrane) limit the ability of CD4i and V3-directed antibodies to bind their respective epitopes and neutralize the virus. Therefore, the neutralizing potency of CD4i and V3-directed antibodies is related to the degree of exposure of these epitopes on the unliganded Env trimer. Thus, because of the low Env reactivity of primary and transmitted/founder HIV-1, these viruses are generally inhibited poorly by most CD4i and V3-directed antibodies.

There exists a need for methods of eliciting antibodies that bind the unliganded HIV-1 Env trimer efficiently and neutralize the large fraction of primary transmitted/founder HIV-1 with low Env reactivity.

Furthermore, induction of the CD4-bound conformation renders primary HIV-1 sensitive to neutralization by CD4i antibodies. HIV-1 sensitization as a strategy for virus prophylaxis has become feasible as a result of the availability of small-molecule CD4-mimetic compounds. As mentioned above, NBD-556 and NBD-557, were discovered in a screen for inhibitors of gp120-CD4 interaction. NBD-556 and NBD-557 bind in the Phe 43 cavity, a highly conserved ~150 cubic Angstrom pocket in the gp120 glycoprotein of all HIV-1 strains except those in Group O. The vestibule of the Phe 43 cavity contains a number of conserved gp120 residues that make critical contacts with CD4. The binding of NBD compounds in the Phe 43 cavity blocks gp120-CD4 interaction and, like the binding of soluble CD4, prematurely triggers the activation of the HIV-1 Env spike. The activated state is short-lived ($t_{1/2}$=5-7 minutes at 37° C.) and the bound Env spike rapidly decays into an irreversibly inactivated state. Although NBD-556 induces large, entropically unfavorable changes in gp120 conformation and thus binds with only modest affinity ($K_d$=3 μM), iterative cycles of co-crystallization with gp120 and rational design and synthesis have yielded a number of NBD-556 analogues with improved affinity and antiviral properties. However, NBD-556 suffers from one significant disadvantage with respect to development of a vaccine: it increases the binding or neutralizing potency of the 17b CD4i antibody weakly and only in laboratory-adapted viruses that have high Env reactivity.

There also exists a need for a method of increasing the sensitivity of the HIV-1 virion to antibody neutralization.

SUMMARY OF THE INVENTION

In certain embodiments, the disclosure relates to a compound of Formula I

Formula I or a salt or solvate thereof,
wherein
R$^1$ is wherein n is 1;
R$^{2A}$ is H, optionally substituted alkylaminoalkyl, optionally substituted cycloalkylaminoalkyl, or

[Structure: wavy-N(R⁶)-CH₂-C(=NH)-NH₂]

R³ᴬ is H, optionally substituted alkylaminoalkyl, optionally substituted cycloalkylaminoalkyl, or

[Structure: wavy-N(R⁶)-CH₂-C(=NH)-NH₂]

R⁴ᴬ is H, optionally substituted alkylaminoalkyl, optionally substituted cycloalkylaminoalkyl, or

[Structure: wavy-N(R⁶)-CH₂-C(=NH)-NH₂]

R⁵ᴬ is H, optionally substituted alkylaminoalkyl, optionally substituted cycloalkylaminoalkyl, or

[Structure: wavy-N(R⁶)-CH₂-C(=NH)-NH₂]

provided at least one of $R^{2A}$, $R^{3A}$, $R^{4A}$, or $R^{5A}$ is optionally substituted alkylaminoalkyl, optionally substituted cycloalkylaminoalkyl, or

[Structure: wavy-N(R⁶)-CH₂-C(=NH)-NH₂]

In certain embodiments, the disclosure relates to a compound of Formula II

[Structure of Formula II: 4-Cl, 3-F substituted aniline connected via NH-C(=O)-C(=O)-NH to an indane bearing R¹, with R²ᴮ, R³ᴮ, R⁴ᴮ, R⁵ᴮ on the aromatic ring]

Formula II or a salt or solvate thereof, wherein
R¹ is

[Structure: wavy-(CH₂)ₙ-NH-C(=NH)-NH₂]

wherein n is 1;
$R^{2B}$ is H, bromo, or chloro;
$R^{3B}$ is H, bromo, or chloro;
$R^{4B}$ is H, bromo, or chloro;
$R^{5B}$ is H, bromo, or chloro;
provided at least one of $R^{2B}$, $R^{3B}$, $R^{4B}$, or $R^{5B}$ is bromo or chloro.

Methods of using the compounds of the disclosure are also described. For example, methods of using the compounds of the disclosure to activate HIV exterior envelope glycoprotein gp120; to inhibit transmission of HIV to a cell; to inhibit the progression of HIV infection in a cell; to inhibit the transmission or progression of HIV to a cell; to generate a protein binding domain that specifically binds to gp120 in a specific conformational state; neutralize HIV-1; or to treat or prevent HIV infection are also described. Complexes comprising a compound of the disclosure, gp120 in a functional conformational state, and optionally, an antibody, are also described.

DETAILED DESCRIPTION OF THE INVENTION

In certain embodiments, the disclosure relates to compounds and methods useful in inhibiting viral entry.

In certain embodiments, the disclosure relates to a method of sensitizing primary HIV-1, including transmitted/founder viruses, to neutralization by monoclonal antibodies directed against CD4-induced (CD4i) epitopes and the V3 region, two gp120 elements involved in coreceptor binding. In certain embodiments, the disclosure relates to the sensitization of primary HIV-1 by small-molecule compounds to neutralization by antisera elicited by immunization of rabbits with HIV-1 gp120 cores engineered to assume the CD4-bound state. In certain embodiments, the disclosure relates to the use of small molecules as microbicides to inhibit HIV-1 infection directly and to sensitize primary HIV-1 to neutralization by readily elicited antibodies. In certain embodiments, the virus-sensitizing activity of the small-molecule compounds is robust. In certain embodiments, the virus-sensitizing activity of the small-molecule compounds is evident in primary HIV-1 isolates that have low Env reactivity and thus are relatively neutralization-resistant.

An attractive strategy for preventing HIV-1 acquisition is to generate antibodies in an uninfected individual that potently neutralize a wide range of transmitted/founder HIV-1. Both viral and antibody factors determine HIV-1 neutralization efficiency. Transmitted/founder viruses generally exhibit low Env reactivity and thus are relatively resistant to neutralization. Antibodies that effectively neutralize these low-reactivity viruses must bind the unliganded Env trimer efficiently, without requiring significant conformational changes in Env. In certain embodiments, the disclosure relates to an approach that increases the sensitivity of the HIV-1 virion to some neutralizing antibodies. In certain embodiments, the approach takes advantage of: 1)

the natural tendency of HIV-1 Env to make the transition from the unliganded state to the CD4-bound state; 2) the highly conserved nature of the gp120 binding sites for CD4 and CCR5; 3) the vulnerability to antibody neutralization of the CD4-bound state of Env on a virus that is distant from the target membrane; and 4) the availability of small-molecule CD4-mimetic compounds that exhibit sufficient affinity and breadth.

In certain embodiments, the compounds sensitize primary HIV-1 isolates, which have low envelope reactivity and are relatively neutralization resistant, to inhibition by specific anti-gp120 antibodies. In certain embodiments, the disclosure relates to the theory that, in the presence of the inventive compounds, multiple primary HIV-1, including transmitted/founder HIV-1, are sensitive to neutralization by the 17b antibody or antisera elicited by a 3CC gp120 core immunogen. Importantly, in certain embodiments, the observed sensitization seen with the viruses was dependent on the binding of the compounds to the viral Env. In certain embodiments, the compounds do not bind to the S375W variant of HIV-1 Env, where the Phe 43 cavity is filled and therefore unavailable for compound binding. In certain embodiments, sensitization of HIV-1 to neutralization by antibodies apparently requires sufficient affinity of the CD4-mimetic compound for Env.

In certain embodiments, the CD4i and V3-directed anti-gp120 antibodies neutralized HIV-1 with dramatically improved potency in the presence of the compounds described herein. These two groups of antibodies recognize gp120 epitopes that share several features: 1) poor formation/exposure on the unliganded HIV-1 Env trimer; 2) induction by CD4 binding; 3) involvement in coreceptor binding; and 4) a high degree of conservation in the components of the epitope that interact with the coreceptor.

In certain embodiments, the methods of enhancing vaccine efficacy comprise the step of co-administering a compound described herein. One frustrating aspect of HIV-1 vaccine development is the difficulty of eliciting antibodies that potently neutralize diverse strains of virus. Sensitization of HIV-1, including transmitted/founder viruses, by the inventive compounds could result in a virus that is neutralizable by antibodies that can be readily elicited. During HIV-1 infection of humans, CD4i antibodies are elicited early and in a high proportion of infected individuals; this suggests that the generation of such antibodies in humans may be achievable by vaccination. Moreover, "stabilized gp120 cores" that have been engineered to assume the CD4-bound state have been demonstrated to raise CD4i antibodies in immunized rabbits. Thus, the two fundamental components of a prophylactic approach based on HIV-1 sensitization are in place: 1) compounds that inhibit HIV-1 entry and also sensitize HIV-1 to neutralization by CD4i and V3-directed antibodies; and 2) stabilized gp120 core immunogens that can elicit CD4i antibodies. In certain embodiments, multi-component vaccine regimens are provided in which one of the immunogens is a stabilized gp120 core that elicits antibodies against the conserved coreceptor-binding site. The compounds described herein administered orally or in a microbicide formulation could sensitize a range of transmitted/founder viruses to inhibition by the vaccine-elicited antibodies.

In certain embodiments, compounds described herein exhibit enhanced activity as compared to the activity of known compounds. For example, the $IC_{50}$ of the compounds described herein is about 50% of the $IC_{50}$ of known compounds in the same assay, or about 10% of the $IC_{50}$ of known compounds in the same assay, or about 1% of the $IC_{50}$ of known compounds in the same assay.

Definitions

In order for the present disclosure to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes herein, the heteroatoms such as nitrogen may have hydrogen substituents and/or any permissible substituents of organic compounds described herein which satisfy the valences of the heteroatoms. This disclosure is not intended to be limited in any manner by the permissible substituents of organic compounds.

The term "lower" when appended to any of the groups listed below indicates that the group contains less than seven carbons (i.e. six carbons or less). For example "lower alkyl" refers to an alkyl group containing 1 to about 6 carbons, and "lower alkenyl" refers to an alkenyl group containing 2 to about 6 carbons.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon.

For purposes of this disclosure, the chemical elements are identified in accordance with the Periodic Table of the Elements, CAS version, Handbook of Chemistry and Physics, 67th Ed., 1986-87, inside cover.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means an aliphatic or cyclic hydrocarbon radical containing from 1 to about 12 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, and 1-cyclohexylethyl. Any alkyl described herein may be a substituted alkyl.

The term "substituted alkyl" means an aliphatic or cyclic hydrocarbon radical containing from 1 to about 12 carbon atoms, substituted with 1, 2, 3, 4, or 5 substituents independently selected from the group consisting of alkyl, alkenyl, alkynyl, halo, haloalkyl including fluoroalkyl, hydroxy, alkoxy (—O-alkyl), alkenyloxy (—O-alkenyl), alkynyloxy (—O-alkynyl), alkylphenyl such as benzyl ($CH_2$-phenyl) and $CH_2CH_2$-phenyl, aryl, heteroaryl, heterocyclyl, carbocyclyloxy (—O-carbocyclyl), heterocyclyloxy (—O-heterocyclyl), haloalkoxy (—O-haloalkyl) such as fluoroalkyloxy, sulfhydryl (—SH), alkylthio (—S-alkyl), haloalkylthio (—S-haloalkyl) such as fluoroalkylthio, alkenylthio (—S-alkenyl), alkynylthio (—S-alkynyl), sulfonic acid ($SO_2OH$), alkylsulfonyl (—$SO_2$-alkyl), haloalkylsulfonyl (—$SO_2$-haloalkyl), fluoroalkylsulfonyl (—$SO_2$-fluoroalkyl), alkenylsulfonyl (—$SO_2$-alkenyl), alkynylsulfonyl (—$SO_2$-alkynyl), alkoxysulfonyl (—$SO_2$-alkoxy), haloalkoxysulfonyl (—$SO_2$-haloalkoxy), fluoroalkoxysulfonyl (—$SO_2$-fluoroalkoxy), alkenyloxysulfonyl (—$SO_2$—O-alkenyl), alkynyloxysulfonyl (—$SO_2$—O-alkynyl), aminosulfonyl (—$SO_2$—$NH_2$), sulfinic acid (—$SO_2H$), alkylsulfinyl (—SO-(alkyl)$_2$), haloalkylsulfinyl (—SO-(fluoroalkyl)$_2$), fluoroalkylsulfinyl, alkenylsulfinyl (—SO-(alkenyl)$_2$), alkynylsulfinyl (—SO-(alkynyl)$_2$), alkoxysulfinyl (—SO-(alkoxy)$_2$), haloalkoxysulfinyl (—SO-(haloalkoxy)$_2$) such as fluoroalkoxysulfinyl, alkenyloxysulfinyl (—SO—O-(alkenyl)$_2$), alkynyloxysulfinyl (—SO-(alkynyl)$_2$), aminosulfinyl, formyl, alkylcarbonyl (—C(O)-alkyl), haloalkylcarbonyl (—C(O)-haloalkyl) such as fluoroalkylcarbonyl, alkenylcarbonyl (—C(O)-alkenyl), alkynylcarbonyl (—C(O)-alkynyl), carboxy (COOH), alkoxycarbonyl (—C(O)-alkoxy), haloalkoxycarbonyl (—C(O)-haloalkoxy), fluoroalkoxycarbonyl (—C(O)-fluoroalkoxy), alkenyloxycarbonyl (—C(O)—O-alkenyl), alkynyloxycarbonyl (—C(O)—O-alkynyl), alkylcarbonyloxy (—O—C(O)-alkyl), haloalkylcarbonyloxy (—O—C(O)-haloalkyl) such as fluoroalkylcarbonyloxy, alkenylcarbonyloxy (—O—C(O)-alkenyl), alkynylcarbonyloxy (—O—C(O)-alkynyl), alkylsulfonyloxy (—O—$SO_2$-alkyl), haloalkylsulfonyloxy (—O—$SO_2$-haloalkyl), fluoroalkylsulfonyloxy (—O—$SO_2$-fluoroalkyl), alkenylsulfonyloxy (—O—$SO_2$-alkenyl), alkynylsulfonyloxy (—O—$SO_2$-alkynyl), haloalkoxysulfonyloxy (—O—$SO_2$-haloalkoxy), fluoroalkoxysulfonyloxy (—O—$SO_2$-fluoroalkoxy), alkenyloxysulfonyloxy (—O—$SO_2$-alkenyl), alkynyloxysulfonyloxy (—O—$SO_2$-alkynyl), alkylsulfinyloxy (—O—SO-alkyl), haloalkylsulfinyloxy (—O—haloalkyl) such as fluoroalkylsulfinyloxy, alkenylsulfinyloxy (—O—SO-alkenyl), alkynylsulfinyloxy (—O—SO-alkynyl), alkoxysulfinyloxy (—O—SO-alkoxy), haloalkoxysulfinyloxy (—O—SO-haloalkoxy), fluoroalkoxysulfinyloxy (—O—SO-fluoroalkoxy), alkenyloxysulfinyloxy (—O—SO—O-alkenyl), alkynyloxysulfinyloxy (—O—SO—O-alkynyl), aminosulfinyloxy (—O—SO—NH$_2$), amino, amido (C(O)NH$_2$), cyano, nitro, azido, phosphinyl, phosphoryl, silyl and silyloxy.

"Alkenyl" refers to a monoradical of a branched or unbranched hydrocarbon chain containing at least one double bond. Alkenyl groups may contain 2-10 carbon atoms, such as 2-6 carbon atoms or 2-4 carbon atoms.

"Alkynyl" refers to a monoradical of a branched or unbranched hydrocarbon chain containing at least one triple bond. Alkynyl groups may contain 2-10 carbon atoms, such as 2-6 carbon atoms or 2-4 carbon atoms.

The term "carbocyclyl" or "cycloalkyl" as used herein means monocyclic or multicyclic (e.g., bicyclic, tricyclic, etc.) hydrocarbons containing from 3 to about 12 carbon atoms that is completely saturated or has one or more unsaturated bonds, and for the avoidance of doubt, the degree of unsaturation does not result in an aromatic ring system (e.g. phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "halo" or "halogen" means Cl, Br, I or F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein all the hydrogens are replaced with fluorines.

The term "amino" as used herein refers to —NH$_2$ and substituted derivatives thereof wherein one or both of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl (C(O)carbocyclyl), heterocyclylcarbonyl (C(O)heterocyclyl), arylcarbonyl (CC(O)aryl), aralkylcarbonyl (C(O)aralkyl), heteroarylcarbonyl (C(O)heteroaryl), heteroaralkylcarbonyl (C(O)heteroaralkyl) and the sulfonyl and sulfinyl groups defined above; or when both hydrogens together are replaced with an alkylene group (to form a ring which contains the nitrogen). Representative examples include, but are not limited to methylamino, acetylamino, and dimethylamino.

"Aryl" refers to 6-15 membered monoradical bicyclic or tricyclic hydrocarbon ring systems, including bridged, spiro, and/or fused ring systems, in which at least one of the rings is aromatic. An aryl group may contain 6 (i.e., phenyl) or about 9 to about 15 ring atoms, such as 6 (i.e., phenyl) or about 9 to about 11 ring atoms. In certain embodiments, aryl groups include, but are not limited to, naphthyl, indanyl, indenyl, anthryl, phenanthryl, fluorenyl, 1,2,3,4-tetrahydronaphthalenyl, 6,7,8,9-tetrahydro-5H-benzocycloheptenyl, and 6,7,8,9-tetrahydro-5H-benzocycloheptenyl.

"Heteroaryl" refers to (a) 5 and 6 membered monocyclic aromatic rings, which contain, in addition to carbon atoms, at least one heteroatom, such as nitrogen, oxygen or sulfur, and (b) 7-15 membered bicyclic and tricyclic rings, which contain, in addition to carbon atoms, at least one heteroatom, such as nitrogen, oxygen or sulfur, and in which at least one ring is aromatic. Heteroaryl groups can be bridged, spiro, and/or fused. In further embodiments, a heteroaryl may contain 5 to about 15 ring atoms. In further embodiments, a heteroaryl may contain 5 to about 10 ring atoms, such as 5, 6, 9, or 10 ring atoms. The heteroaryl may be C-attached or N-attached where such is possible and results in the creation of a stable structure. Examples include, but are not limited to 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, imidazolyl, isoxazolyl, isothiazolyl, oxadiazolyl, oxazolyl, pyridinyl, pyrimidinyl, pyrazolyl, pyrrolyl, pyrazinyl, pyridazinyl, pyrazinyl, thienyl, tetrazolyl, thiazolyl, thiadiazolyl, triazinyl, triazolyl, naphthyridinyl, pteridinyl, phthalazinyl, purinyl, alloxazinyl, benzimidazolyl, benzofuranyl, benzofurazanyl, 2H-1-benzopyranyl, benzothiadiazinyl, benzothiazinyl, benzothiazolyl, benzothiophenyl, benzoxazolyl, cinnolinyl, furopyridinyl, indolinyl, indolizinyl, indolyl, quinazolinyl, quinoxalinyl, isoindolyl, isoquinolinyl, 10-aza-tricyclo[6.3.1.0$^{2,7}$]dodeca-2(7),3,5-trienyl, 12-oxa-10-aza-tricyclo[6.3.1.0$^{2,7}$]dodeca-2(7),3,5-trienyl, 12-aza-tricyclo[7.2.1.0$^{2,7}$]dodeca-2(7),3,5-trienyl, 10-aza-tricyclo[6.3.2.0$^{2,7}$]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl.

"Heterocycle" refers to 3-15 membered monocyclic, bicyclic, and tricyclic non-aromatic rings, which may be saturated or unsaturated, may be bridged, spiro, and/or fused, and which contain, in addition to carbon atoms, at least one heteroatom, such as nitrogen, oxygen, sulfur or phosphorus. A heterocycle may contain, in addition to carbon atoms, at least one nitrogen, oxygen, or sulfur. A heterocycle may contain from 3 to about 10 ring atoms, 3 to about 7 ring atoms, 5 to 7 ring atoms, 5 ring atoms, 6 ring atoms, or 7 ring atoms. Unless otherwise indicated, the heterocycle can be C-attached or N-attached where such is possible and results in the creation of a stable structure. Examples include, but are not limited to, tetrahydrofuranyl, pyrrolidinyl, pyrrolinyl, imidazolidinyl, imidazolinyl, azetidinyl, pyrazolidinyl, pyrazolinyl, piperidinyl, piperazinyl, indolinyl, isoindolinyl, morpholinyl, thiomorpholinyl, homomorpholinyl, homopiperidinyl, homopiperazinyl, thiomorpholinyl-5-oxide, thiomorpholinyl-S,S-dioxide, tetrahydropyranyl, piperidinyl, tetrahydrothienyl, homothiomorpholinyl-S,S-dioxide, oxazolidinonyl, dihydropyrazolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, quinuclidinyl, 2-oxa-5-azabicyclo[2.2.1]heptanyl, 8-oxa-3-aza-bicyclo[3.2.1]octanyl, 3,8-diaza-bicyclo[3.2.1]octanyl, 2,5-diaza-bicyclo[2.2.1]heptanyl, 3,8-diaza-bicyclo[3.2.1]octanyl, 3,9-diazabicyclo[4.2.1]nonanyl, 2,6-diaza-bicyclo[3.2.2]nonanyl, [1,4]oxaphosphinanyl-4-oxide, [1,4]azaphosphinanyl-4-oxide, [1,2]oxaphospholanyl-2-oxide, phosphinanyl-1-oxide, [1,3]azaphospholidinynl-3-oxide, [1,3]oxaphospholanyl-3-oxide and 7-oxabicyclo[2.2.1]heptanyl.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

As used herein, the term "administering" means providing a pharmaceutical agent or composition to a subject, and includes, but is not limited to, administering by a medical professional and self-administering.

As used herein, the phrase "pharmaceutically acceptable" refers to those agents, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "pharmaceutically-acceptable carrier" means a pharmaceutically-acceptable material, composition or vehicle, such as a liquid or solid filler, diluent, excipient, or solvent encapsulating material, involved in carrying or transporting an agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As used herein, the phrase "salts" refers to the inorganic and organic salts of compounds. Some salts of the disclosure may be pharmaceutically acceptable salts, which are generally non-toxic inorganic and organic salts of compounds. Acid addition salts include, but are not limited to hydrochloride, hydrobromide, hydroiodide, nitrate, sulfate, bisulfate, phosphate, acid phosphate, isonicotinate, carbonate, bicarbonate, acetate, lactate, salicylate, citrate, tartrate, propionate, butyrate, pyruvate, oxalate, malonate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, trifluoromethanesulfonate, and pamoate (i.e., 1,1'-methylene-bis-(2-hydroxy-3-naphthoate)) salts.

As used herein, the term "subject" means a human or non-human animal selected for treatment or therapy.

As used herein, the phrase "subject suspected of having" means a subject exhibiting one or more clinical indicators of a disease or condition.

As used herein, the phrase "therapeutic effect" refers to a local or systemic effect in animals, particularly mammals, and more particularly humans, caused by an agent. The phrases "therapeutically-effective amount" and "effective amount" mean the amount of an agent that produces some desired effect in at least a sub-population of cells. A therapeutically effective amount includes an amount of an agent that produces some desired local or systemic effect at a reasonable benefit/risk ratio applicable to any treatment. For example, certain agents used in the methods described herein may be administered in a sufficient amount to produce a reasonable benefit/risk ratio applicable to such treatment.

As used herein, the term "treating" a disease in a subject or "treating" a subject having or suspected of having a disease refers to subjecting the subject to a pharmaceutical treatment, e.g., the administration of an agent, such that at least one symptom of the disease is decreased or prevented from worsening.

As used herein, "HIV" refers to any virus that can infect a host cell of a subject through activation of the gp120 envelope glycoproteins (Env gps). "HIV" encompasses all strains of HIV-1 and HIV-2. The compounds described herein, however, are also useful to treat other immunodeficiency viruses expressing gp120 such as some strains of simian immunodeficiency virus SIV.

As used herein "gp120" refers to the gp120 envelope glycoprotein, and "Env gps" refers to the complete envelope glycoprotein complex which is a trimer of three gp120s and three gp41s.

As used herein, the term "activating" when referring to gp120 envelope glycoprotein means the association of a natural or non-natural ligand with the conserved domain of gp120 that induces a conformational change that activates binding to the chemokine receptors CCR5 or CXCR4. Examples of natural ligands include CD4 and sCD4. Examples of non-natural ligands include compounds described herein as well as NBD-556 and NBD-557.

As used herein "activated intermediate" refers to the gp120 envelope glycoprotein in bound form with CD4, sCD4, or compounds described herein.

As used herein, the term "contacting" when used in the context of compounds described herein and gp120, refers to the process of supplying compounds described herein to the HIV envelope glycoprotein either in vitro or in vivo in order effect the selective binding of the compounds described herein to the conserved Phe43 binding pocket of gp120. For the in vitro process, this can entail simply adding an amount of a stock solution of one or more compounds described herein to a solution preparation of gp120. For an in vivo process, "selective binding" involves making compounds described herein available to interact with gp120 in a host organism, wherein the compounds described herein exhibit a selectivity for the conserved domain of gp120 that define the Phe43 cavity. Making the compounds available to interact with gp120 in the host organism can be achieved by oral administration, intravenously, peritoneally, mucosally, intramuscularly, and other methods familiar to one of ordinary skill in the art.

As used herein, the term "inhibiting" when referring to transmission means reducing the rate of or blocking the process that allows fusion of the viral glycoprotein gp120 to a host cell and introduction of the viral core into the host cell. In this regard, inhibiting transmission includes prophylactic measures to prevent viral spread from one host organism to another. When referring to progression, "inhibiting" refers to the treatment of an already infected organism and preventing further viral invasion within the same organism by blocking the process that allows fusion of the viral glycoprotein gp120 and introduction of viral core into additional host cells of the organism.

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab)$_2$, a Fd fragment, a Fv fragments, and dAb fragments) as well as complete antibodies.

The term "conformation" or "conformational state" of a protein refers generally to the range of structures that a protein may adopt at any instant in time. One of skill in the art will recognize that determinants of conformation or conformational state include a protein's primary structure as reflected in a protein's amino acid sequence (including modified amino acids) and the environment surrounding the protein. The conformation or conformational state of a protein also relates to structural features such as protein secondary structures (e.g., α-helix, β-sheet, among others), tertiary structure (e.g., the three dimensional folding of a polypeptide chain), and quaternary structure (e.g., interactions of a polypeptide chain with other protein subunits). Post-translational and other modifications to a polypeptide chain such as ligand binding, phosphorylation, sulfation, glycosylation, or attachments of hydrophobic groups, among others, can influence the conformation of a protein. Furthermore, environmental factors, such as pH, salt concentration, ionic strength, and osmolality of the surrounding solution, and interaction with other proteins and co-factors, among others, can affect protein conformation. The conformational state of a protein may be determined by either functional assay for activity or binding to another molecule or by means of physical methods such as X-ray crystallography, NMR, or spin labeling, among other methods. For a general discussion of protein conformation and conformational states, one is referred to Cantor and Schimmel, Biophysical Chemistry, Part I: The Conformation of Biological Macromolecules, W.H. Freeman and Company, 1980, and Creighton, Proteins: Structures and Molecular Properties, W.H. Freeman and Company, 1993. A "specific conformational state" is any subset of the range of conformations or conformational states that a protein may adopt.

Compounds of the disclosure include at least two chiral stereocenters. As such, as least four stereoisomers are possible for any compound of the disclosure. Preferably, the compounds of the invention are provided as single stereoisomers. As used herein, the term "stereoisomers" refers to at least two compounds having the same molecular formula and connectivity of atoms, but having a different arrangement of atoms in a three-dimensional space. A stereoisomer can be, for example, an enantiomer or a diastereomer.

As used herein, the term "enantiomers" refers to a pair of compounds which are non-superimposable mirror images of one another. In other words, an "enantiomer" is a stereoisomer that cannot be superimposed on its mirror image. Chemists employ various naming conventions to distinguish enantiomers from one another. Because an enantiomer can rotate plane-polarized light, chemists sometime designate enantiomers using the symbols (+) and (−) or d and l depending on whether they rotate plane-polarized light in a clockwise or counterclockwise direction, respectively. The former enantiomer is termed to be dextrorotatory and the latter enantiomer is termed to be levorotatory. As a result of this behavior in the presence of plane-polarized light, enantiomers have also been referred to as "optical isomers." Enantiomers have identical physical and chemical properties in an achiral environment but each rotates the plane of polarized light to the same number of degrees but in the opposite direction.

As used herein, "diastereomers" are stereoisomers which are not mirror images.

As used herein, the term "optical rotation" refers to the number of degrees of rotation of plane polarized light exhibited by an optically active stereoisomer, such as an enantiomer, either neat or in solution. Optical rotation is usually measured with a polarimeter. The "specific rotation" is calculated from the observed optical rotation taking into account the concentration of the optically active molecule and the dimensions of the vessel containing the optically active molecules. The wavelength of plane polarized light usually employed is the "D line" of sodium.

As used herein, the terms "stereochemically pure" and "stereoisomerically pure" refer to a composition or compound containing a substantially pure stereoisomer of a compound. The term "substantially pure," when used with reference to a stereoisomer, such as an enantiomer or diastereomer, means that the composition or compound is substantially free of all the other stereoisomers of that compound, but not necessarily free from other materials (e.g., solvents, other compounds, etc.). According to embodiments of the present invention, a stereochemically pure composition or compound comprises about 97% by weight (w/w) or greater, such as 97%, 97.5%, 98%, 98.5%, 99%, 99.5%, 99.8% or 100% (w/w) of a single stereoisomer of a particular compound relative to the total weight of all the stereoisomers of the compound.

Exemplary Compounds

In certain embodiments, the disclosure relates to a compound of Formula I

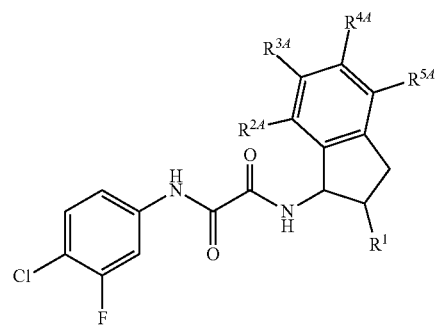

Formula I or a salt or solvate thereof, wherein

R$^1$ is

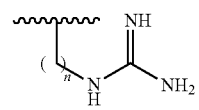

wherein n is 1;

R$^{2A}$ is H, optionally substituted alkylaminoalkyl, optionally substituted cycloalkylaminoalkyl, or

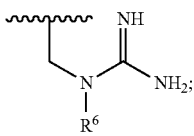

$R^{3A}$ is H, optionally substituted alkylaminoalkyl, optionally substituted cycloalkylaminoalkyl, or

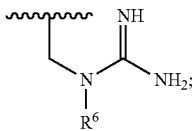

$R^{4A}$ is H, optionally substituted alkylaminoalkyl, optionally substituted cycloalkylaminoalkyl, or

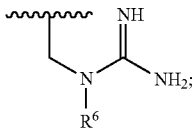

$R^{5A}$ is H, optionally substituted alkylaminoalkyl, optionally substituted cycloalkylaminoalkyl, or

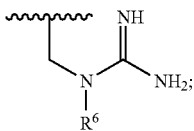

wherein $R^6$ is H, $C_{1-6}$alkyl, or $C_{3-8}$cycloalkyl;
provided at least one of $R^{2A}$, $R^{3A}$, $R^{4A}$, or $R^{5A}$ is optionally substituted alkylaminoalkyl, optionally substituted cycloalkylaminoalkyl, or

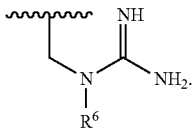

In some embodiments, $R^{2A}$ is H. In other embodiments, $R^{2A}$ is optionally substituted alkylaminoalkyl or optionally substituted cycloalkylaminoalkyl. In further embodiments, $R^{2A}$ is optionally substituted alkylaminoalkyl. In yet other embodiments, $R^{2A}$ is methylaminoalkyl, ethylaminoalkyl, propylaminoalkyl, for example, n-propylaminoalkyl, or i-propylaminoalkyl. In still further embodiments, $R^{2A}$ is optionally substituted alkylamino-$CH_2$—. In other embodiments, $R^{2A}$ is $CH_3$—NH—$CH_2$—. In yet further embodiments, $R^{2A}$ is $(CH_3)_2CH$—NH—$CH_2$—. In further embodiments, $R^{2A}$ is $CH_3$—N($CH_2$-phenyl)-$CH_2$—. In yet other embodiments, $R^{2A}$ is $CH_3$—N($CH_2CH_2$-phenyl)-$CH_2$—. In some embodiments, $R^{2A}$ is $CH_3$—N($CH_2COOH$)—$CH_2$—. In certain embodiments, $R^{2A}$ is optionally substituted cycloalkylaminoalkyl. In other embodiments, $R^{2A}$ is cyclopropylaminoalkyl. In further embodiments, $R^{2A}$ is cyclobutylaminoalkyl, cyclopentylaminoalkyl, or cyclohexylaminoalkyl. In yet other embodiments, $R^{2A}$ is cyclopropylamino-$CH_2$—, cyclobutylamino-$CH_2$—, cyclopentylamino-$CH_2$—, or cyclohexylamino-$CH_2$—.

In still further embodiments, $R^{2A}$ is

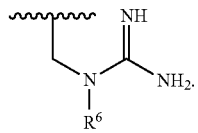

In these embodiments, $R^6$ can be H. In other embodiments, $R^6$ is $C_{1-6}$alkyl, for example, methyl, ethyl, or isopropyl. In further embodiments, $R^6$ is $C_{3-8}$cycloalkyl, for example, cyclopropyl.

In some embodiments, $R^{3A}$ is H. In other embodiments, $R^{3A}$ is optionally substituted alkylaminoalkyl or optionally substituted cycloalkylaminoalkyl. In further embodiments, $R^{3A}$ is optionally substituted alkylaminoalkyl. In yet other embodiments, $R^{3A}$ is methylaminoalkyl, ethylaminoalkyl, propylaminoalkyl, for example, n-propylaminoalkyl, or i-propylaminoalkyl. In still further embodiments, $R^{3A}$ is optionally substituted alkylamino-$CH_2$—. In other embodiments, $R^{3A}$ is $CH_3$—NH—$CH_2$—. In yet further embodiments, $R^{3A}$ is $(CH_3)_2CH$—NH—$CH_2$—. In further embodiments, $R^{3A}$ is $CH_3$—N($CH_2$-phenyl)-$CH_2$—. In yet other embodiments, $R^{3A}$ is $CH_3$—N($CH_2CH_2$-phenyl)-$CH_2$—. In some embodiments, $R^{3A}$ is $CH_3$—N($CH_2COOH$)—$CH_2$—. In certain embodiments, $R^{3A}$ is optionally substituted cycloalkylaminoalkyl. In other embodiments, $R^{3A}$ is cyclopropylaminoalkyl. In further embodiments, $R^{3A}$ is cyclobutylaminoalkyl, cyclopentylaminoalkyl, or cyclohexylaminoalkyl. In yet other embodiments, $R^{3A}$ is cyclopropylamino-$CH_2$—, cyclobutylamino-$CH_2$—, cyclopentylamino-$CH_2$—, or cyclohexylamino-$CH_2$—.

In still further embodiments, $R^{3A}$ is

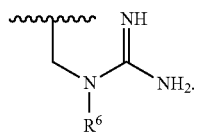

In these embodiments, $R^6$ can be H. In other embodiments, $R^6$ is $C_{1-6}$alkyl, for example, methyl, ethyl, or isopropyl. In further embodiments, $R^6$ is $C_{3-8}$cycloalkyl, for example, cyclopropyl.

In still further embodiments, $R^{4A}$ is H. In some embodiments, $R^{4A}$ is optionally substituted alkylaminoalkyl or optionally substituted cycloalkylaminoalkyl. In yet other embodiments, $R^{4A}$ is optionally substituted alkylaminoalkyl. In further embodiments, $R^{4A}$ is methylaminoalkyl, ethylaminoalkyl, propylaminoalkyl, for example, n-propylaminoalkyl, or i-propylaminoalkyl. In some embodiments, $R^{4A}$ is optionally substituted alkylamino-$CH_2$—. In yet further embodiments, $R^{4A}$ is $CH_3$—NH—$CH_2$— or $(CH_3)_2CH$—NH—$CH_2$—. In further embodiments, $R^{4A}$ is $CH_3$—N($CH_2$-phenyl)-$CH_2$—. In yet other embodiments, $R^{4A}$ is $CH_3$—N($CH_2CH_2$-phenyl)-$CH_2$—. In some embodiments, $R^{4A}$ is $CH_3$—N($CH_2COOH$)—$CH_2$—. In still other embodiments, $R^{4A}$ is optionally substituted cycloalkylaminoalkyl. In further embodiments, $R^{4A}$ is cyclopropylaminoalkyl, cyclobutylaminoalkyl, cyclopentylaminoalkyl, or cyclohexylaminoalkyl. In even further embodiments, $R^{4A}$ is cyclopropylamino-$CH_2$—, cyclobutylamino-$CH_2$—, cyclopentylamino-$CH_2$—, or cyclohexylamino-$CH_2$—.

In other embodiments, $R^{4A}$ is

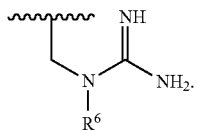

In these embodiments, $R^6$ can be H. In other embodiments, $R^6$ is $C_{1-6}$alkyl, for example, methyl, ethyl, or isopropyl. In further embodiments, $R^6$ is $C_{3-8}$cycloalkyl, for example, cyclopropyl.

In still further embodiments, $R^{5A}$ is H. In some embodiments, $R^{5A}$ is optionally substituted alkylaminoalkyl or optionally substituted cycloalkylaminoalkyl. In yet other embodiments, $R^{5A}$ is optionally substituted alkylaminoalkyl. In further embodiments, $R^{5A}$ is methylaminoalkyl, ethylaminoalkyl, propylaminoalkyl, for example, n-propylaminoalkyl, or i-propylaminoalkyl. In some embodiments, $R^{5A}$ is optionally substituted alkylamino-$CH_2$—. In yet further embodiments, $R^{5A}$ is $CH_3$—NH—$CH_2$— or $(CH_3)_2$CH—NH—$CH_2$—. In further embodiments, $R^{5A}$ is $CH_3$—N($CH_2$-phenyl)-$CH_2$—. In yet other embodiments, $R^{5A}$ is $CH_3$—N($CH_2CH_2$-phenyl)-$CH_2$—. In some embodiments, $R^{5A}$ is $CH_3$—N($CH_2COOH$)—$CH_2$—. In still other embodiments, $R^{5A}$ is optionally substituted cycloalkylaminoalkyl. In further embodiments, $R^{5A}$ is cyclopropylaminoalkyl, cyclobutylaminoalkyl, cyclopentylaminoalkyl, or cyclohexylaminoalkyl. In even further embodiments, $R^{5A}$ is cyclopropylamino-$CH_2$—, cyclobutylamino-$CH_2$—, cyclopentylamino-$CH_2$—, or cyclohexylamino-$CH_2$—.

In other embodiments, $R^{5A}$ is

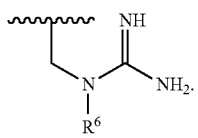

In these embodiments, $R^6$ can be H. In other embodiments, $R^6$ is $C_{1-6}$alkyl, for example, methyl, ethyl, or isopropyl. In further embodiments, $R^6$ is $C_{3-8}$cycloalkyl, for example, cyclopropyl.

In the compounds of Formula I, at least one of $R^{2A}$, $R^{3A}$, $R^{4A}$, or $R^{5A}$ is optionally substituted alkylaminoalkyl, optionally substituted cycloalkylaminoalkyl, or

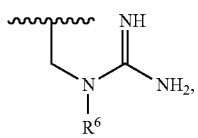

and wherein the remaining of $R^{2A}$, $R^{3A}$, $R^{4A}$, and $R^{5A}$ is H. Preferably, one of $R^{2A}$, $R^{3A}$, $R^{4A}$, or $R^{5A}$ is optionally substituted alkylaminoalkyl, optionally substituted cycloalkylaminoalkyl, or

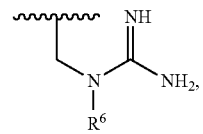

and wherein the remaining of $R^{2A}$, $R^{3A}$, $R^{4A}$, and $R^{5A}$ is H. In other embodiments, two of $R^{2A}$, $R^{3A}$, $R^{4A}$, or $R^{5A}$ is optionally substituted alkylaminoalkyl, optionally substituted cycloalkylaminoalkyl, or

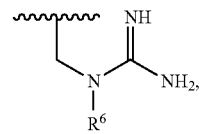

and wherein the remaining of $R^{2A}$, $R^{3A}$, $R^{4A}$, and $R^{5A}$ is H. In still other embodiments, three of $R^{2A}$, $R^{3A}$, $R^{4A}$, or $R^{5A}$ is optionally substituted alkylaminoalkyl, optionally substituted cycloalkylaminoalkyl, or

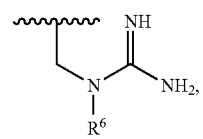

and wherein the remaining of $R^{2A}$, $R^{3A}$, $R^{4A}$, and $R^{5A}$ is H.

In exemplary embodiments, $R^{3A}$ is optionally substituted alkylaminoalkyl, optionally substituted cycloalkylaminoalkyl, or

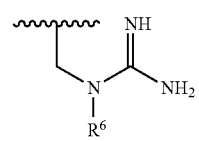

and $R^{2A}$, $R^{4A}$, and $R^{5A}$ are H. In these embodiments, $R^{3A}$ is preferably optionally substituted alkylaminoalkyl. In other embodiments, $R^{3A}$ is preferably

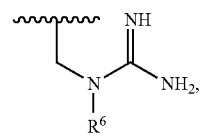

wherein $R^6$ is $C_{1-6}$alkyl, for example, methyl, ethyl, or isopropyl.

In exemplary embodiments, $R^{4A}$ is optionally substituted alkylaminoalkyl, optionally substituted cycloalkylaminoalkyl, or

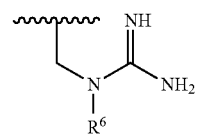

and $R^{2A}$, $R^{3A}$, and $R^{5A}$ are H. In these embodiments, $R^{4A}$ is preferably optionally substituted alkylaminoalkyl. In other embodiments, $R^{4A}$ is preferably

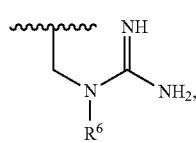

wherein $R^6$ is
$C_{1-6}$alkyl, for example, methyl, ethyl, or isopropyl.

Preferably, the compound of Formula I is provided as a single stereoisomer. In preferred embodiments, the compound of Formula I is stereochemically pure.

In yet further embodiments, the compound of Formula I is

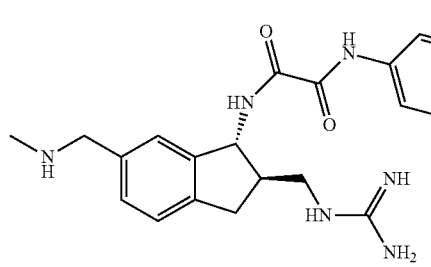

(+)-(R,R)-JP-III-048

In certain embodiments, the compound of Formula I is

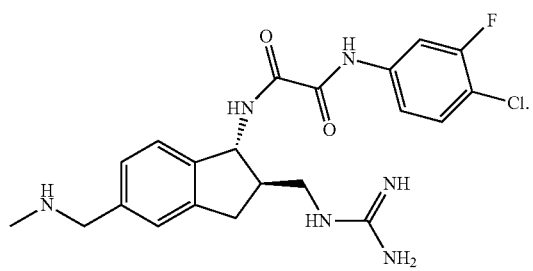

(+)-(R,R)-BNM-III-170

In other embodiments, the compound of Formula I is

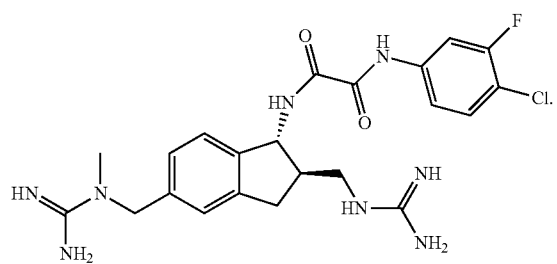

(+)-(R,R)-BNM-IV-147

In further embodiments, the compound of Formula I is

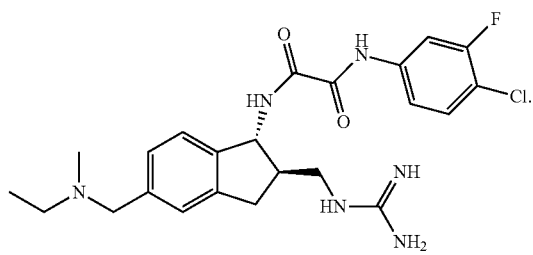

(R,R)-BNM-IV-114

In some embodiments, the compound of Formula I is

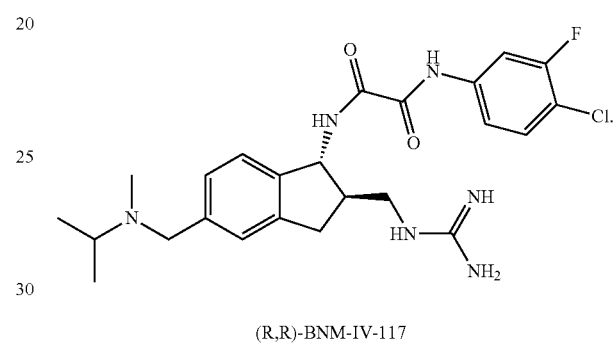

(R,R)-BNM-IV-117

In yet further embodiments, the compound of Formula I is

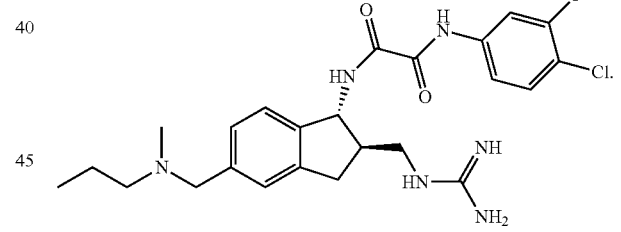

(R,R)-BNM-IV-123

In still other embodiments, the compound of Formula I is

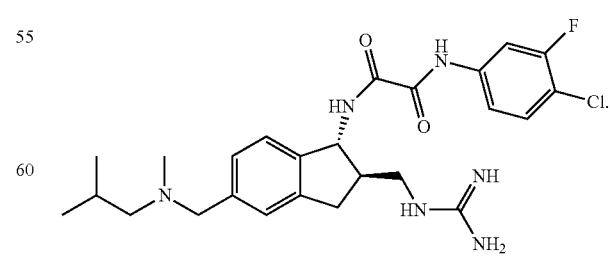

(R,R)-BNM-IV-124

In further embodiments, the compound of Formula I is

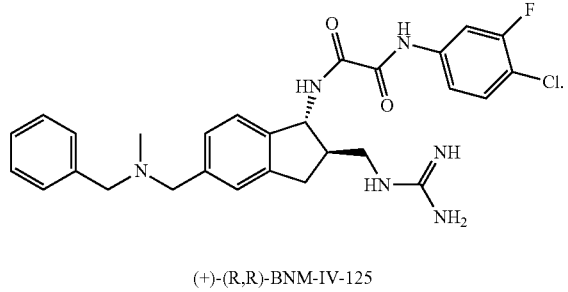 [SMILES: CN(Cc1ccccc1)Cc1ccc2c(c1)C[C@H](CNC(=N)N)[C@H]2NC(=O)C(=O)Nc1ccc(Cl)c(F)c1]

(+)-(R,R)-BNM-IV-125

In still further embodiments, the compound of Formula I is

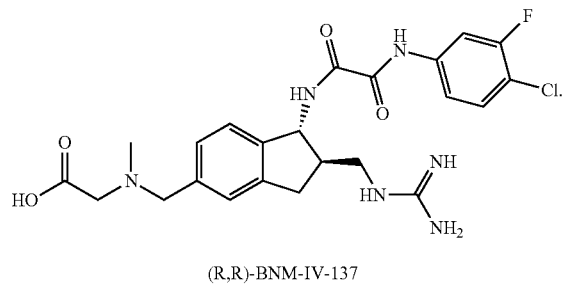 [SMILES: CN(CC(=O)O)Cc1ccc2c(c1)C[C@H](CNC(=N)N)[C@H]2NC(=O)C(=O)Nc1ccc(Cl)c(F)c1]

(R,R)-BNM-IV-137

In other embodiments, the compound of Formula I is

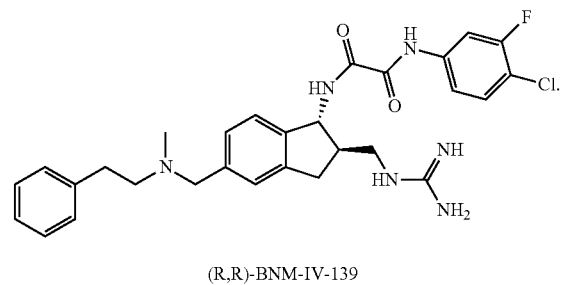 [SMILES: CN(CCc1ccccc1)Cc1ccc2c(c1)C[C@H](CNC(=N)N)[C@H]2NC(=O)C(=O)Nc1ccc(Cl)c(F)c1]

(R,R)-BNM-IV-139

In further embodiments, the compound of Formula I is

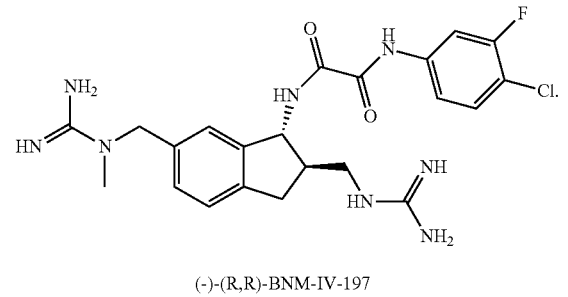 [SMILES: CN(Cc1ccc2c(c1)[C@H](NC(=O)C(=O)Nc1ccc(Cl)c(F)c1)[C@@H](CNC(=N)N)C2)C(=N)N]

(-)-(R,R)-BNM-IV-197

The disclosure is also directed to compounds of Formula II

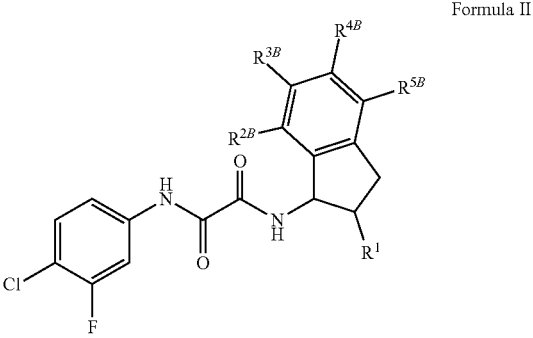

Formula II or a salt or solvate thereof,
wherein
R¹ is

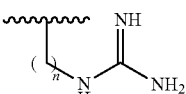

wherein n is 1;
$R^{2B}$ is H, bromo, or chloro;
$R^{3B}$ is H, bromo, or chloro;
$R^{4B}$ is H, bromo, or chloro;
$R^{5B}$ is H, bromo, or chloro;
provided at least one of $R^{2B}$, $R^{3B}$, $R^{4B}$, or $R^{5B}$ is bromo or chloro.

In some embodiments, $R^{2B}$ is H. In still further embodiments, $R^{2B}$ is bromo. In yet other embodiments, $R^{2B}$ is chloro.

In some embodiments, $R^{3B}$ is H. In still further embodiments, $R^{3B}$ is bromo. In yet other embodiments, $R^{3B}$ is chloro.

In some embodiments, $R^{4B}$ is H. In still further embodiments, $R^{4B}$ is bromo. In yet other embodiments, $R^{4B}$ is chloro.

In some embodiments, $R^{5B}$ is H. In still further embodiments, $R^{5B}$ is bromo. In yet other embodiments, $R^{5B}$ is chloro.

According to the disclosure, one of $R^{2B}$, $R^{3B}$, $R^{4B}$, and $R^{5B}$ is bromo or chloro and the remaining of $R^{2B}$, $R^{3B}$, $R^{4B}$, and $R^{5B}$ are H. In other embodiments, two of $R^{2B}$, $R^{3B}$, $R^{4B}$, and $R^{5B}$ is bromo or chloro and the remaining of $R^{2B}$, $R^{3B}$, $R^{4B}$, and $R^{5B}$ are H. In still other embodiments, three of $R^{2B}$, $R^{3B}$, $R^{4B}$, and $R^{5B}$ is bromo or chloro and the remaining of $R^{2B}$, $R^{3B}$, $R^{4B}$, and $R^{5B}$ are H.

In some embodiments, $R^{2B}$, $R^{4B}$, and $R^{5B}$ are H. In still other embodiments, $R^{4B}$ is H. In further embodiments, $R^{4B}$ is bromo or chloro. In yet other embodiments, $R^{2B}$, $R^{3B}$, and $R^{5B}$ are H.

In certain embodiments, the compound of Formula II is provided as a single stereoisomer. In preferred embodiments, the compound of Formula II is stereochemically pure. In certain embodiments, the compound described herein is the (R,R) enantiomer.

In certain embodiments, the compounds described herein are related to those described in International Patent Application Publication No. WO 13/090696, which is hereby incorporated by reference in its entirety.

Exemplary Methods

In certain embodiments, methods of activating HIV exterior envelope glycoprotein gp120 are provided and comprise contacting HIV with an effective amount of any one of the compounds described herein. In certain embodiments, methods of activating HIV exterior envelope glycoprotein gp120 are provided and comprise contacting HIV with an effective amount of a compound according to Formula I or Formula II.

In certain embodiments, methods of inhibiting transmission of HIV to a cell are provided and comprise the step of: contacting HIV with an effective amount of any one of the compounds described herein, thereby inhibiting transmission of HIV to said cell. In certain embodiments, methods of inhibiting transmission of HIV to a cell are provided and comprise contacting HIV with an effective amount of a compound according to Formula I or Formula II, thereby inhibiting transmission of HIV to said cell.

In certain embodiments, methods of inhibiting the progression of HIV infection in a cell are provided and comprise contacting HIV with an effective amount of any one of the compounds described herein, thereby inhibiting progression of HIV in the cell. In certain embodiments, methods of inhibiting the progression of HIV infection in a cell are provided and comprise contacting HIV with an effective amount of a compound according to Formula I or Formula II, thereby inhibiting progression of HIV in the cell.

In certain embodiments, methods of inhibiting the transmission or progression of HIV to a cell are provided and comprise:
contacting HIV with an effective amount of any one of the compounds described herein; and
contacting HIV with an effective amount of an exogenous ligand mimicking the chemokine receptor expressed on said cell.

In certain embodiments, methods of inhibiting the transmission or progression of HIV to a cell are provided and comprise:
contacting HIV with an effective amount of a compound according to Formula I or Formula II and
contacting HIV with an effective amount of an exogenous ligand mimicking the chemokine receptor expressed on said cell.

In certain embodiments, the compound binds to the HIV exterior envelope glycoprotein gp120.

In certain embodiments, the chemokine receptor is selected from CCR5 and CXCR4.

In certain embodiments, the HIV is HIV-1 or HIV-2.

In some embodiments, the compound interacts with gp120 Phe43. In other embodiments, the compound interacts with gp120 Asp368. In yet other embodiments, the compound interacts with gp120 Phe43 and gp120 Asp368.

In further embodiments, the cell is CD4-negative and CCR5-positive; and the compound does not efficiently activate HIV infection of the cell.

In other embodiments, methods of generating a protein binding domain that specifically binds to gp120 in a specific conformational state are provided and comprise:
a) contacting gp120 or a fragment thereof with a compound, wherein the compound is a compound of Formula I or Formula II, thereby forming gp120 in the specific conformational state; and
b) generating antibodies to gp120 in the specific conformation state, wherein optionally gp120 in the specific conformational state is bound to the compound.

In yet further embodiments, the protein binding domain is an antibody.

In certain embodiments, methods of neutralizing HIV-1 and provided and comprise:
contacting HIV-1 with an effective amount of a compound of Formula I or Formula II, thereby forming HIV-1 having gp120 in a specific conformational state; and
contacting the HIV-1 in the specific conformational state with an antibody, wherein optionally the HIV-1 in the specific conformational state is bound to the compound.

In certain embodiments, methods of treating or preventing HIV infection are provided and comprise:
administering to a subject in need thereof, a therapeutically effective amount of an antibody; and
co-administering to the subject an effective amount of a compound of Formula I or Formula II.

In certain embodiments, the antibody is a monoclonal antibody. In further embodiments, the antibody is a monoclonal antibody directed against CD4-induced (CD4i) epitopes or the V3 region. In yet other embodiments, the antibody is an anti-gp120 antibody.

In certain embodiments, the HIV is primary HIV-1 JR-FL or a transmitted/founder virus.

In other embodiments, the compound is (+)-(R,R)-JP-III-048. In further embodiments, the compound is (+)-(R,R)-BNM-III-170. In some embodiments, the compound is (+)-(R,R)-BNM-IV-147. In other embodiments, the compound is (+)-(R,R)-BNM-IV-114. In still further embodiments, the compound is (+)-(R,R)-BNM-IV-117. In certain embodiments, the compound is (+)-(R,R)-BNM-IV-123. In yet other embodiments, the compound is (+)-(R,R)-BNM-IV-124. In further embodiments, the compound is (+)-(R,R)-BNM-IV-125. In still some embodiments, the compound is (+)-(R,R)-BNM-IV-137. In yet other embodiments, the compound is (+)-(R,R)-BNM-IV-139. In still other embodiments, the compound is (−)-(R,R)-BNM-IV-197.

In certain embodiments, the compound is a single enantiomer. In certain embodiments, the compound is the (R,R) enantiomer.

In certain embodiments, the methods described herein are related to those described in International Patent Application Publication No. WO13/090696 and International Application No. PCT/US2015/015182, which are hereby incorporated by reference in their entireties.

For example, the disclosure relates to methods of immunizing an animal. In certain embodiments, antibodies may be generated that specifically bind to a conformational epitope of an active conformational state of gp120 by administering to a subject gp120 in the presence of any of the compounds described herein.

For the immunization of an animal with gp120, the gp120 may be produced and purified using conventional methods that may employ expressing a recombinant form of the gp120 in a host cell, and purifying the gp120 using affinity chromatography and/or antibody-based methods. In particular embodiments, the baculovirus/Sf-9 system may be employed for expression, although other expression systems (e.g., bacterial, yeast or mammalian cell systems) may also be used. Exemplary methods for expressing and purifying gp120s are described in the art. A gp120 may also be reconstituted in phospholipid vesicles. Likewise, methods for reconstituting an active gp120 in phospholipid vesicles are known. In certain cases, the gp120 and phospholipids may be reconstituted at high density (e.g., 1 mg receptor per mg of phospholipid). In particular embodiments, the phospholipids vesicles may be tested to confirm that the gp120 is active. In many cases, a gp120 may be present in the phospholipid vesicle in both orientations (in the normal orientation, and in the "upside down" orientation in which the intracellular loops are on the outside of the vesicle). Other immunization methods with gp120 include, without limitation, the use of complete cells expressing a gp120, vaccination with a nucleic acid sequence encoding a gp120 (e.g. DNA vaccination), immunization with viruses or virus like particles expressing a gp120, amongst others.

Any suitable animal, e.g., a warm-blooded animal, in particular a mammal such as a rabbit, mouse, rat, camel, sheep, cow, shark, or pig or a bird such as a chicken or turkey, may be immunized using any of the techniques well known in the art suitable for generating an immune response.

The screening for antibodies, as a non-limiting example, specifically binding to a conformational epitope of a functional conformational state of said gp120 may for example be performed by screening a set, collection or library of cells that express heavy chain antibodies on their surface, or bacteriophages, or by screening of a (naive or immune) library of peptide sequences, which may all be performed in a manner known per se, and which method may optionally further comprise one or more other suitable steps, such as, for example and without limitation, a step of affinity maturation, a step of expressing the desired amino acid sequence, a step of screening for binding and/or for activity against the desired antigen (in this case, the gp120), a step of determining the desired amino acid sequence or nucleotide sequence, a step of introducing one or more humanizing substitutions, a step of formatting in a suitable multivalent and/or multi-specific format, a step of screening for the desired biological and/or physiological properties (i.e. using a suitable assay known in the art), and/or any combination of one or more of such steps, in any suitable order.

Exemplary Complexes

In certain embodiments, the disclosure relates to a complex comprising (i) a compound of Formula I or Formula II, (ii) gp120 in a functional conformational state, and (iii) optionally, an antibody.

In certain embodiments, the disclosure relates to any of the complexes described herein, wherein said complex is in a solubilized form or immobilized to a solid support.

In certain embodiments, the disclosure relates to any of the complexes described herein, wherein the compound is depicted in Scheme 1, Scheme 2, Example 1, or Example 2, or a stereoisomer thereof, or a racemic mixture thereof.

In certain embodiments, the disclosure relates to any of the complexes described herein, wherein the compound is (+)-(R,R)-JP-III-048.

In certain embodiments, the disclosure relates to any of the complexes described herein, wherein the compound is (+)-(R,R)-BNM-III-170.

In other embodiments, the disclosure relates to any of the complexes described herein, wherein the compound dis (+)-(R,R)-BNM-IV-147.

In some embodiments, the disclosure relates to any of the complexes described herein, wherein the compound is (R,R)-BNM-IV-114.

In still further embodiments, the disclosure relates to any of the complexes described herein, wherein the compound is (R,R)-BNM-IV-117.

In certain embodiments, the disclosure relates to any of the complexes described herein, wherein the compound is (R,R)-BNM-IV-123.

In yet other embodiments, the disclosure relates to any of the complexes described herein, wherein the compound is (R,R)-BNM-IV-124.

In further embodiments, the disclosure relates to any of the complexes described herein, wherein the compound is (+)-(R,R)-BNM-IV-125.

In still some embodiments, the disclosure relates to any of the complexes described herein, wherein the compound is (R,R)-BNM-IV-137.

In yet other embodiments, the disclosure relates to any of the complexes described herein, wherein the compound is (R,R)-BNM-IV-139.

In fstill further embodiments, the disclosure relates to any of the complexes as described herein, wherein the compound is (−)-(R,R)-BNM-IV-197.

In certain embodiments, the disclosure relates to any of the complexes described herein, wherein the antibody is a monoclonal antibody.

In certain embodiments, the disclosure relates to any of the complexes described herein, wherein the antibody is a monoclonal antibody directed against CD4-induced (CD4i) epitopes or the V3 region.

In certain embodiments, the disclosure relates to any of the complexes described herein, wherein the antibody is an anti-gp120 antibody.

Exemplary Pharmaceutical Compositions

While it is possible for compounds described herein to be administered as the raw chemical, it is also possible to present them as a pharmaceutical formulation. Accordingly, pharmaceutical formulations are provided and comprise a compound or a pharmaceutically acceptable salt, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients can be used as suitable and as understood in the art; e.g., in Remington's Pharmaceutical Sciences. The pharmaceutical compositions can be manufactured in a manner that is itself known, e.g., by means of conventional mixing, dissolving, granulating, dragee-making, levigating, emulsifying, encapsulating, entrapping or compression processes, for example.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route depends upon for example the condition and disorder of the recipient. The formulations can conveniently be presented in unit dosage form and can be prepared by any of the methods well known in the art. All methods include the step of bringing into association a compound described herein or a salt (preferably a pharmaceutically acceptable salt), prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration can be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient can also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders, inert diluents, or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. The formulations can be presented in unit-dose or multi-dose containers, for example sealed ampoules and vials, and can be stored in powder form or in a freeze-dried (lyophilized) condition requiring only the addition of the sterile liquid carrier, for example, saline or sterile pyrogen-free water, immediately prior to use. Extemporaneous injection solutions and suspensions can be prepared from sterile powders, granules and tablets of the kind previously described.

Formulations for parenteral administration include aqueous and non-aqueous (oily) sterile injection solutions of the active compounds which can contain antioxidants, buffers, bacteriostats and solutes which render the formulation isotonic with the blood of the intended recipient; and aqueous and non-aqueous sterile suspensions which can include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compounds can also be formulated in rectal compositions such as suppositories or retention enemas, e.g., containing conventional suppository bases such as cocoa butter, polyethylene glycol, or other glycerides. The compounds can also be formulated in vaginal compositions as gels, suppositories, or as dendrimers conjugates. The compounds can be administered topically, that is by non-systemic administration. Formulations suitable for topical administration include liquid or semi-liquid preparations suitable for penetration through the skin such as gels, liniments, lotions, creams, ointments or pastes.

Gels for topical or transdermal administration of the compounds can include a mixture of volatile solvents, nonvolatile solvents, and water. The volatile solvent component of the buffered solvent system can include lower (C1-C6) alkyl alcohols, lower alkyl glycols and lower glycol polymers. In certain embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound can crystallize due to evaporation of volatile solvent, while an excess will result in a lack of bioavailability due to poor release of drug from solvent mixture. The buffer component of the buffered solvent system can be selected from any buffer commonly used in the art; in certain embodiments, water is used. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions or liniments for application to the skin can also include an agent to hasten drying and to cool the skin, such as an alcohol or acetone, and/or a moisturizer such as glycerol or an oil such as castor oil or arachis oil.

Creams, ointments or pastes are semi-solid formulations of the active ingredient for external application. They can be made by mixing the active ingredient in finely-divided or powdered form, alone or in solution or suspension in an aqueous or non-aqueous fluid, with the aid of suitable machinery, with a greasy or non-greasy base. The base can comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation can incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, can also be included.

Embodiments:

Embodiment 1. A compound of Formula I

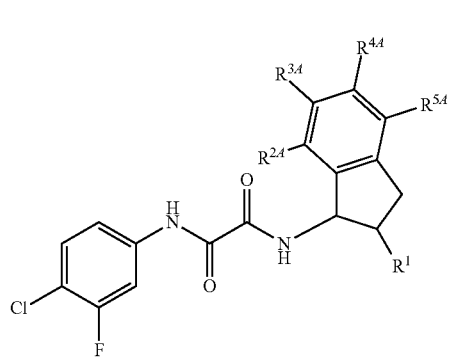

Formula I or a pharmaceutically acceptable salt or solvate thereof, wherein, independently for each occurrence, $R^1$ is

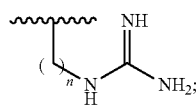

$R^{2A}$ is —H, alkylaminoalkyl, or cycloalkylaminoalkyl;
$R^{3A}$ is —H, alkylaminoalkyl, or cycloalkylaminoalkyl;
$R^{4A}$ is —H, alkylaminoalkyl, or cycloalkylaminoalkyl;
$R^{5A}$ is —H, alkylaminoalkyl, or cycloalkylaminoalkyl;
provided at least one of $R^{2A}$, $R^{3A}$, $R^{4A}$, or $R^{5A}$ is not —H; and
n is 1.

Embodiment 2. The compound of Embodiment 1, wherein $R^{3A}$ is alkylaminoalkyl or cycloalkylaminoalkyl.

Embodiment 3. The compound of Embodiment 1, wherein $R^{3A}$ is alkylaminoalkyl.

Embodiment 4. The compound of Embodiment 1, wherein $R^{3A}$ is methylaminoalkyl.

Embodiment 5. The compound of Embodiment 1, wherein $R^{3A}$ is ethylaminoalkyl.

Embodiment 6. The compound of Embodiment 1, wherein $R^{3A}$ is propylaminoalkyl, for example, n-propylaminoalkyl or i-propylaminoalkyl.

Embodiment 7. The compound of Embodiment 1, wherein $R^{3A}$ is alkylamino-$CH_2$—.

Embodiment 8. The compound of Embodiment 1, wherein $R^{3A}$ is $CH_3$—NH—$CH_2$—.

Embodiment 9. The compound of Embodiment 1, wherein $R^{3A}$ is $(CH_3)_2CH$—NH—$CH_2$—.

Embodiment 10. The compound of Embodiment 1, wherein $R^{3A}$ is cycloalkylaminoalkyl.

Embodiment 11. The compound of Embodiment 1, wherein $R^{3A}$ is cyclopropylaminoalkyl.

Embodiment 12. The compound of Embodiment 1, wherein $R^{3A}$ is cyclobutylaminoalkyl.

Embodiment 13. The compound of Embodiment 1, wherein $R^{3A}$ is cyclopentylaminoalkyl.

Embodiment. The compound of Embodiment 1, wherein $R^{3A}$ is cyclohexylaminoalkyl.

Embodiment 15. The compound of Embodiment 1, wherein $R^{3A}$ is cyclopropylamino-$CH_2$—.

Embodiment 16. The compound of Embodiment 1, wherein $R^{3A}$ is cyclobutylamino-$CH_2$—.

Embodiment 17. The compound of Embodiment 1, wherein $R^{3A}$ is cyclopentylamino-$CH_2$—.

Embodiment 18. The compound of Embodiment 1, wherein $R^{3A}$ is cyclohexylamino-$CH_2$—.

Embodiment 19. The compound of any one of Embodiments 1-18, wherein $R^{2A}$, $R^{4A}$, and $R^{5A}$ are —H.

Embodiment 20. The compound of Embodiment 1, wherein $R^{4A}$ is alkylaminoalkyl or cycloalkylaminoalkyl.

Embodiment 21. The compound of Embodiment 1, wherein $R^{4A}$ is alkylaminoalkyl.

Embodiment 22. The compound of Embodiment 1, wherein $R^{4A}$ is methylaminoalkyl.

Embodiment 23. The compound of Embodiment 1, wherein $R^{4A}$ is ethylaminoalkyl.

Embodiment 24. The compound of Embodiment 1, wherein $R^{4A}$ is propylaminoalkyl, for example, n-propylaminoalkyl or i-propylaminoalkyl.

Embodiment 25. The compound of Embodiment 1, wherein $R^{4A}$ is alkylamino-$CH_2$—.

Embodiment 26. The compound of Embodiment 1, wherein $R^{4A}$ is $CH_3$—NH—$CH_2$—.

Embodiment 27. The compound of Embodiment 1, wherein $R^{4A}$ is $(CH_3)_2CH$—NH—$CH_2$—.

Embodiment 28. The compound of Embodiment 1, wherein $R^{4A}$ is cycloalkylaminoalkyl.

Embodiment 29. The compound of Embodiment 1, wherein $R^{4A}$ is cyclopropylaminoalkyl.

Embodiment 30. The compound of Embodiment 1, wherein $R^{4A}$ is cyclobutylaminoalkyl.

Embodiment 31. The compound of Embodiment 1, wherein $R^{4A}$ is cyclopentylaminoalkyl.

Embodiment 32. The compound of Embodiment 1, wherein $R^{4A}$ is cyclohexylaminoalkyl.

Embodiment 33. The compound of Embodiment 1, wherein $R^{4A}$ is cyclopropylamino-$CH_2$—.

Embodiment 34. The compound of Embodiment 1, wherein $R^{4A}$ is cyclobutylamino-$CH_2$—.

Embodiment 35. The compound of Embodiment 1, wherein $R^{4A}$ is cyclopentylamino-$CH_2$—.

Embodiment 36. The compound of Embodiment 1, wherein $R^{4A}$ is cyclohexylamino-$CH_2$—.

Embodiment 37. The compound of any one of Embodiments 1 or 20-36, wherein $R^{2A}$, $R^{3A}$, and $R^{5A}$ are —H.

Embodiment 38. The compound of any one of Embodiments 1-37, wherein the compound is a single enantiomer.

Embodiment 39. The compound of Embodiment 38, wherein the compound is the (R,R) enantiomer.

Embodiment 40. The compound of Embodiment 1, wherein the compound is (+)-(R,R)-JP-III-048.

Embodiment 41. The compound of Embodiment 1, wherein the compound is (+)-(R,R)-BNM-III-170.

Embodiment 42. A compound of Formula II

Formula II

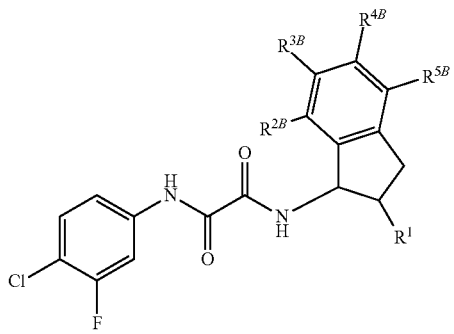

or a pharmaceutically acceptable salt or solvate thereof, wherein, independently for each occurrence,
R$^1$ is

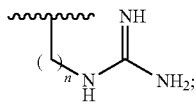

R$^{2B}$ is H, bromo, or chloro;
R$^{3B}$ is H, bromo, or chloro;
R$^{4B}$ is H, bromo, or chloro;
R$^{5B}$ is H, bromo, or chloro;
provided at least one of R$^{2B}$, R$^{3B}$, R$^{4B}$, or R$^{5B}$ is not —H; and
n is 1.

Embodiment 43. The compound of Embodiment 42, wherein R$^{3B}$ is bromo or chloro.

Embodiment 44. The compound of Embodiment 42, wherein R$^{3B}$ is bromo.

Embodiment 45. The compound of Embodiment 42, wherein R$^{3B}$ is chloro.

Embodiment 46. The compound of any one of Embodiments 42-45, wherein R$^{2B}$, R$^{4B}$, and R$^{5B}$ are H.

Embodiment 47. The compound of Embodiment 42, wherein R$^{4B}$ is bromo or chloro.

Embodiment 48. The compound of Embodiment 42, wherein R$^{4B}$ is bromo.

Embodiment 49. The compound of Embodiment 42, wherein R$^{4B}$ is chloro.

Embodiment 50. The compound of any one of Embodiments 42 or 47-49, wherein R$^{2B}$, R$^{3B}$, and R$^{5B}$ are H.

Embodiment 51. The compound of any one of Embodiments 42-50, wherein the compound is a single enantiomer.

Embodiment 52. The compound of Embodiment 51, wherein the compound is the (R,R) enantiomer.

Embodiment 53. A compound depicted in Scheme 1, Scheme 2, Example 1, or Example 2, or a stereoisomer thereof, or a racemic mixture thereof.

Embodiment 54. A method of activating HIV exterior envelope glycoprotein gp120 comprising the step of: contacting HIV with an effective amount of a compound of any one of Embodiments 1-52.

Embodiment 55. A method of inhibiting transmission of HIV to a cell comprising the step of: contacting HIV with an effective amount of a compound of any one of Embodiments 1-52, thereby inhibiting transmission of HIV to said cell.

Embodiment 56. A method of inhibiting the progression of HIV infection in a cell comprising the step of: contacting HIV with an effective amount of a compound of any one of Embodiments 1-52, thereby inhibiting progression of HIV in the cell.

Embodiment 57. A method of inhibiting the transmission or progression of HIV to a cell comprising the steps of:

contacting HIV with an effective amount of a compound of any one of Embodiments 1-52 and contacting HIV with an effective amount of an exogenous ligand mimicking the chemokine receptor expressed on said cell.

Embodiment 58. A method of generating a protein binding domain that specifically binds to gp120 in a specific conformational state, the method comprising the steps of:

a) contacting gp120 or a fragment thereof with a compound, wherein the compound is a compound of any one of Embodiments 1-52, thereby forming gp120 in the specific conformational state; and b) generating antibodies to gp120 in the specific conformation state, wherein optionally gp120 in the specific conformational state is bound to the compound.

Embodiment 59. The method of Embodiment 58, wherein the protein binding domain is an antibody.

Embodiment 60. A method of neutralizing HIV-1, the method comprising the step of:

contacting HIV-1 with an effective amount of a compound of any one of Embodiments 1-52, thereby forming HIV-1 having gp120 in a specific conformational state; and contacting the HIV-1 in the specific conformational state with an antibody, wherein optionally the HIV-1 in the specific conformational state is bound to the compound.

Embodiment 61. A method of treating or preventing HIV infection, the method comprising the step of:

administering to a subject in need thereof, a therapeutically effective amount of an antibody; and co-administering to the subject an effective amount of a compound of any one of Embodiments 1-52.

Embodiment 62. The method of any one of Embodiments 58-61, wherein the antibody is a monoclonal antibody.

Embodiment 63. The method of any one of Embodiments 58-61, wherein the antibody is a monoclonal antibody directed against CD4-induced (CD4i) epitopes or the V3 region.

Embodiment 64. The method of any one of Embodiments 58-61, wherein the antibody is an anti-gp120 antibody.

Embodiment 65. A complex comprising (i) a compound of any one of Embodiments 1-52, (ii) gp120 in a functional conformational state, and (iii) optionally, an antibody.

Embodiment 66. The complex of Embodiment 65, wherein said complex is in a solubilized form or immobilized to a solid support.

Embodiment 67. The complex of Embodiment 65 or 66, wherein the antibody is a monoclonal antibody.

Embodiment 68. The complex of Embodiment 65 or 66, wherein the antibody is a monoclonal antibody directed against CD4-induced (CD4i) epitopes or the V3 region.

Embodiment 69. The complex of Embodiment 65 or 66, wherein the antibody is an anti-gp120 antibody.

EXEMPLIFICATION

This disclosure is further illustrated by the following examples, which should not be construed as limiting.

General Information

All reactions were conducted in oven-dried glassware under an inert atmosphere of nitrogen or argon, unless otherwise stated. All solvents were reagent or high performance liquid chromatography (HPLC) grade. Anhydrous $CH_2Cl_2$ and THF were obtained from the Pure Solve™ PS-400 system under an argon atmosphere. All reagents were purchased from commercially available sources and used as received. Microwave heating was conducted with a Biotage Initiator system equipped with an autosampling arm, using either 0.5-2.0 mL, 2.0-5.0 mL, or 20-mL sealed reaction vials. Reactions were magnetically stirred under a nitrogen atmosphere, unless otherwise noted and reactions were monitored by either thin layer chromatography (TLC) with 0.25 mm E. Merck pre-coated silica gel plates or analytical high performance liquid chromatography (HPLC). Yields refer to chromatographically and spectroscopically pure compounds. Optical rotations were measured on a JASCO P-2000 polarimeter. Proton ($^1$H) and carbon ($^{13}$C) NMR spectra were recorded on a Bruker Avance III 500 MHz at 305 K. Chemical shifts (δ) are reported in parts per million (ppm) relative to chloroform (δ 7.26), methanol (δ 3.31), or dimethyl sulfoxide (δ 2.50) for $^1$H NMR, and chloroform (δ 77.0), methanol (δ 49.2), or dimethyl sulfoxide (δ 39.4) for $^{13}$C NMR. High-resolution mass spectra (HRMS) were recorded at the University of Pennsylvania Mass Spectroscopy Service Center on either a VG Micromass 70/70H or VG ZAB-E spectrometer. Analytical HPLC was preformed with a Waters HPLC-MS system, consisting of a 515 pump and Sunfire C18 reverse phase column (20 µL injection volume, 5 µm packing material, 4.5×50 mm column dimensions) with detection accomplished by a Micromass ZQ mass spectrometer and 2996 PDA detector. Preparative scale HPLC was preformed with a Gilson 333/334 preparative pump system equipped with a 5 mL injection loop, Sunfire C18 OBD column (5 µm packing material, 19×100 mm column dimensions) equipped with a UV-Vis dual wavelength (210 and 254 nm) detector and 215 liquid handling module. Solvent systems were comprised of $H_2O$ containing 0.1% formic acid, and acetonitrile. SFC purifications and analyses were performed with a JASCO system equipped with a Chiralpak AS-H column (10 mm×250 mm), a PU-280-$CO_2$ plus $CO_2$ Delivery System, a CO-2060 plus Intelligent Column Thermostat, an HC-2068-01 Heater Controller, a BP-2080 plus Automatic Back Pressure Regulator, an MD-2018 plus Photodiode Array Detector (200-648 nm), and PU-2080 plus Intelligent HPLC Pumps. Lyophilization was performed in a Labconco FreeZone 12 Plus lyophilizer (0.035 mbar). The purity of new compounds was judged by NMR and LCMS (>95%). Elemental analysis was outsourced to the Robertson Microlit Laboratories (Ledgewood, N.J. 07852).

Example 1

Preparation of JP-III-048

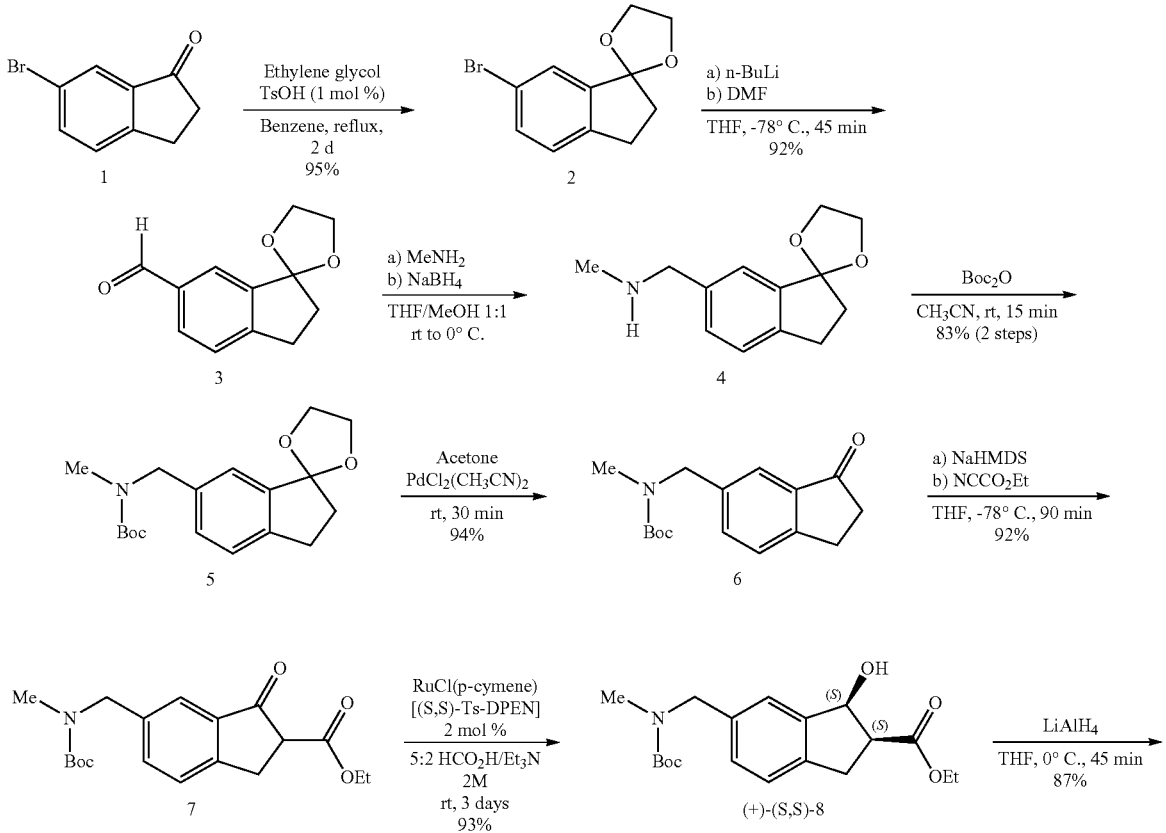

-continued
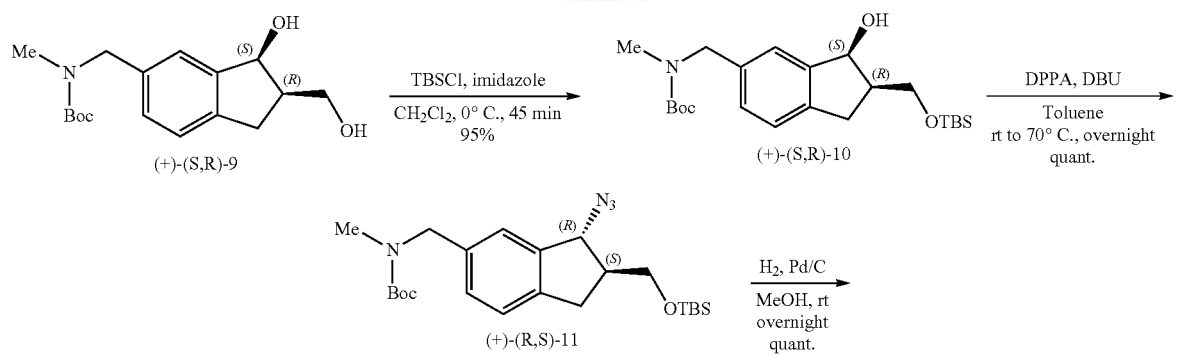
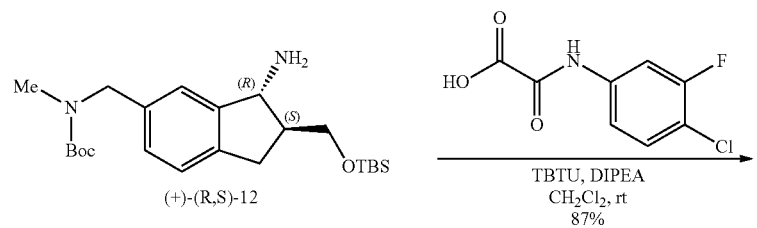
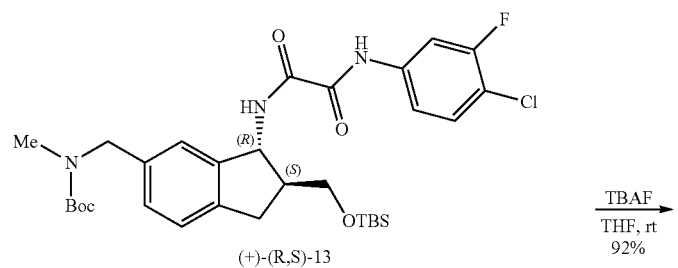
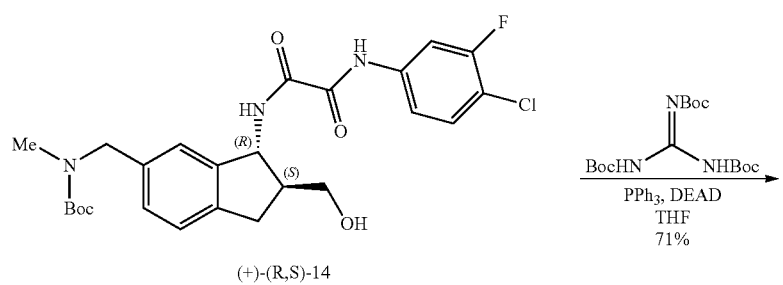
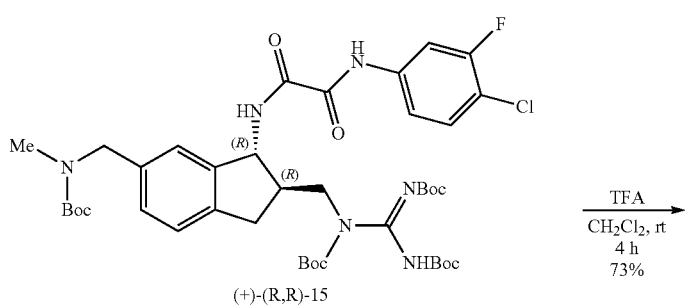

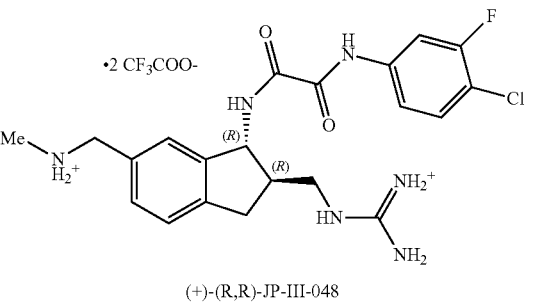

(+)-(R,R)-JP-III-048

Overall: 15 steps, 20% yield
Maximum amount prepared in one run: 256 mg

A. 6'-bromo-2',3'-dihydrospiro[[1,3]dioxolane-2,1'-indene] (2)

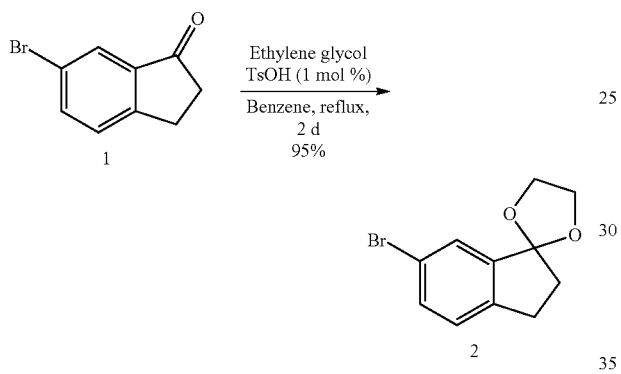

To a solution of 6-bromo-2,3-dihydro-1H-inden-1-one 1 (5 g, 23.69 mmol) in benzene (158 mL) were added ethane-1,2-diol (26.4 mL, 474 mmol) and tosic acid (0.045 g, 0.237 mmol). The flask was fitted with a Dean-Stark apparatus pre-filled with benzene and a reflux condenser and heated to 115° C. over 48 h. The reaction mixture was diluted with EtOAc and neutralized with sat. aq. NaHCO$_3$. Layers were separated and the resulting aqueous layer was extracted with EtOAc. The combined organic layers were dried over anhydrous Na$_2$SO$_4$ and concentrated in vacuo. Flash column chromatography (SiO$_2$, 95:5 hexanes/EtOAc) afforded 2 as a clear, pale yellow oil (5.73 g, 95%).

$^1$H NMR (500 MHz, CDCl$_3$) δ 7.47 (d, J=1.8 Hz, 1 H), 7.84 (dd, J=8.0, 1.8 Hz, 1 H), 7.11 (d, J=8.0 Hz, 1 H), 4.15-4.20 (m, 2 H), 4.06-4.11 (m, 2 H), 2.89 (t, J=7.0 Hz, 2 H), 2.30 (t, J=7.0 Hz, 2 H); $^{13}$C NMR (125 MHz, CDCl$_3$) δ 144.5, 142.7, 132.7, 126.9, 126.6, 120.6, 116.9, 65.5, 37.5, 28.3; HRMS (ES+) m/z=253.9947 ([M]$^+$; calcd for C$_{11}$H$_{11}$BrO$_2$: 253.9942).

B. 2',3'-dihydrospiro[[1,3]dioxolane-2,1'-indene]-6'-carbaldehyde (3)

To a precooled (–78° C.) solution of 2 (5.73 g, 22.46 mmol) in THF (32.1 mL) was slowly added butyllithium (9.88 mL of a 2.5 M solution in hexane, 24.71 mmol). The reaction mixture was stirred at –78° C. for 10 min, then N,N-dimethylformamide (2.078 mL, 27.0 mmol) was added. The resulting mixture was stirred at –78° C. for an additional 15 min, then allowed to warm to rt and stirred for a final 30 min. The reaction was quenched with sat. aq. NaHCO$_3$ and diluted with EtOAc. The combined organic layers were washed with water and brine, dried over anhydrous Na$_2$SO$_4$ and concentrated in vacuo. Flash column chromatography (SiO$_2$, 5:1 hexanes/EtOAc) afforded 3 as a clear orange oil (4.61 g, 92%).

$^1$H NMR (500 MHz, CDCl$_3$) δ 10.0 (s, 1 H), 7.87 (s, 1 H), 7.84 (dd, J=7.8, 1.3 Hz, 1 H), 7.39 (d, J=7.8 Hz, 1 H), 4.21-4.25 (m, 2 H), 4.10-4.15 (m, 2 H), 3.02 (t, J=7.0 Hz, 2 H), 2.36 (t, J=7.0 Hz, 2 H); $^{13}$C NMR (125 MHz, CDCl$_3$) δ 192.0, 151.2, 143.6, 136.1, 131.5, 126.0, 125.0, 116.5, 65.6, 37.3, 29.1; HRMS (ES+) m/z=204.0785 ([M]$^+$; calcd for C$_{12}$H$_{12}$O$_3$: 204.0786).

C. tert-butyl ((2',3'-dihydrospiro[[1,3]dioxolane-2,1'-inden]-6'-yl)methyl)(methyl)carbamate (5)

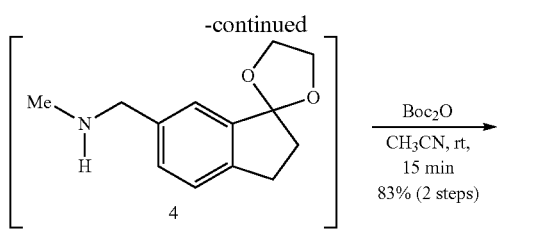

At 0° C., methylamine (41.5 ml of a 2 M solution in THF, 83 mmol) was added to 3 (neat, 4.61 g, 20.77 mmol). The reaction was warmed to rt and stirred for 30 min, then cooled to 0° C. MeOH (41.5 ml) was then added, followed by sodium borohydride (0.393 g, 10.38 mmol). The resulting mixture was stirred at 0° C. for 40 min. A second portion of sodium borohydride (0.393 g, 10.38 mmol) was then added. The reaction mixture was stirred for an additional 40 min, then quenched with water and extracted with EtOAc. The combined organic layers were washed with brine, dried over Na$_2$SO$_4$ and concentrated in vacuo. The resulting crude amine (4) was dissolved in acetonitrile (83 mL) and added to a solution of Boc$_2$O (5.30 mL, 22.85 mmol) in acetonitrile (83 mL). The mixture was stirred at rt for 15 min, then concentrated in vacuo. Flash column chromatography (SiO$_2$, 95:5 to 70:30 hexanes/EtOAc) afforded 5 as a clear colorless oil (5.48 g, 83%).

$^1$H NMR (500 MHz, CDCl$_3$) δ 7.10-7.17 (m, 3 H), 4.34 (s, 2 H), 4.05-4.11 (m, 2 H), 3.96-4.00 (m, 2 H), 2.84 (t, J=6.8 Hz, 2 H), 2.69-2.76 (2 br s, 3 H, rotamer 1 and 2), 2.21 (t, J=7.0 Hz, 2 H), 1.42 (s, 9 H); $^{13}$C NMR (125 MHz, CDCl$_3$, mixture of rotamers) δ 155.9, 155.5, 142.5, 142.3, 136.7, 129.1, 128.4, 125.0, 122.4, 121.8, 116.8, 79.4, 65.1, 64.9, 52.3, 51.6, 37.1, 33.6, 28.3, 28.0; HRMS (ES+) m/z=319.1798 ([M]$^+$; calcd for C$_{18}$H$_{25}$NO$_4$: 319.1784).

D. tert-butyl ((2',3'-dihydrospiro[[1,3]dioxolane-2, 1'-inden]-6'-yl)methyl)(methyl)carbamate (6)

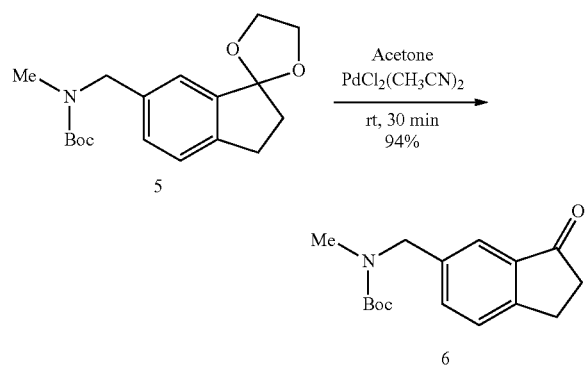

To a solution of 5 (5.47 g, 17.13 mmol) in acetone (171 mL) was added bis(acetonitrile)-palladium(II) dichloride (0.089 g, 0.343 mmol). The reaction mixture was stirred at rt for 30 min then concentrated in vacuo. The resulting residue was taken up in EtOAc (150 mL) and washed with sat. aq. NaHSO$_3$ (20 mL×3). The combined organic layers were dried over anhydrous Na$_2$SO$_4$ and concentrated in vacuo. Flash column chromatography (SiO$_2$, 85:15 to 70:30 hexanes/EtOAc) afforded 6 as a clear colorless oil that, upon standing, precipitated to form a white solid (4.67 g, 94%).

$^1$H NMR (500 MHz, CDCl$_3$) δ 7.54 (s, 1 H), 7.39-7.41 (m, 2 H), 4.42 (s, 2 H), 3.07 (t, J=5.5 Hz, 2 H), 2.76-2.78 (2 br s, 3 H, rotamer 1 and 2), 2.64 (t, J=6.0 Hz, 2 H), 1.43 (s, 9 H); $^{13}$C NMR (125 MHz, CDCl$_3$, mixture of rotamers) δ 206.8, 156.2, 155.6, 154.4, 137.8, 137.4, 134.4, 133.9, 127.0, 122.4, 80.0, 52.4, 51.6, 36.6, 34.1, 28.5, 25.6; HRMS (ES+) m/z=298.1434 ([M+Na]$^+$; calcd for C$_{16}$H$_{21}$NO$_3$Na: 298.1419).

E. (±)-ethyl 6-(((tert-butoxycarbonyl)(methyl) amino)methyl)-1-oxo-2,3-dihydro-1H-indene-2-carboxylate (7)

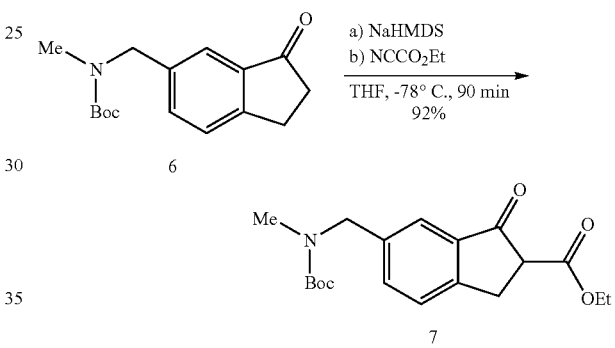

To a precooled (−78° C.) solution of 6 (1.45 g, 5.27 mmol) in THF (52.7 mL) was slowly added NaHMDS (10.53 mL of a 1 M solution in THF, 10.53 mmol). The mixture was stirred at −78° C. for 10 min, then ethyl carbonocyanidate (0.671 mL, 6.85 mmol) was added and stirring was continued at −78° C. for 1 h. The reaction was quenched with sat. aq. NH$_4$Cl and diluted with EtOAc. Layers were separated and the resulting aqueous layer was extracted with EtOAc. The combined organic layers were washed with brine, dried over Na$_2$SO$_4$ and concentrated in vacuo. Flash column chromatography (SiO$_2$, 85:15 hexanes/EtOAc) afforded (±)-7 as a clear purple oil (1.75 g, 92%).

$^1$H NMR (500 MHz, CDCl$_3$) δ 10.34 (s, enol OH), 7.52 (s, ketoester 1 H), 7.45-7.55 (m, ketoester 2 H), 7.15-7.30 (m, enol 3 H), 4.38 (br s, ketoester 2 H and enol 2 H), 4.22 (q, J=7.2 Hz, enol 2 H), 4.11-4.17 (m, ketoester 2 H), 3.64 (dd, J=8.3, 3.8 Hz, ketoester 1 H), 3.43 (dd, J=17.3, 3.3 Hz, ketoester 1 H), 3.39 (s, enol 2 H), 3.27 (dd, J=17.3, 8.3 Hz, ketoester 1 H), 2.71-2.75 (2 br s, ketoester 3 H and enol 3 H, rotamer 1 and 2), 1.39 (s, ketoester 9 H and enol 9 H), 1.26 (t, J=7.0 Hz, enol 3 H), 1.21 (t, J=7.0 Hz, ketoester 3 H); $^{13}$C NMR (125 MHz, CDCl$_3$, mixture of rotamers+enol) δ 199.3, 169.3, 169.0, 156.1, 155.5, 152.8, 142.2, 138.3, 137.3, 137.0, 135.5, 135.1, 134.5, 128.9, 128.4, 126.8, 124.8, 123.0, 119.7, 119.5, 102.9, 79.8, 61.6, 60.0, 53.6, 52.1, 51.4, 34.0, 33.9, 32.2, 30.0, 28.4, 14.4, 14.1; HRMS (ES+) m/z=370.1641 ([M+Na]$^+$; calcd for C$_{19}$H$_{25}$NO$_5$Na: 370.1630).

F. (1S,2S)-ethyl 6-(((tert-butoxycarbonyl)(methyl)amino)methyl)-1-hydroxy-2,3-dihydro-1H-indene-2-carboxylate (8)

G. tert-butyl (((2R,3S)-3-hydroxy-2-(hydroxymethyl)-2,3-dihydro-1H-inden-5-yl)methyl)(methyl)carbamate (9)

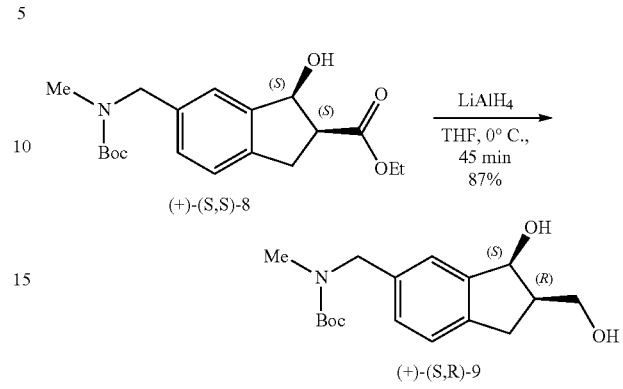

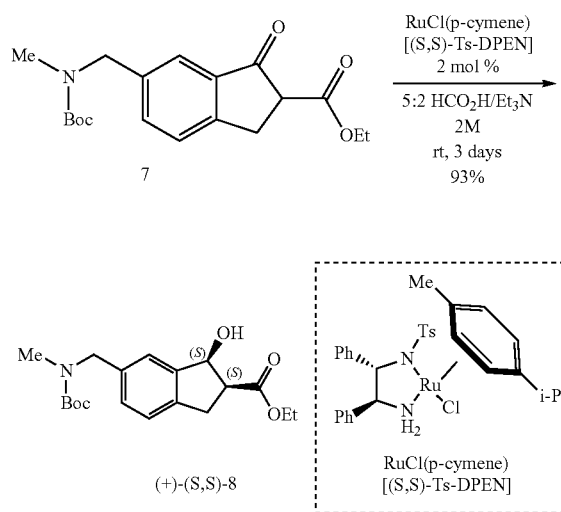

RuCl(p-cymene)[(S,S)-Ts-DPEN] (0.163 g, 0.256 mmol) was added in one portion to a solution of (±)-7 (5.13 g, 14.77 mmol) in HCOOH/Et$_3$N (5:2, 7.38 mL). The reaction mixture was stirred at room temperature for 3 days, diluted with CH$_2$Cl$_2$ and washed with H$_2$O (×2). The combined organic layers were dried over Na$_2$SO$_4$ and concentrated in vacuo. Flash column chromatography (SiO$_2$, hexanes/EtOAc 7:3) afforded (+)-8 as a clear pale pink oil (4.80 g, 93%). Enantiomeric excess determined by SFC by comparison with (R,R)-isomer and racemate: 98%. Method: column: Chiralpak AS-H; eluent: 30% MeOH in supercritical CO$_2$; flow rate: 4 mL/min; pressure: 12 MPa. Retention times: (+)-(S,S)-8: 0.9 min, (−)-(R,R)-8: 1.2 min.

$^1$H NMR (500 MHz, CDCl$_3$) δ 7.30 (br s, 1 H), 7.25-7.20 (m, 1 H), 7.17 (br s, 1 H), 5.35-5.30 (m, 1 H), 4.42 (br s, 2 H), 4.25 (q, J=7.1 Hz, 2 H), 3.45-3.36 (m, 2 H), 3.14-2.95 (m, 1 H), 2.95-2.75 (m, 3 H), 1.53-1.44 (m, 9 H), 1.32 (t, J=7.1 Hz, 3 H); $^{13}$C NMR (125 MHz, CDCl$_3$, mixture of rotamers) δ 173.1, 143.1, 140.8, 137.3, 124.9, 75.7, 60.9, 49.6, 33.9, 32.6, 28.5, 14.2; HRMS (ES+) m/z=372.1789 ([M+Na]$^+$; calcd for C$_{19}$H$_{27}$NO$_5$Na: 372.1787); [α]$_D$$^{14}$ +23.7 (c 1.13, CH$_2$Cl$_2$).

(−)-8: data consistent with (+)-isomer-[α]$_D$$^{22}$ −25.8 (c 1.67, CH$_2$Cl$_2$).

Enantiomeric excess determined by SFC (see table below):

| Enantiomer | (+)-(S,S)-8 | (−)-(R,R)-8 |
| --- | --- | --- |
| er | 99:1 | 98:2 |

Method: column: Chiralpak AS-H; eluent: 30% MeOH in supercritical CO$_2$; flow rate: 4 mL/min; pressure: 12 MPa. Retention times: (+)-(S,S)-8: 0.9 min, (−)-(R,R)-8: 1.2 min.

To a precooled (0° C.) suspension of lithium aluminum hydride (0.336 g, 8.84 mmol) in THF (10 mL) was added dropwise over 5 min via cannula a solution of (+)-8 (1.03 g, 2.95 mmol) in THF (20 mL). The reaction was stirred for 30 min at 0° C. then quenched with 15% aq. sodium potassium tartrate and stirred at rt for an additional 10 min. Water was added, followed by EtOAc. The resulting biphasic mixture was filtered through Celite, rinsing with abundant water and EtOAc. The layers were separated and the resulting aqueous layer was extracted with EtOAc. The combined organic layers were dried over Na$_2$SO$_4$ and concentrated in vacuo. Flash chromatography (SiO$_2$, 1:1 to 0:1 hexanes/EtOAc) afforded (+)-9 as a clear colorless oil (840 mg, 87%).

$^1$H NMR (500 MHz, CDCl$_3$) δ 7.28 (br s, 1 H), 7.21 (d, J=7.7 Hz, 1 H), 7.14 (d, J=7.5 Hz, 1 H), 5.31 (d, J=6.3 Hz, 1 H), 4.42 (br s, 2 H), 3.95 (dd, J=11.1, 4.4 Hz, 1 H), 3.90 (dd, J=11.3, 7.7, 1 H), 2.90 (d, J=7.7 Hz, 2 H), 2.82 (br s, 3 H), 2.78-2.62 (m, 1 H), 2.52 (br s, 2 H), 1.49 (s, 9 H); $^{13}$C NMR (125 MHz, CDCl$_3$) δ 144.7, 142.1, 136.9, 127.9, 125.2, 124.0, 80.0, 77.3, 63.1, 52.0, 45.4, 34.1, 32.5, 28.6, 28.2; HRMS (ES+) m/z=330.1689 ([M+Na]$^+$; calcd for C$_{17}$H$_{25}$NO$_4$Na: 330.1681); [α]$_D$$^{17}$ +15.0 (c 0.75, CH$_2$Cl$_2$).

(−)-9: data consistent with (+)-isomer-[α]$_D$$^{28}$ −20.9 (c 2.25, CH$_2$Cl$_2$).

H. tert-butyl(((2R,3S)-2-(((tert-butyldimethylsilyl)oxy)methyl)-3-hydroxy-2,3-dihydro-1H-inden-5-yl)methyl)(methyl)carbamate (10)

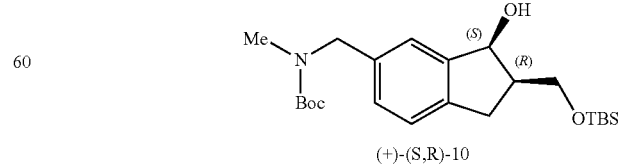

To a precooled (0° C.) solution of (+)-9 (830 mg, 2.54 mmol) and 1H-imidazole (346 mg, 5.08 mmol) in CH$_2$Cl$_2$ (25.4 mL) was added tert-butyl-chlorodimethylsilane (650 mg, 4.31 mmol). The resulting mixture was stirred for 30 min at 0° C., then diluted with EtOAc and washed with water. The combined organic layers were dried over Na$_2$SO$_4$ and concentrated in vacuo. Flash chromatography (SiO$_2$, 9:1 to 1:1 hexanes/EtOAc) afforded (+)-10 as a clear colorless oil (1.01 g, 95%).

$^1$H NMR (500 MHz, CDCl$_3$) δ 7.30 (br s, 1 H), 7.23-7.14 (m, 1 H), 7.12 (br s, 1 H), 5.26 (t, J=5.9 Hz, 1 H), 4.57-4.33 (m, 2 H), 3.98 (dd, J=10.3, 4.8 1 H), 3.90 (dd, J=10.1, 7.3 Hz, 1 H), 3.39-3.18 (m, 1 H), 2.91 (dd, J=8.5, 15.3 Hz, 1 H), 2.86-2.76 (m, 4 H), 2.76-2.55 (m, 1 H), 1.49 (s, 9 H), 0.87 (s, 9 H), 0.09 (s, 3 H), 0.06 (s, 3 H); $^{13}$C NMR (125 MHz, CDCl$_3$, mixture of rotamers) δ 141.4, 136.7, 124.7, 77.1, 63.7, 45.0, 33.8, 32.9, 28.5, 25.7, 18.0, −5.5, −5.6; HRMS (ES+) m/z=444.2544 ([M+Na]$^+$; calcd for C$_{23}$H$_{39}$NO$_4$SiNa: 444.2546); $[α]_D^{25}$ +8.41 (c 0.14, CH$_2$Cl$_2$).

(−)-10: data consistent with (+)-isomer-$[α]_D^{28}$ −20.9 (c 2.25, CH$_2$Cl$_2$).

I. tert-butyl(((2S,3R)-3-azido-2-(((tert-butyldimethylsilyl)oxy)methyl)-2,3-dihydro-1H-inden-5-yl)methyl)(methyl)carbamate (11)

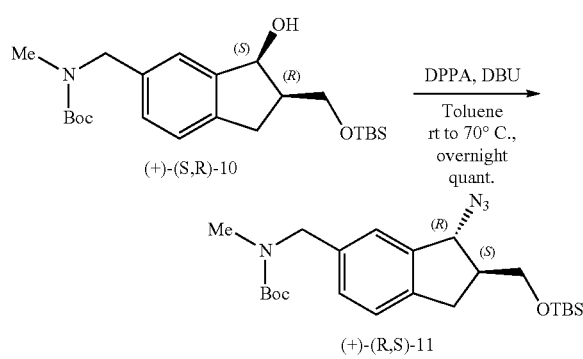

To a solution of (+)-10 (600 mg, 1.423 mmol) in toluene (14.2 mL) was added diphenyl phosphoryl azide (0.920 ml, 4.27 mmol). The mixture was stirred at rt for 5 min, then DBU (0.643 ml, 4.27 mmol) was added. After stirring at rt for 10 min, the reaction mixture was heated to 70° C. and stirred overnight. EtOAc was added, and the resulting mixture was washed with water and brine. The combined organic layers were dried over Na$_2$SO$_4$ and concentrated in vacuo. Flash column chromatography (SiO$_2$, 98:2 hexanes/EtOAc) afforded (+)-11 as a clear colorless oil (650 mg, quant.).

$^1$H NMR (500 MHz, CDCl$_3$) δ 7.14-7.27 (m, 3 H), 4.73 (d, J=6.0 Hz, 1 H), 4.42 (s, 2 H), 3.79 (dd, J=10.5, 5.5 Hz, 1 H), 3.66 (dd, J=10.3, 6.3 Hz, 1 H), 3.05 (dd, J=15.8, 7.8 Hz, 1 H), 2.78-2.83 (2 br s, 3 H, rotamer 1 and 2), 2.68-2.73 (m, 1 H), 2.59-2.63 (m, 1 H), 1.49 (s, 9 H), 0.88 (s, 9 H), 0.07 (s, 3 H), 0.06 (s, 3 H); $^{13}$C NMR (125 MHz, CDCl$_3$, mixture of rotamers) δ 156.3, 155.9, 141.6, 141.1, 137.2, 130.2, 128.5, 128.0, 125.3, 124.2, 123.8, 79.9, 67.6, 63.8, 52.7, 52.0, 49.7, 34.1, 33.1, 28.6, 26.1, 18.5, −5.2; HRMS (ES+) m/z=469.2610 ([M+Na]$^+$; calcd for C$_{23}$H$_{38}$N$_4$O$_3$SiNa: 469.2611); $[α]_D^{28}$ +8.76 (c 0.63, CH$_2$Cl$_2$).

(−)-11: data consistent with (+)-isomer-$[α]_D^{22}$ −10.4 (c 1.0, CH$_2$Cl$_2$).

J. tert-butyl (((2S,3R)-3-amino-2-(((tert-butyldimethylsilyl)oxy)methyl)-2,3-dihydro-1H-inden-5-yl)methyl)(methyl)carbamate (12)

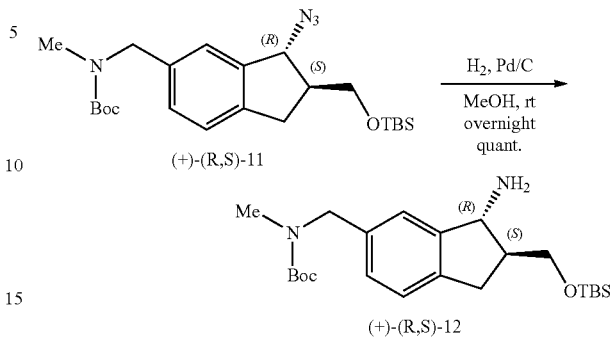

Palladium (10 wt % on carbon, 150 mg, 0.141 mmol) was added to a solution of (+)-11 (630 mg, 1.410 mmol) in MeOH (26.9 mL). The reaction vessel was evacuated and backfilled with hydrogen gas (×4). The reaction mixture was stirred at rt overnight under a hydrogen atmosphere, then filtered through Celite, rinsing with abundant EtOAc. The resulting solution was concentrated in vacuo to give (+)-12 as a clear colorless oil (593 mg, quant.).

$^1$H NMR (500 MHz, CDCl$_3$) δ 7.17 (s, 1 H), 7.11 (d, J=7.5 Hz, 1 H), 7.94 (br s, 1 H), 4.39 (br s, 2 H), 4.14 (d, J=8.0 Hz, 1 H), 3.86 (dd, J=10.0, 5.5 Hz, 1 H), 3.79 (dd, J=10.3, 6.5 Hz, 1 H), 2.92 (dd, J=16.0, 8.0 Hz, 1 H), 2.80 (2 br s, 3 H, rotamer 1 and 2), 2.60 (dd, J=15.8, 9.3 Hz, 1 H), 2.21-2.25 (m, 1 H), 1.96 (2 H, br s, NH$_2$), 1.46 (s, 9 H), 0.89 (s, 9 H), 0.07 (s, 6 H); $^{13}$C NMR (125 MHz, CDCl$_3$, mixture of rotamers) δ 156.2, 156.0, 147.3, 140.9, 136.7, 127.0, 126.5, 124.7, 122.9, 122.7, 79.7, 65.2, 65.0, 54.4, 52.7, 52.0, 33.9, 33.1, 28.6, 26.1, 26.0, 18.4, −5.2, −5.3; HRMS (ES+) m/z=443.2696 ([M+Na]$^+$; calcd for C$_{23}$H$_{40}$N$_2$O$_3$SiNa: 443.2706); $[α]_D^{25}$ +7.12 (c 0.123, CH$_2$Cl$_2$). (−)-12: data consistent with (+)-isomer-$[α]_D^{21}$ −17.5 (c 0.63, CH$_2$Cl$_2$).

K. tert-butyl(((2S,3R)-2-(((tert-butyldimethylsilyl)oxy)methyl)-3-(2-((4-chloro-3-fluorophenyl)amino)-2-oxoacetamido)-2,3-dihydro-1H-inden-5-yl)methyl)(methyl)carbamate (13)

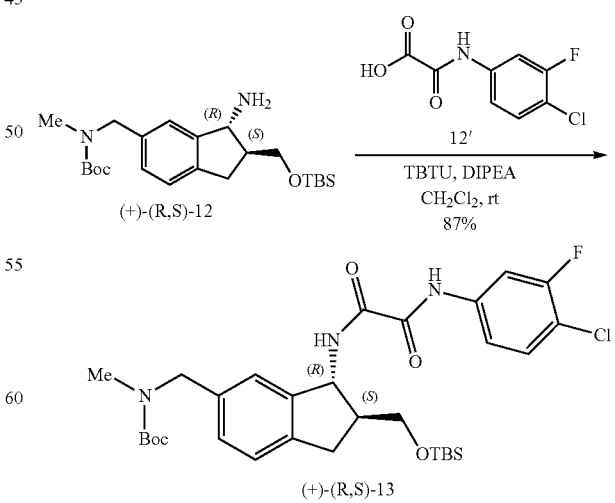

To a solution of (+)-12 (583 mg, 1.386 mmol), 2-((4-chloro-3-fluorophenyl)amino)-2-oxoacetic acid 12' (362 mg, 1.663 mmol) and TBTU (578 mg, 1.802 mmol) in CH$_2$Cl$_2$ (27.7 mL) was added DIPEA (0.363 mL, 2.079 mmol). The resulting mixture was stirred at rt overnight. Once the stirring period was complete, the mixture was diluted with EtOAc, washed with water, 1N aq. HCl, sat. aq. NaHCO$_3$ and brine. The resulting organic layer was dried over Na$_2$SO$_4$ and concentrated in vacuo. Flash column chromatography (SiO$_2$, 7:3 hexanes/EtOAc) afforded (+)-13 as a white solid (739 mg, 87%).

$^1$H NMR (500 MHz, CDCl$_3$) δ 9.37 (s, 1 H), 7.73 (dd, J=10.6, 2.5 Hz, 1 H), 7.65 (d, J=9.7 Hz, 1 H), 7.37-7.42 (m, 1 H), 7.24-7.26 (m, 1 H), 7.17-7.23 (m, 1 H), 7.13 (br s, 1 H), 7.08 (s, 1 H), 5.37 (t, J=8.6 Hz, 1 H), 4.38 (br s, 2 H), 3.81 (d, J=5.5 Hz, 2 H), 3.09 (dd, J=16.0, 8.0 Hz, 1 H), 2.71-2.87 (m, 4 H), 2.51-2.58 (m, 1 H), 1.42-1.51 (m, 9 H), 0.86-1.01 (m, 9 H), 0.08 (s, 3 H), 0.07 (s, 3 H); $^{13}$C NMR (125 MHz, CDCl$_3$) δ 159.2, 157.5, 143.5, 141.3, 137.2, 130.9, 125.0, 115.9 (d, J$_{CF}$=3.5 Hz), 108.4 (d, J$_{CF}$=26 Hz), 70.9, 69.4, 63.8, 57.0, 51.0, 33.9, 33.2, 28.4, 25.8, 18.2, −5.5; HRMS (ES+) m/z=642.2548 ([M+Na]; calcd for C$_{31}$H$_{43}$N$_3$O$_5$SiClFNa: 642.2542); [α]$_D^{18}$ +49.77 (c 0.23, CH$_2$Cl$_2$). (−)-13: data consistent with (+)-isomer-[α]$_D^{19}$ −47.4 (c 1.9, CH$_2$Cl$_2$).

L. tert-butyl(((2S,3R)-3-(2-((4-chloro-3-fluorophenyl)amino)-2-oxoacetamido)-2-(hydroxylmethyl)-2,3-dihydro-1H-inden-5-yl)methyl)(methyl)carbamate (14)

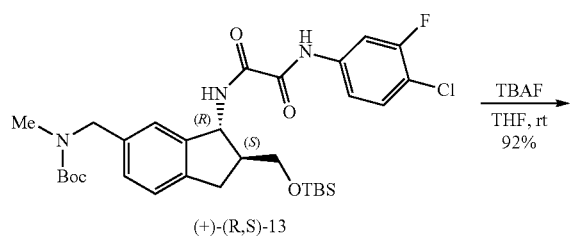

(+)-(R,S)-13

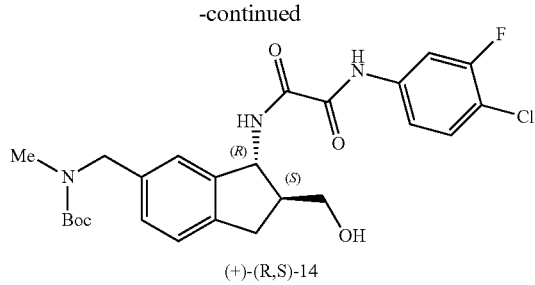

(+)-(R,S)-14

To a solution of (+)-13 (0.73 g, 1.177 mmol) in THF (23.5 mL) at rt was added TBAF (1 M solution in THF, 2.35 ml, 2.35 mmol). The reaction was stirred at rt overnight, then diluted with EtOAc and washed with water and brine. The resulting organic layer was dried over Na$_2$SO$_4$ and concentrated in vacuo. Flash column chromatography (SiO$_2$, 1:1 hexanes/EtOAc) afforded (+)-14 as a white solid (550 mg, 92%).

$^1$H NMR (500 MHz, CDCl$_3$) δ 9.46 (s, 1 H), 7.97 (br s, 1 H), 7.71 (dd, J=10.5, 2.0 Hz, 1 H), 7.37 (t, J=8.3 Hz, 1 H), 7.27 (dd, J=7.0, 1.0 Hz, 1 H), 7.14-7.18 (m, 2 H), 7.09 (s, 1 H), 5.25 (s, 1 H), 4.39 (s, 2 H), 3.75-3.84 (m, 2 H), 3.08-3.10 (m, 1 H), 2.80 (s, 3 H), 2.69-2.72 (m, 1 H), 2.56-2.59 (m, 1 H), 1.46 (s, 9 H); $^{13}$C NMR (125 MHz, CDCl$_3$, mixture of rotamers) δ 160.3, 158.3 (d, J$_{CF}$=246 Hz), 157.3, 156.3, 156.0, 141.3, 141.1, 137.8, 136.4 (d, J$_{CF}$=9.3 Hz), 131.1, 128.3, 128.0, 125.4, 123.5, 123.2, 117.5 (d, J$_{CF}$=18 Hz), 116.3 (d, J$_{CF}$=3.5 Hz), 108.7 (d, J$_{CF}$=26 Hz), 80.0, 64.4, 58.5, 52.6, 52.0, 34.2, 33.5, 28.6; HRMS (ES−) m/z=504.1709 ([M−H]$^−$; calcd for C$_{25}$H$_{28}$ClFN$_3$O$_5$: 504.1702). [α]$_D^{23}$ +31.4 (c 0.275, EtOAc). (−)-14: data consistent with (+)-isomer-[α]$_D^{23}$ −38.3 (c 0.40, EtOAc).

M. tetra-Boc-JP-III-048 (15)

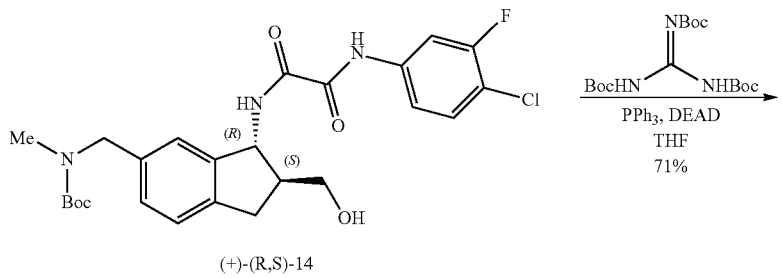

(+)-(R,S)-14

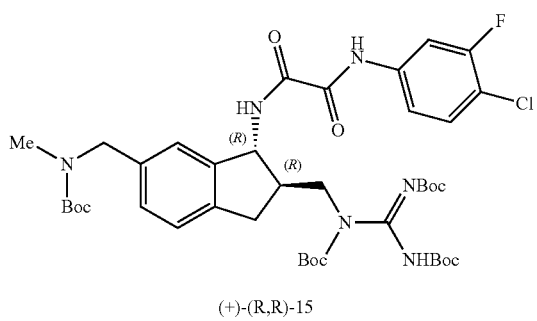

(+)-(R,R)-15

To a solution of (−)-14 (250 mg, 0.494 mmol) in THF (16.5 mL) were added N,N',N''-tri-Boc-guanidine (533 mg, 1.482 mmol) and triphenylphosphine (194 mg, 0.741 mmol). The suspension was cooled to 0° C. and DEAD (0.338 mL, 0.741 mmol) was added dropwise. The reaction vessel was sealed and heated to 80° C. for 90 min under microwave conditions. After cooling to rt, the reaction was quenched by addition of sat. aq. NaHCO$_3$ and extracted with EtOAc. The combined organic layers were washed with brine, dried over Na$_2$SO$_4$ and concentrated in vacuo. Flash column chromatography (SiO$_2$, 10:1 to 2:1 hexanes/EtOAc) afforded (+)-15 as a white foam (298 mg, 71%).

$^1$H NMR (500 MHz, CDCl$_3$) δ 9.38 (s, 1 H), 7.79 (d, J=9.1 Hz, 1 H), 7.74 (dd, J=10.7, 2.4 Hz, 1 H), 7.37 (t, J=8.2 Hz, 1 H), 7.22-7.26 (m, J=8.7, 1.2, 1.2 Hz, 1 H), 7.18 (d, J=7.7 Hz, 1 H), 7.11 (br s, 1 H), 7.03 (s, 1 H), 5.24 (t, J=8.7 Hz, 1 H), 4.36 (br s, 2 H), 4.08-4.23 (m, 2 H), 3.15 (dd, J=15.5, 8.1 Hz, 1 H), 2.83-2.91 (m, 1 H), 2.71-2.83 (m, 4 H), 1.46-1.51 (m, 27 H), 1.44 (s, 9 H); $^{13}$C NMR (125 MHz, CDCl$_3$, mixture of rotamers) δ 187.8, 159.5, 158.3, 158.1 (J$_{CF}$=246 Hz) 157.7, 157.3, 153.1, 140.9, 137.2, 136.4, 130.7, 125.0, 117.0, 115.8 (d, J$_{CF}$=4 Hz), 108.3 (d, J$_{CF}$=27 Hz), 83.5, 58.4, 49.8, 48.3, 34.7, 33.8, 28.4, 28.1, 28.0, 27.9, 27.9; HRMS (ES+) m/z=847.3782 ([M+H]$^+$; calcd for C$_{41}$H$_{57}$N$_6$O$_{10}$ClF: 847.3809); +22.6 (c 1.15, CH$_2$Cl$_2$).

(−)-15: data consistent with (+)-isomer-[α]$_D^{20}$ −25.1 (c 2.0, CH$_2$Cl$_2$).

N. JP-III-048

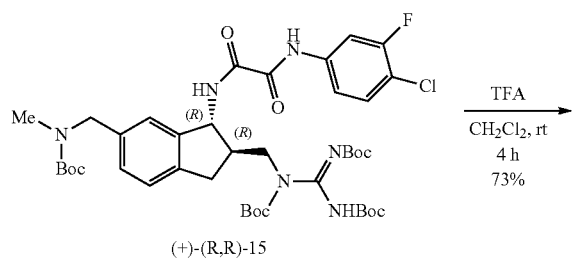

(+)-(R,R)-15

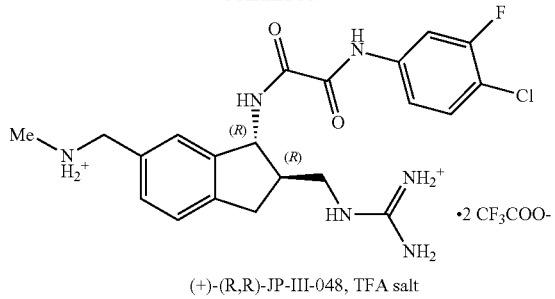

(+)-(R,R)-JP-III-048, TFA salt

To a solution of (+)-15 (0.442 g, 0.522 mmol) in CH$_2$Cl$_2$ (10.4 mL) was added TFA (1.849 mL, 23.99 mmol). The reaction mixture was stirred at rt for 4 h then concentrated in vacuo. The crude residue was taken up in water/acetonitrile (90:10, 5 mL). Formic acid (0.1 mL) was added. The resulting clear solution was purified by HPLC (5 injections of 1300 µL each). Eluant: 90:10 to 60:40 water/acetonitrile (12-minute gradient). Flow rate: 15 mL/min. Product retention time: 5-6 min. Product fractions were combined and acetonitrile was removed in vacuo. The resulting aqueous solution was deep-frozen (−78° C. bath) and lyophilized (0.035 mbar) to afford the bis-formate salt (+)-JP-III-048 as a white powder (256 mg, 73%).

$^1$H NMR (500 MHz, DMSO-d$_6$) δ: 11.10 (s, 1 H), 9.45 (d, J=8.9 Hz, 1 H), 8.68 (br s, 2 H), 7.99 (dd, J=11.7, 2.2 Hz, 1 H), 7.81 (t, J=5.5 Hz, 1 H), 7.78 (dd, J=8.8, 1.7 Hz, 1 H), 7.61 (t, J=8.7 Hz, 1 H), 7.32 (s, 2 H), 7.25 (s, 1 H), 5.19 (t, J=8.9 Hz, 1 H), 4.05 (s, 2 H), 3.26-3.45 (m, 4 H), 3.13 (dd, J=15.7, 8.1 Hz, 1 H), 2.83-2.91 (m, 1 H), 2.68 (dd, J=15.5, 9.5 Hz, 2 H); $^{13}$C NMR (125 MHz, DMSO-d$_6$, mixture of rotamers) δ 159.9, 158.7, 158.4, 158.1, 157.8, 157.0, 155.8, 143.0, 141.9, 138.2 (d, J$_{CF}$=10 Hz), 131.2, 130.6, 130.1, 129.3, 124.9 (d, J$_{CF}$=10 Hz), 117.3 (d, J$_{CF}$=3.2 Hz), 114.5, 114.4, 108.4 (d, J$_{CF}$=26 Hz), 56.9, 51.4, 45.4, 42.9, 40.1, 39.9, 39.8, 39.6, 33.7, 32.3; HRMS (ES+) m/z=447.1711 ([M−H]$^+$; calcd for C$_{21}$H$_{25}$N$_6$O$_2$ClF: 447.1712); +27.3 (c 0.29, CH$_3$OH). Anal. Calcd for C$_{25}$H$_{26}$ClF$_7$N$_6$O$_6$: C, 44.49; H, 3.88; Cl, 5.25; F, 19.70; N, 12.45; O, 14.22. Found: C, 44.48; H, 3.93; Cl, 5.29; F, 18.26; N, 12.16; O, n/d.

(−)-JP-III-048: data consistent with (+)-isomer-[α]$_D^{17}$ −27.3 (c 0.53, CH$_3$OH).

Example 2

Preparation of BNM-III-170

Scheme 2

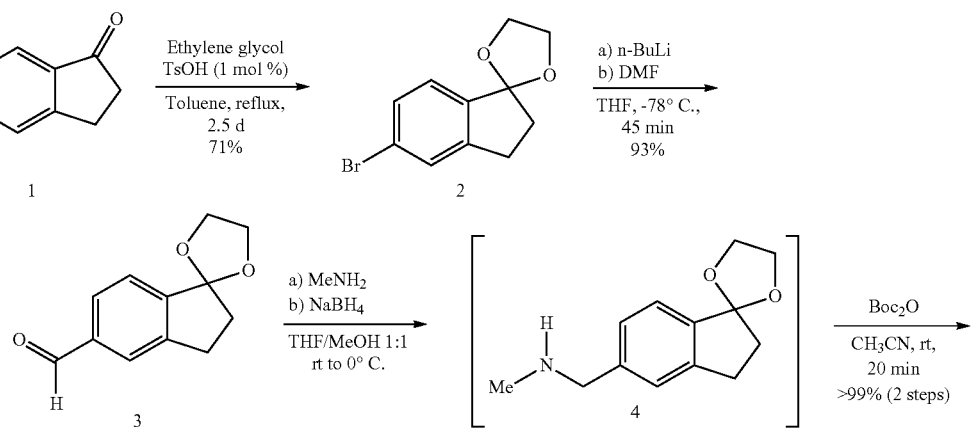

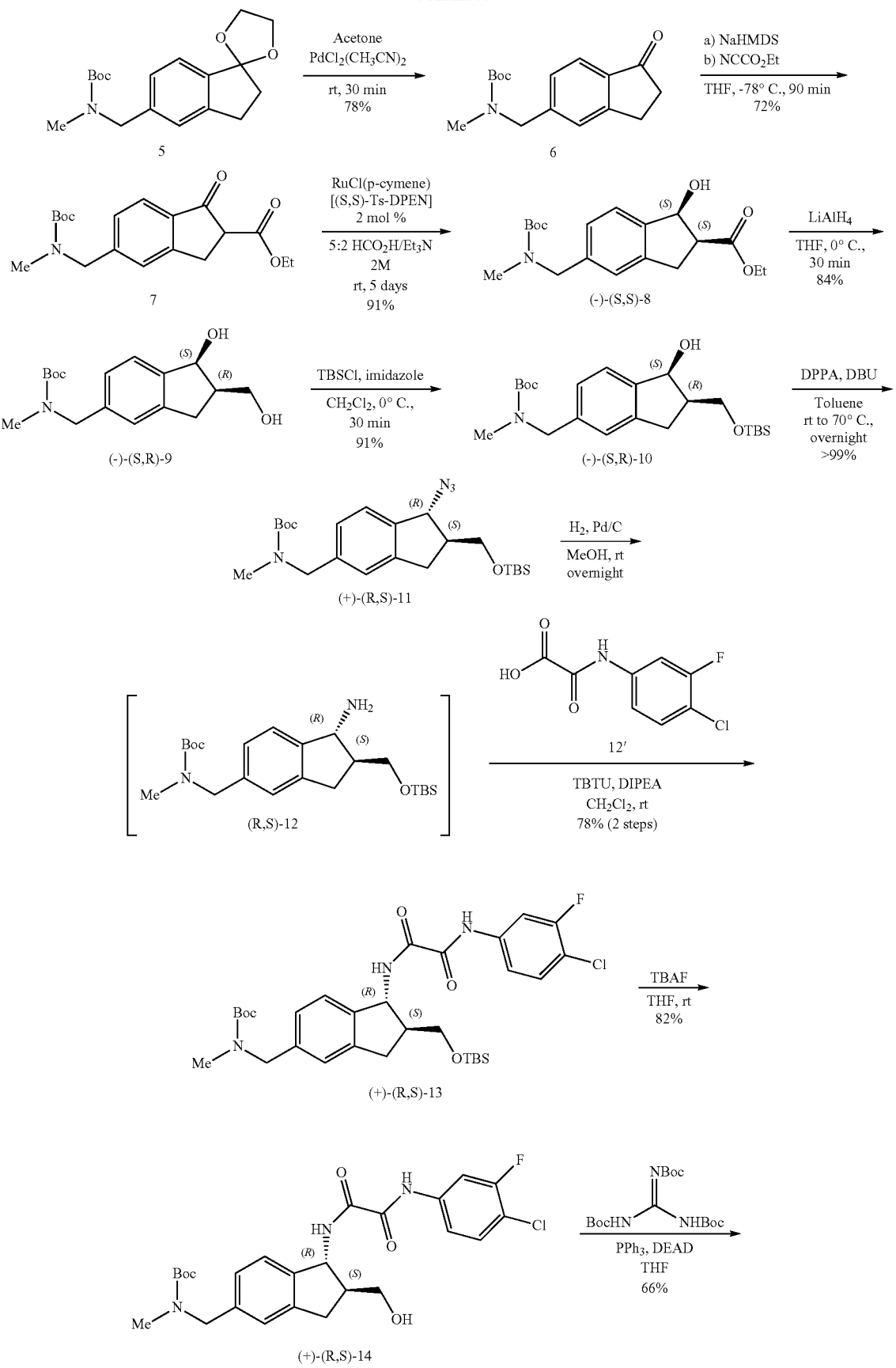

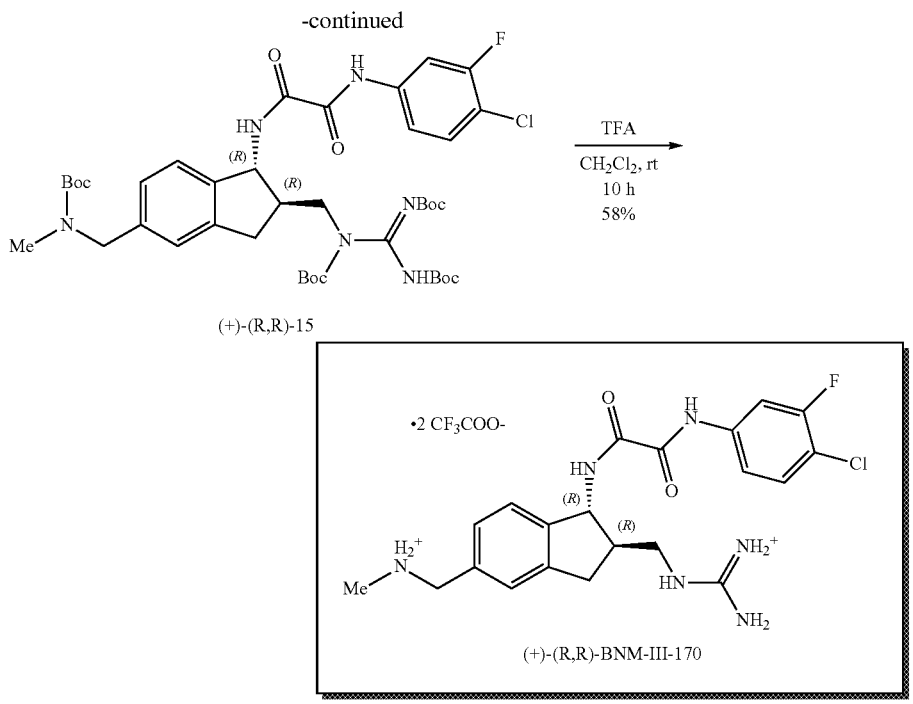

(+)-(R,R)-15

(+)-(R,R)-BNM-III-170

Overall: 15 steps, 6.2% yield
Maximum amount prepared in one run: 106 mg

A. 5-bromo-2,3-dihydrospiro[indene-1,2'-[1,3]dioxolane] (2)

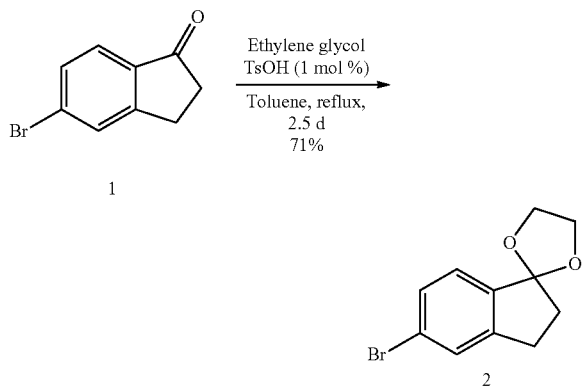

To a solution of 5-bromo-2,3-dihydro-1H-inden-1-one (2.00 g, 9.48 mmol) in benzene (40 mL) were added ethane-1,2-diol (10.57 mL, 190 mmol) and tosic acid (0.018 g, 0.095 mmol). The flask was fitted with a Dean-Stark apparatus pre-filled with benzene and a reflux condenser, and heated to 115° C. over 48 h. The reaction mixture was diluted with EtOAc and neutralized with sat. aq. NaHCO$_3$. Layers were separated and the resulting aqueous layer was extracted with EtOAc. The combined organic layers were dried over anhydrous Na$_2$SO$_4$ and concentrated in vacuo. Flash column chromatography (SiO$_2$, 95:5 hexanes/EtOAc) afforded 2 as a clear, pale yellow oil (1.72 g, 71%).

$^1$H NMR (500 MHz, CDCl$_3$) δ 7.39 (d, J=8.75 Hz, 2 H), 7.23 (d, J=8.0 Hz, 1 H), 4.21-4.15 (m, 2 H), 4.12-4.05 (m, 2 H), 2.94 (t, J=6.9 Hz, 2 H), 2.30 (t, J=7.0 Hz, 2 H); $^{13}$C NMR (125 MHz, CDCl$_3$) δ 146.0, 141.2, 130.2, 128.4, 124.8, 123.8, 116.7, 65.4, 37.2, 28.4; HRMS (ES+) m/z=255.0029 ([M+H]$^+$; calcd for C$_{11}$H$_{12}$O$_2$Br: 255.0021)

B. 2,3-dihydrospiro[indene-1,2'-[1,3]dioxolane]-5-carbaldehyde (3)

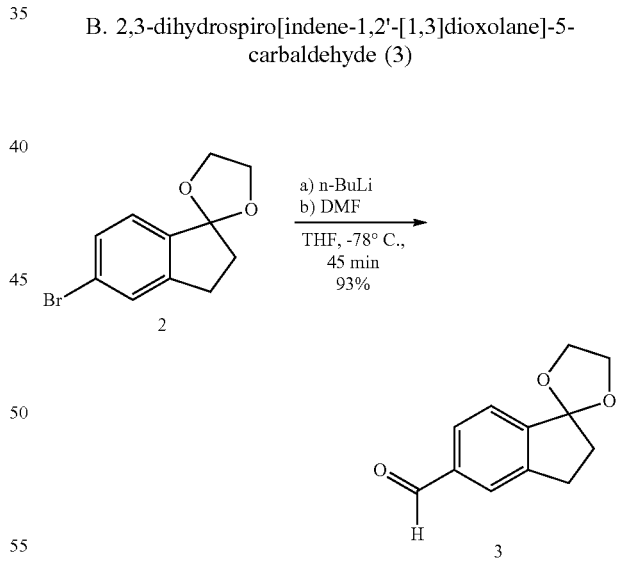

To a precooled (−78° C.) solution of 2 (1.70 g, 6.66 mmol) in THF (9.51 mL) was slowly added butyllithium (3.00 mL of a 2.44 M solution in hexane, 24.71 mmol). The reaction mixture was stirred at −78° C. for 10 min, then N,N-dimethylformamide (0.616 mL, 7.99 mmol) was added. The resulting mixture was stirred at −78° C. for an additional 15 min, then allowed to warm to rt and stirred for a final 30 min. The reaction was quenched with sat. aq. NaHCO$_3$ and diluted with EtOAc. The combined organic layers were washed with water and brine, dried over anhydrous Na$_2$SO$_4$ and concentrated in vacuo. Flash column chromatography (SiO$_2$, 5:1 hexanes/EtOAc) afforded 3 as a clear orange oil (1.27 g, 93%).

$^1$H NMR (500 MHz, CDCl$_3$) δ 10.03 (s, 1 H), 7.78 (t, J=7.4 Hz, 2 H), 7.51 (d, J=7.8 Hz, 1 H), 4.25-4.19 (m, 2 H), 4.15-4.09 (m, 2 H), 3.02 (t, J=7.2 Hz, 2 H), 2.36 (t, J=7.0 Hz, 2 H); $^{13}$C NMR (125 MHz, CDCl$_3$) δ 192.4, 148.7, 144.7, 137.8, 129.2, 126.6, 123.9, 116.5, 65.6, 37.3, 28.4; HRMS (ES+) m/z=205.0859 ([M+H]$^+$; calcd for C$_{12}$H$_{13}$O$_3$: 205.0865).

C. tert-butyl ((2,3-dihydrospiro[indene-1,2'-[1,3] dioxolan]-5-yl)methyl)(methyl)carbamate (5)

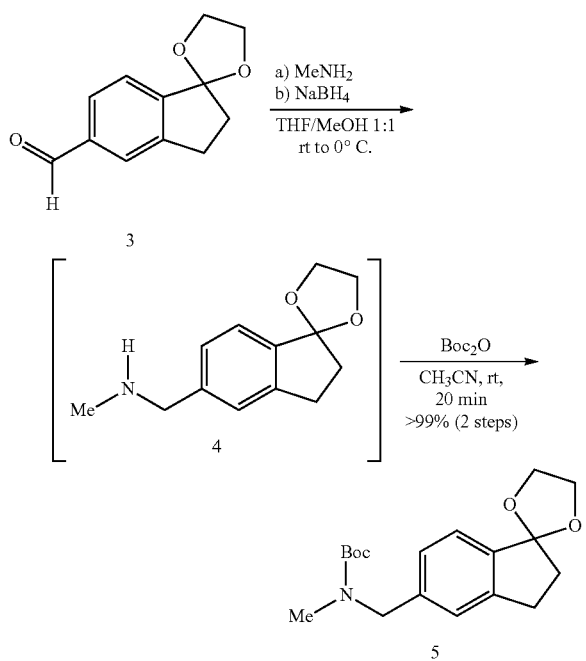

At 0° C., methylamine (11.86 mL of a 2 M solution in THF, 23.73 mmol) was added to 3 (neat, 1.249 g, 5.93 mmol). The reaction was warmed to rt and stirred for 30 min, then cooled to 0° C. MeOH (8.47 mL) was then added, followed by sodium borohydride (0.112 g, 2.97 mmol). The resulting mixture was stirred at 0° C. for 40 min. A second portion of sodium borohydride (0.112 g, 2.97 mmol) was then added. The reaction mixture was stirred for an additional 40 min, then quenched with water and extracted with EtOAc. The combined organic layers were washed with brine, dried over anhydrous Na$_2$SO$_4$, and concentrated in vacuo. The resulting crude amine (4) was dissolved in acetonitrile (24 mL) and added to a solution of Boc$_2$O (1.54 mL, 6.64 mmol) in acetonitrile (24 mL). The mixture was stirred at rt for 15 min, then concentrated in vacuo. Flash column chromatography (SiO$_2$, 95:5 to 70:30 hexanes/EtOAc) afforded 5 as a clear colorless oil (1.93 g, >99%).

$^1$H NMR (500 MHz, CDCl$_3$) δ 7.39 (d, J=7.5 Hz, 1 H), 7.11 (br s, 2 H), 4.43 (s, 2 H), 4.23-4.17 (m, 2 H), 4.12-4.06 (m, 2 H), 2.94 (t, J=6.9 Hz, 2 H), 2.77-2.83 (2 br s, 3 H, rotamers 1 and 2), 2.32 (t, J=6.9 Hz, 2 H), 1.49 (s, 9 H); $^{13}$C NMR (125 MHz, CDCl$_3$, mixture of rotamers) δ 146.7, 144.2, 141.2, 139.9, 123.3, 117.1, 85.3, 65.3, 52.7, 37.3, 34.0, 28.6, 28.5, 27.5; HRMS (ES+) m/z=320.1854 ([M+H]$^+$; calcd for C$_{18}$H$_{26}$NO$_4$: 320.1862).

D. tert-butyl methyl((1-oxo-2,3-dihydro-1H-inden-5-yl)methyl)carbamate (6)

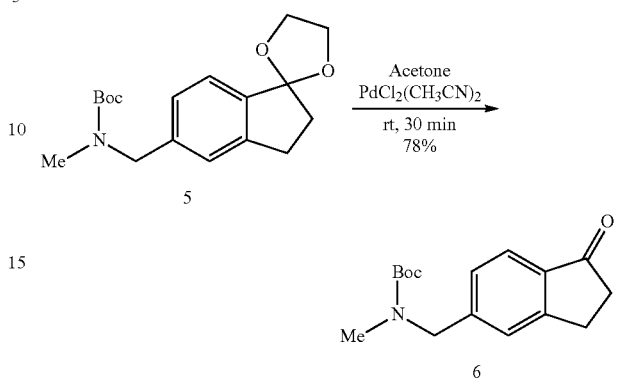

To a solution of 5 (1.929 g, 6.04 mmol) in acetone (60 mL) was added bis(acetonitrile)-palladium(II) dichloride (31 mg, 0.121 mmol). The reaction mixture was stirred at rt for 30 min then concentrated in vacuo. The resulting residue was taken up in EtOAc (150 mL) and washed with sat. aq. NaHSO$_3$ (3×20 mL). The combined organic layers were dried over anhydrous Na$_2$SO$_4$ and concentrated in vacuo. Flash column chromatography (SiO$_2$, 85:15 to 70:30 hexanes/EtOAc) afforded 6 as a clear colorless oil that, upon standing, precipitated to form a white solid (1.29 g, 78%).

$^1$H NMR (500 MHz, CDCl$_3$) δ 7.74 (d, J=7.9 Hz, 1 H), 7.33 (s, 1 H), 7.24 (d, J=6.0 Hz, 1 H), 4.52 (s, 2 H), 3.14 (t, J=5.8 Hz, 2 H), 2.85-2.89 (2 br s, 3 H, rotamers 1 and 2), 2.72 (t, J=5.8 Hz, 2 H), 1.47-1.51 (2 br s, 9 H); $^{13}$C NMR (125 MHz, CDCl$_3$, mixture of rotamers) δ 155.9, 145.8, 136.5, 126.9, 126.5, 124.1, 80.2, 52.9, 36.6, 34.5, 28.6, 26.1, 25.9, 23.1; HRMS (ES+) m/z=298.1432 ([M+Na]$^+$; calcd for C$_{16}$H$_{21}$NO$_3$Na: 298.1419).

E. (±)-ethyl 5-(((tert-butoxycarbonyl)(methyl) amino)methyl)-1-oxo-2,3-dihydro-1H-indene-2-carboxylate (7)

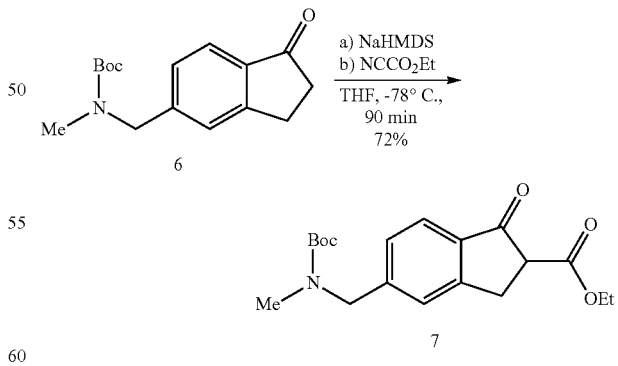

To a precooled (−78° C.) solution of 6 (1.29 g, 4.70 mmol) in THF (42 mL) was slowly added NaHMDS (9.39 mL of a 1 M solution in THF, 9.39 mmol). The mixture was stirred at −78° C. for 10 min, then ethyl carbonocyanidate (0.598 mL, 6.10 mmol) was added and stirring was continued at −78° C. for 1 h. The reaction was quenched with sat. aq.

$NH_4Cl$ and diluted with EtOAc. Layers were separated and the resulting aqueous layer was extracted with EtOAc. The combined organic layers were washed with brine, dried over $Na_2SO_4$ and concentrated in vacuo. Flash column chromatography ($SiO_2$, 85:15 hexanes/EtOAc) afforded (±)-7 as a clear purple oil (1.17 g, 72%).

$^1$H NMR (500 MHz, $CDCl_3$) δ 10.46 (s, enol OH), 7.67 (m, 1 H), 7.35 (s, 1 H), 7.26 (s, 1 H), 4.51 (br s, ketoester 2H and enol 2 H), 4.35 (q, J=7.1 Hz, enol 2 H), 4.29-4.23 (m, ketoester 2 H), 3.73 (dd, J=7.8, 3.7 Hz, ketoester 1 H), 3.55 (dd, J=17.3, 4.0 Hz, ketoester 1 H), 3.52 (s, enol 2 H), 3.36 (dd, J=17.3, 8.3 Hz, ketoester 1 H), 2.85-2.90 (2 br s, ketoester 3 H and enol 3 H, rotamer 1 and 2), 1.51 (br s, ketoester 9 H), 1.46 (br s, enol 9 H), 1.37 (t, J=7.2 Hz, enol 3 H), 1.32 (t, J=7.2 Hz, ketoester 3 H); $^{13}$C NMR (125 MHz, $CDCl_3$, mixture of rotamers+enol) δ 199.1, 169.3, 154.4, 136.3, 134.7, 127.4, 125.0, 120.9, 80.3, 61.9, 60.2, 53.7, 34.5, 32.6, 30.4, 28.6, 28.5, 14.6, 14.3; HRMS (ES+) m/z=370.1625 ([M+Na]$^+$; calcd for $C_{19}H_{25}NO_5Na$: 370.1630).

F. Ethyl (1S,2S)-5-(((tert-butoxycarbonyl)(methyl)amino)methyl)-1-hydroxy-2,3-dihydro-1H-indene-2-carboxylate (8)

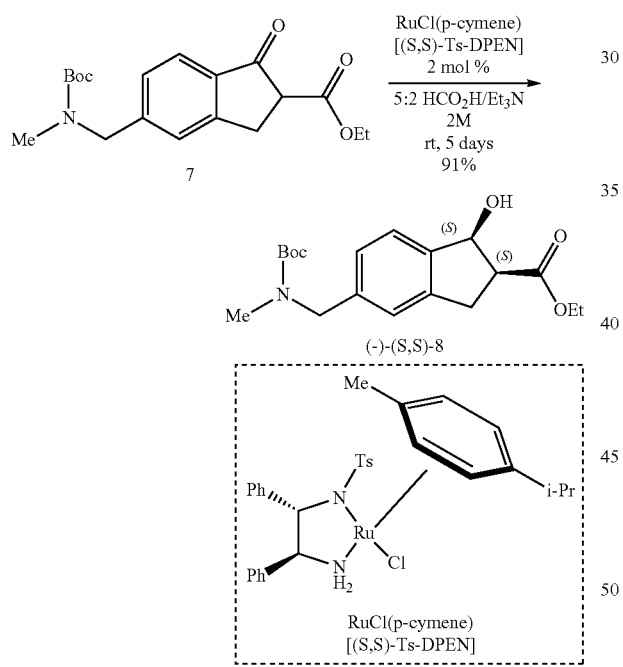

RuCl(p-cymene)[(S,S)-Ts-DPEN] (0.021 g, 0.033 mmol) was added in one portion to a solution of (±)-7 (560 mg, 1.612 mmol) in HCOOH/Et$_3$N (5:2, 0.85 mL). The reaction mixture was stirred at rt for 3 days, diluted with $CH_2Cl_2$ and washed with $H_2O$ (×2). The combined organic layers were dried over $Na_2SO_4$ and concentrated in vacuo. Flash column chromatography ($SiO_2$, hexanes/EtOAc 7:3) afforded (−)-8 as a clear pale pink oil (515 mg, 91%).

$^1$H NMR (500 MHz, $CDCl_3$) δ 7.40 (d, J=7.6 Hz, 1 H), 7.13 (s, 2 H), 5.34-5.31 (m, 1 H), 4.42 (s, 2 H), 4.25 (q, J=7.2 Hz, 2 H), 3.45-3.37 (m, 2 H), 3.13-3.05 (m, 1 H), 2.83-2.79 (m, 3 H), 1.49 (s, 9 H), 1.33 (t, J=7.3 Hz, 3 H); $^{13}$C NMR (125 MHz, $CDCl_3$, mixture of rotamers) δ 173.2, 142.5, 141.9, 139.4, 125.2, 75.6, 61.1, 49.7, 34.1, 33.0, 28.6, 14.4; HRMS (ES+) m/z=372.1769 ([M+Na]$^+$; calcd for $C_{19}H_{27}NO_5Na$: 372.1787); [α]$_D^{21}$ −11.3 (c 0.42, $CH_2Cl_2$) (+)-8: data consistent with (−)-isomer-[α]$_D^{21}$ +5.4 (c 1.0, $CH_2Cl_2$)

Enantiomeric excess determined by SFC (see table below):

| Enantiomer | (−)-(S,S)-8 | (+)-(R,R)-8 |
|---|---|---|
| er | 99:1 | 99:1 |

Method: column: Chiralpak AS-H; eluent: 10% MeOH in supercritical $CO_2$; flow rate: 4 mL/min; pressure: 12 MPa. Retention times: (−)-(S,S)-8: 2.0 min, (+)-(R,R)-8: 1.9 min.

G. tert-butyl (((1S,2R)-1-hydroxy-2-(hydroxymethyl)-2,3-dihydro-1H-inden-5-yl)methyl)(methyl)carbamate (9)

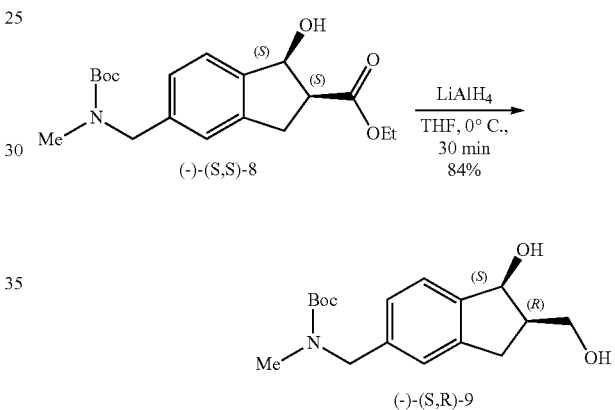

To a precooled (0° C.) suspension of lithium aluminum hydride (0.149 g, 3.93 mmol) in THF (4 mL) was added dropwise over 5 min via cannula a solution of (−)-8 (458 mg, 1.31 mmol) in THF (8 mL). The reaction was stirred for 30 min at 0° C. then quenched with 15% aq. sodium potassium tartrate and stirred at rt for an additional 10 min. Water was added, followed by EtOAc. The resulting biphasic mixture was filtered through Celite, rinsing with abundant water and EtOAc. The layers were separated and the resulting aqueous layer was extracted with EtOAc. The combined organic layers were dried over $Na_2SO_4$ and concentrated in vacuo. Flash column chromatography ($SiO_2$, 1:1 to 0:1 hexanes/EtOAc) afforded (−)-9 as a clear colorless oil (338 mg, 84%).

$^1$H NMR (500 MHz, $CDCl_3$) δ 7.37 (d, J=7.6 Hz, 1 H), 7.10-7.08 (m, 2 H), 5.30 (d, J=4.7 Hz, 1 H), 4.41 (s, 2 H), 3.94 (dd, J=11.2 Hz, 4.5 Hz, 1 H), 3.90-3.87 (m, 1 H), 2.89 (d, J=7.8 Hz, 2 H), 2.81 (br s, 3 H), 2.69 (br s, 3 H), 1.49 (s, 9 H); $^{13}$C NMR (125 MHz, $CDCl_3$) δ 143.7, 143.3, 138.9, 124.9, 80.0, 77.4, 63.1, 60.6, 45.4, 34.1, 32.8, 28.6, 21.2, 14.3; HRMS (ES+) m/z=330.1670 ([M+Na]$^+$; calcd for $C_{17}H_{25}NO_4Na$: 330.1681);

[α]$_D^{22}$ −5.8 (c 1.0, EtOAc). (+)-9: data consistent with (−)-isomer-[α]$_D^{23}$ +2.2 (c 1.0, EtOAc).

H. tert-butyl (((1S,2R)-2-(((tert-butyldimethylsilyl)oxy)methyl)-1-hydroxy-2,3-dihydro-1H-inden-5-yl)methyl)(methyl)carbamate (10)

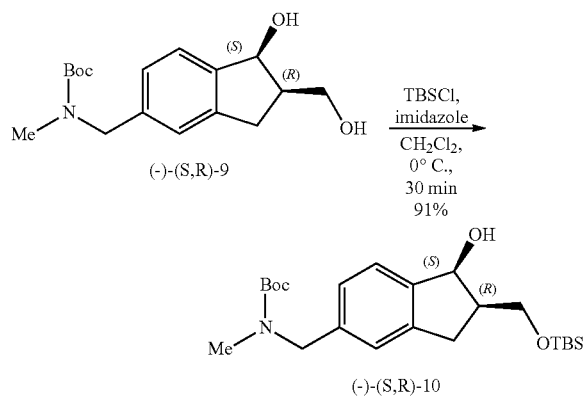

To a precooled (0° C.) solution of (−)-9 (0.278 g, 0.904 mmol) and 1H-imidazole (123 mg, 2.71 mmol) in CH$_2$Cl$_2$ (9 mL) was added tert-butyl-chlorodimethylsilane (0.232 g, 1.54 mmol). The resulting mixture was stirred for 30 min at 0° C., then diluted with EtOAc and washed with water. The combined organic layers were dried over Na$_2$SO$_4$ and concentrated in vacuo. Flash column chromatography (SiO$_2$, 9:1 to 1:1 hexanes/EtOAc) afforded (−)-10 as a clear colorless oil (348 mg, 91%).

$^1$H NMR (500 MHz, CDCl$_3$) δ 7.39 (d, J=8.1 Hz, 1 H), 7.10 (br s, 2 H), 5.27 (t, J=5.8 Hz, 1 H), 4.42 (s, 2 H), 3.99 (dd, J=10.3 Hz, 4.7 Hz, 1 H), 3.90 (dd, J=10.3 Hz, 7.2 Hz, 1 H), 3.27 (s, 1 H), 2.91 (dd, J=16.0 Hz, 8.2 Hz, 1 H), 2.85-2.79 (m, 4 H), 2.71-2.68 (m, 1 H), 1.49 (s, 9 H), 0.87 (s, 9 H), 0.10 (s, 3 H), 0.07 (s, 3 H); $^{13}$C NMR (125 MHz, CDCl$_3$, mixture of rotamers) δ 144.0, 143.1, 138.4, 124.9, 63.8, 45.1, 33.9, 33.3, 28.6, 25.9, 18.2, −5.3, −5.4; HRMS (ES+) m/z=444.2530 ([M+Na]$^+$; calcd for C$_{23}$H$_{39}$NO$_4$SiNa: 444.2546); [α]$_D^{22}$ −6.1 (c 0.53, CH$_2$Cl$_2$).

(+)-10: data consistent with (−)-isomer-[α]$_D^{22}$ +4.06 (c 0.37, CH$_2$Cl$_2$)

I. tert-butyl (((1R,2S)-1-azido-2-(((tert-butyldimethylsilyl)oxy)methyl)-2,3-dihydro-1H-inden-5-yl)methyl)(methyl)carbamate (11)

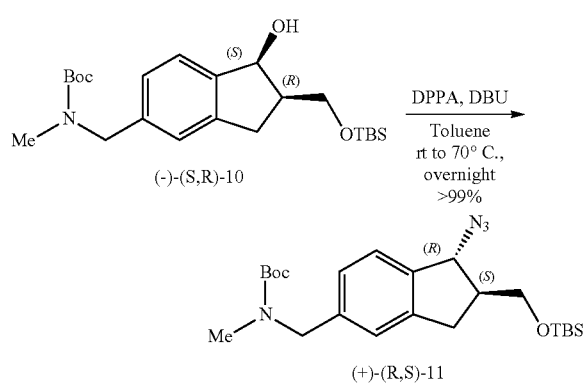

To a solution of (−)-10 (355 mg, 0.795 mmol) in toluene (9 mL) was added diphenyl phosphoryl azide (0.514 mL, 2.39 mmol). The mixture was stirred at rt for 5 min, then DBU (0.359 mL, 2.385 mmol) was added. After stirring at rt for 10 min, the reaction mixture was heated to 70° C. and stirred overnight. EtOAc was added, and the resulting mixture was washed with water and brine. The combined organic layers were dried over Na$_2$SO$_4$ and concentrated in vacuo. Flash column chromatography (SiO$_2$, 98:2 hexanes/EtOAc) afforded (+)-11 as a clear colorless oil (367 mg, >99%).

$^1$H NMR (500 MHz, CDCl$_3$) δ 7.41 (t, J=8.2 Hz, 1 H), 7.11 (s, 2 H), 4.75 (d, J=5.5 Hz, 1 H), 4.42 (s, 2 H), 3.79 (dd, J=10.2 Hz, 5.4 Hz, 1 H), 3.66 (dd, J=10.3 Hz, 6.3 Hz, 1 H), 3.07 (dd, J=16.1 Hz, 8.2 Hz, 1 H), 2.80-2.84 (2 br s, 3 H, rotamer 1 and 2), 2.71 (dd, J=16.1 Hz, 6.6 Hz, 1 H), 2.65-2.60 (m, 1 H), 1.49 (br s, 9 H), 0.90 (s, 9 H), 0.08 (s, 3 H), 0.07 (s, 3 H); $^{13}$C NMR (125 MHz, CDCl$_3$) δ 143.0, 139.6, 130.2, 126.3, 124.8, 120.4, 67.4, 63.7, 49.6, 34.1, 33.3, 28.6, 26.0, 18.5, −5.2, −5.3; HRMS (ES+) m/z=469.2603 ([M+Na]$^+$; calcd for C$_{23}$H$_{38}$N$_4$O$_3$SiNa: 469.2611); [α]$_D^{22}$ +25.0 (c 0.36, CH$_2$Cl$_2$).

(−)-11: data consistent with (+)-isomer-[α]$_D^{22}$ −28.3 (c 0.53, CH$_2$Cl$_2$)

J. tert-butyl (((1R,2S)-2-(((tert-butyldimethylsilyl)oxy)methyl)-1-(2-((4-chloro-3-fluorophenyl)amino)-2-oxoacetamido)-2,3-dihydro-1H-inden-5-yl)methyl)(methyl)carbamate (13)

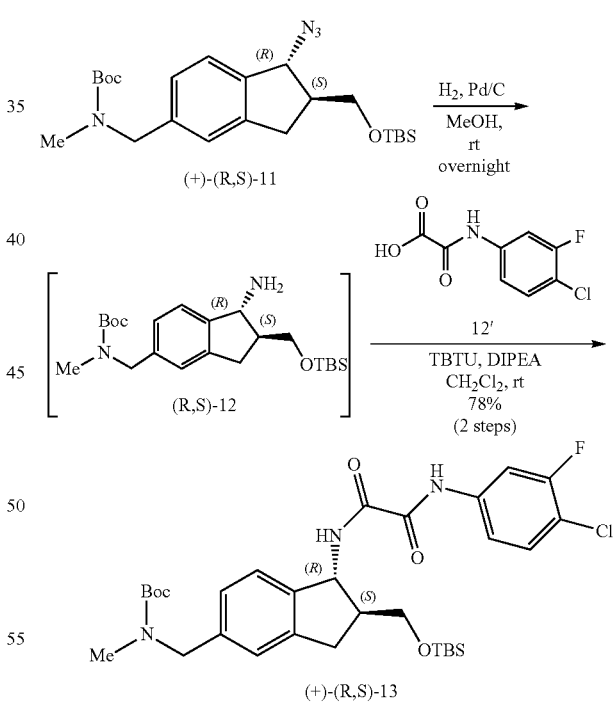

Palladium (10 wt % on carbon, 81 mg, 0.076 mmol) was added to a solution of (+)-11 (340 mg, 0.761 mmol) in MeOH (12.7 mL). The reaction vessel was evacuated and backfilled with hydrogen gas (×4). The reaction mixture was stirred at rt overnight under a hydrogen atmosphere, then filtered through Celite, rinsing with abundant EtOAc. The resulting solution was concentrated in vacuo to give 12 as a clear colorless oil (320 mg, quant.). To a solution of 12 (340 mg, 0.808 mmol), 2-((4-chloro-3-fluorophenyl)amino)-2- oxoacetic acid 12' (211 mg, 0.970 mmol) and TBTU (337 mg, 1.050 mmol) in CH$_2$Cl$_2$ (13.5 mL) was added DIPEA (0.212 mL, 1.212 mmol). The resulting mixture was stirred at rt overnight. Once the stirring period was complete, the mixture was diluted with EtOAc, washed with water, 1 N aq. HCl, sat. aq. NaHCO$_3$ and brine. The resulting organic layer was dried over Na$_2$SO$_4$ and concentrated in vacuo. Flash column chromatography (SiO$_2$, 7:3 hexanes/EtOAc) afforded (+)-13 as a white solid (392 mg, 78% from (+)-11).

$^1$H NMR (500 MHz, CDCl$_3$) δ 9.44 (s, 1 H), 7.74 (dd, J=10.7 Hz, 2.4 Hz, 1 H), 7.69 (d, J=9.3 Hz, 1 H), 7.38 (t, J=8.3 Hz, 1 H), 7.29-7.26 (m, 1 H), 7.17 (d, J=7.8 Hz, 1 H), 7.09 (br s, 2 H), 5.36 (t, J=8.3 Hz, 1 H), 4.42 (s, 2 H), 3.81 (d, J=5.3 Hz, 2 H), 3.08 (dd, J=16.1 Hz, 8.2 Hz, 1 H), 2.87-2.80 (m, 4 H), 2.59-2.52 (m, 1 H), 1.49 (s, 9 H), 0.88 (s, 9 H), 0.08 (s, 3 H), 0.07 (s, 3 H); $^{13}$C NMR (125 MHz, CDCl$_3$) δ 159.4, 159.2, 157.7, 142.9, 140.6, 138.8, 136.5, 136.4, 131.0, 124.3, 116.1 (d, J$_{CF}$=3.5 Hz), 108.4 (d, J$_{CF}$=26.1 Hz), 63.9, 57.0, 51.1, 34.1, 33.6, 28.6, 26.0, 18.4, −5.3; HRMS (ES+) m/z=642.2553 ([M+Na]$^+$; calcd for C$_{31}$H$_{43}$N$_3$O$_5$SiClFNa: 642.2542); [α]$_D^{22}$ +33.8 (c 0.54, CH$_2$Cl$_2$).

(−)-13: data consistent with (+)-isomer-[α]$_D^{22}$ −31.3 (c 0.20, CH$_2$Cl$_2$)

K. tert-butyl (((1R,2S)-1-(2-((4-chloro-3-fluorophenyl)amino)-2-oxoacetamido)-2-(hydroxymethyl)-2,3-dihydro-1H-inden-5-yl)methyl)(methyl)carbamate (14)

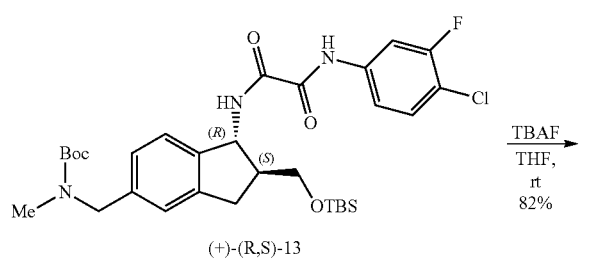

(+)-(R,S)-13

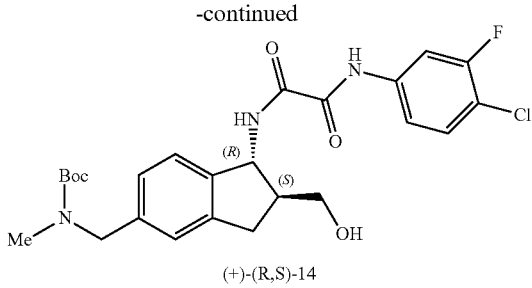

(+)-(R,S)-14

To a solution of (+)-13 (354 mg, 0.571 mmol) in THF (11 mL) at rt was added TBAF (1 M solution in THF, 0.614 mL, 1.14 mmol). The reaction was stirred at rt overnight, then diluted with EtOAc and washed with water and brine. The resulting organic layer was dried over Na$_2$SO$_4$ and concentrated in vacuo. Flash column chromatography (SiO$_2$, 1:1 hexanes/EtOAc) afforded (+)-14 as a white solid (237 mg, 82%).

$^1$H NMR (500 MHz, DMSO-d$_6$) δ 11.06 (s, 1 H), 9.30 (d, J=8.7 Hz, 1 H), 7.96 (d, J=10.9 Hz, 1 H), 7.75 (d, J=8.3 Hz, 1 H), 7.59 (t, J=8.6 Hz, 1 H), 7.12 (d, J=7.1 Hz, 1 H), 7.08 (br. s., 1 H), 7.03 (d, J=7.3 Hz, 1 H), 5.22 (t, J=8.1 Hz, 1 H), 4.70 (t, J=4.8 Hz, 1 H), 4.34 (s, 2 H), 3.61-3.49 (m, 2 H), 3.08-3.00 (m, 1 H), 2.78-2.66 (m, 5 H), 1.42 (br. s., 9 H); $^{13}$C NMR (125 MHz, DMSO-d$_6$) δ 160.4, 159.6, 143.3, 138.2, 131.2, 124.5, 109.1 (d, J$_{CF}$=25.9 Hz), 79.4, 62.5, 56.5, 49.1, 34.0, 28.7; HRMS (ES+) m/z=528.1689 ([M+Na]$^+$; calcd for C$_{25}$H$_{29}$N$_3$O$_5$FClNa: 528.1677); [α]$_D^{22}$ +48.16 (c 0.56, EtOAc).

(−)-14: data consistent with (+)-isomer-[α]$_D^{22}$ −52.9 (c 0.40, CH$_2$Cl$_2$)

L. tetra-Boc BNM-III-170 ((+)-15)

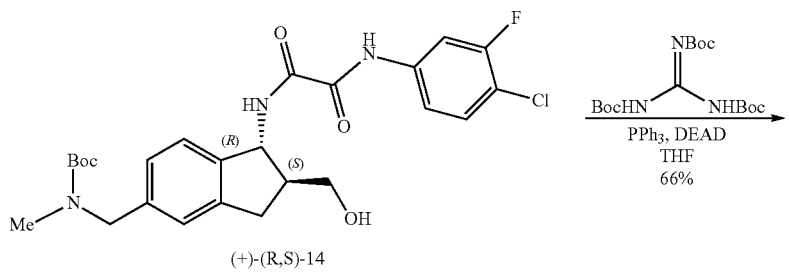

(+)-(R,S)-14

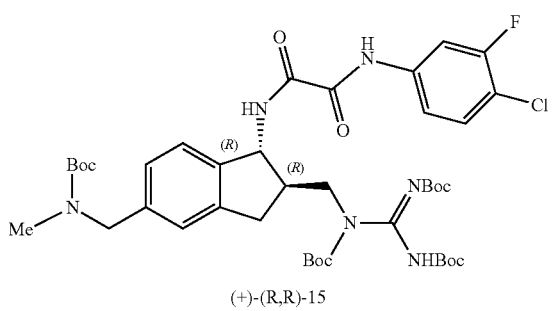

(+)-(R,R)-15

To a solution of (+)-14 (220 mg, 0.435 mmol) in THF (16.5 mL) were added N,N',N"-tri-Boc-guanidine (469 mg, 1.305 mmol) and triphenylphosphine (171 mg, 0.653 mmol). The suspension was cooled to 0° C. and DEAD (0.297 mL, 0.653 mmol) was added dropwise. The reaction vessel was sealed and heated to 80° C. for 90 min under microwave conditions. After cooling to rt, the reaction was quenched by addition of sat. aq. NaHCO$_3$ and extracted with EtOAc. The combined organic layers were washed with brine, dried over Na$_2$SO$_4$ and concentrated in vacuo. Flash column chromatography (SiO$_2$, 10:1 to 2:1 hexanes/EtOAc) afforded (+)-15 as a white foam (248 mg, 66%).

$^1$H NMR (500 MHz, CDCl$_3$) δ 9.32 (s, 1 H), 7.79-7.74 (m, 2 H), 7.39 (t, J=8.5 Hz, 1 H), 7.24-7.22 (m, 1 H), 7.16 (d, J=7.9 Hz, 1 H), 7.08 (br s, 2 H), 5.26 (t, J=8.6 Hz, 1 H), 4.41 (s, 2 H), 4.16-4.11 (m, 4 H), 3.17 (q, J=7.7 Hz, 1 H), 2.90-2.76 (m, 5 H), 1.55-1.47 (m, 36 H); $^{13}$C NMR (125 MHz, CDCl$_3$) δ 159.7, 159.2, 157.5, 153.3, 142.5, 140.3, 138.7, 136.5, 130.9, 124.1, 116.0, 108.4 (d, J$_{CF}$=25.9 Hz), 83.6, 58.5, 50.1, 48.3, 35.1, 34.0, 29.8, 28.6, 28.2, 28.1; HRMS (ES+) m/z=847.3828 ([M+H]$^+$; calcd for C$_{41}$H$_{57}$N$_6$O$_{10}$ClF: 847.3809); [α]$_D^{22}$ +28.2 (c 1.28, CH$_2$Cl$_2$).

(−)-15: data consistent with (+)-isomer-[α]$_D^{22}$ −40.0 (c 0.13, CH$_2$Cl$_2$)

M. BNM-III-170

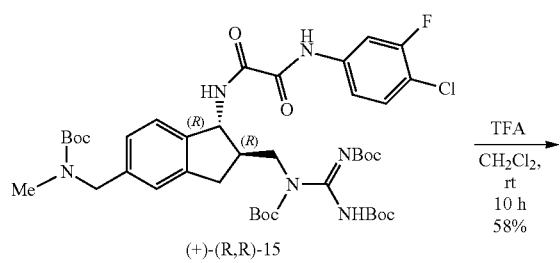

(+)-(R,R)-15

TFA
CH$_2$Cl$_2$,
rt
10 h
58%

•2 CF$_3$COO−

(+)-(R,R)-BNM-III-170

To a solution of (+)-15 (228 mg, 0.269 mmol) in CH$_2$Cl$_2$ (5.4 mL) was added TFA (0.964 mL, 12.374 mmol). The reaction mixture was stirred at rt for 4 h then concentrated in vacuo. The crude residue was taken up in water/acetonitrile (90:10, 4 mL). TFA (1.0 mL) was added. The resulting clear solution was purified by HPLC (3 injections of 1800 μL each, 1 injection of 1300 μL). Eluant: 90:10 to 60:40 water/acetonitrile (12-minute gradient). Flow rate: 15 mL/min. Product retention time: 5-6 min. Product fractions were combined and acetonitrile was removed in vacuo. The resulting aqueous solution was deep-frozen (−78° C. bath) and lyophilized (0.035 mbar) to afford the bis-formate salt (+)-BNM-III-170 as a white powder (106 mg, 58%).

$^1$H NMR (500 MHz, DMSO-d$_6$) δ 11.08 (s, 1 H), 9.47 (d, J=8.9 Hz, 1 H), 8.89 (s, 2 H), 7.98 (dd, J=11.8 Hz, 2.4 Hz, 1 H), 7.83 (t, J=5.5 Hz, 1 H), 7.77 (dd, J=9.0 Hz, 2.0 Hz, 1 H), 7.61 (t, J=8.7 Hz, 1 H), 7.36 (s, 1 H), 7.31-7.21 (m, 3 H), 5.18 (t, J=8.8 Hz, 1 H), 4.11 (s, 2 H), 3.45-3.33 (m, 4 H), 3.12 (dd, J=15.7 Hz, 8.0 Hz, 1 H), 2.91-2.83 (m, 1 H), 2.69 (dd, J=15.5 Hz, 9.2 Hz, 1 H), 2.55 (s, 3 H); $^{13}$C NMR (125 MHz, DMSO-$_6$) δ 160.5, 159.3, 159.0, 158.8, 158.5, 158.3, 157.6, 156.3, 143.9, 142.2, 138.8 (d, J$_{CF}$=10.1 Hz), 132.0, 131.1, 128.9, 126.6, 124.4, 118.9, 117.9 (d, J$_{CP}$=3.0 Hz), 116.5, 115.0, 114.8, 109.0 (d, J$_{CF}$=25.8 Hz), 57.4, 51.7, 45.8, 43.4, 34.3, 32.5; HRMS (ES+) m/z=447.1708 ([M+H]$^+$; calcd for C$_{21}$H$_{25}$N$_6$O$_2$ClF: 447.1712); [α]$_D^{22}$ +26.1 (c 0.15, CH$_3$OH).

(−)-BNM-III-170: data consistent with (+)-isomer-[α]$_D^{22}$ −44.3 (c 0.13, CH$_3$OH).

Example 3

Preparation of BNM-IV-147

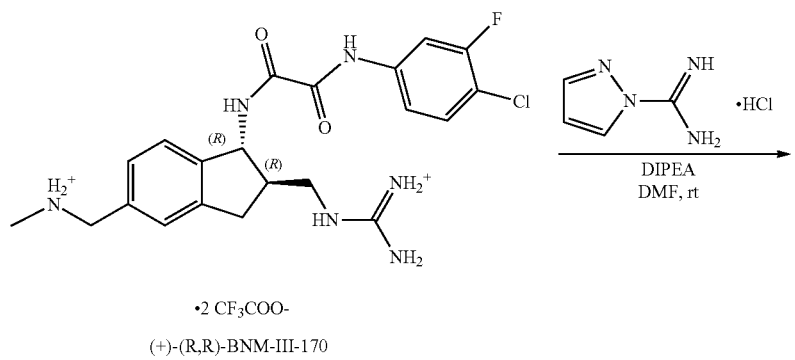

•2 CF$_3$COO−

(+)-(R,R)-BNM-III-170

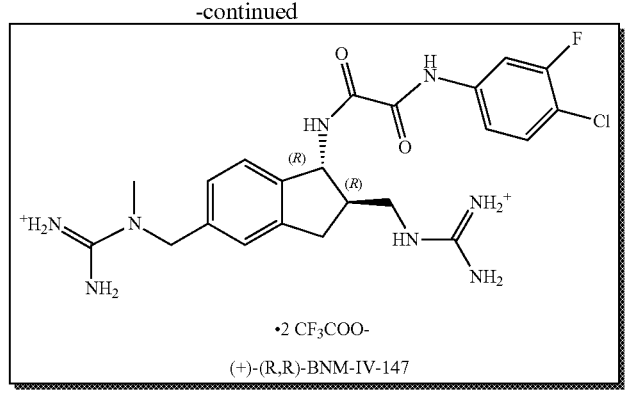

(+)-(R,R)-BNM-IV-147

To a solution of (+)-(R,R)-BNM-III-170.2TFA (40 mg, 0.059 mmol) in DMF (400 µL) at room temperature were added DIPEA (22 µL, 0.124 mmol) and 1H-pyrazole-1-carboximidamide.HCl (18 mg, 0.124 mmol). The resulting mixture was stirred at room temperature for 36 h. Were then added to the reaction vessel water (1.8 mL) and acetonitrile (0.3 mL), and the resulting solution (total volume: 2.5 mL) was submitted to HPLC in a single injection. Eluant: 90:10 to 60:40 water/acetonitrile. Gradient time: 15 min. Flow rate: 15 mL/min. Product retention time: 9.5 min. Product fractions were combined and the resulting solution was deep-frozen (−78° C.) and lyophilized to afford the bis-TFA salt of (+)-(R,R)-BNM-IV-147 as a white powder (35 mg, 82%).

$^1$H NMR (500 MHz, DMSO-d$_6$) δ 11.09 (s, 1 H), 9.45 (d, J=8.7 Hz, 1 H), 7.98 (d, J=11.9 Hz, 1 H), 7.89-7.71 (m, 2 H), 7.61 (t, J=8.6 Hz, 1 H), 7.51 (br. s., 5 H), 7.21-7.11 (m, 3 H), 7.07 (d, J=7.9 Hz, 1 H), 5.17 (t, J=8.5 Hz, 1 H), 4.56 (s, 2 H), 3.61-3.21 (m, 2 H+residual H2O), 3.12 (dd, J=15.9, 7.9 Hz, 1 H), 2.91 (s, 3 H), 2.84 (q, J=6.3 Hz, 1 H), 2.67 (dd, J=15.5 Hz, 8.9, 1 H); $^{13}$C NMR (125 MHz, DMSO-d$_6$) δ 160.0, 158.8, 158.4 (q, J$_{CF}$=32 Hz, TFA), 157.0, 156.8 (d, J$_{CF}$=244 Hz), 156.8, 142.2, 141.9, 138.4 (d, J$_{CF}$=10 Hz), 135.4, 130.7, 125.8, 124.0, 123.5, 117.4 (d, J$_{CF}$=3 Hz), 114.4 (d, J$_{CF}$=18 Hz), 108.5 (d, J$_{CF}$=26 Hz), 56.9, 52.6, 45.3, 42.9, 40.1, 36.1, 33.9; HRMS (ES+) m/z=489.1929 ([M+H]+; calcd for C$_{22}$H$_{27}$N$_8$O$_2$ClF: 489.1930); [α]$_D^{22}$ +11.8 (c 0.16, CH$_3$OH).

Compound BNM-IV-197 was prepared as described above using JP-III-048.

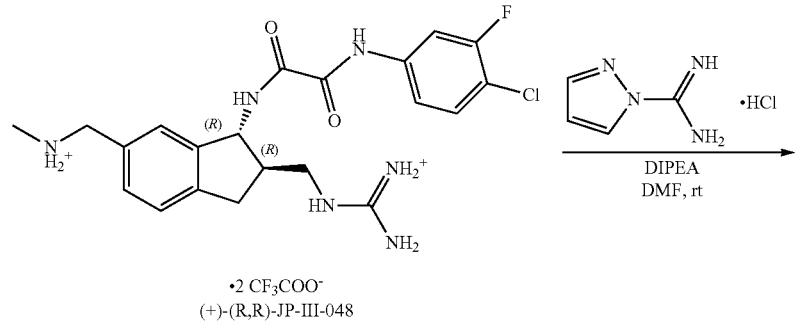

(+)-(R,R)-JP-III-048

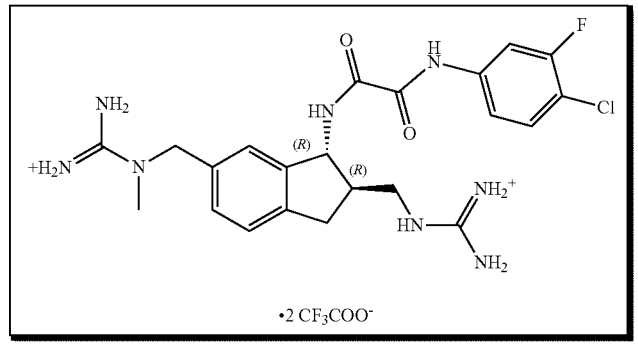

(−)-(R,R)-BNM-IV-197

Example 4

Preparation of (+)-DMJ-II-121.TFA

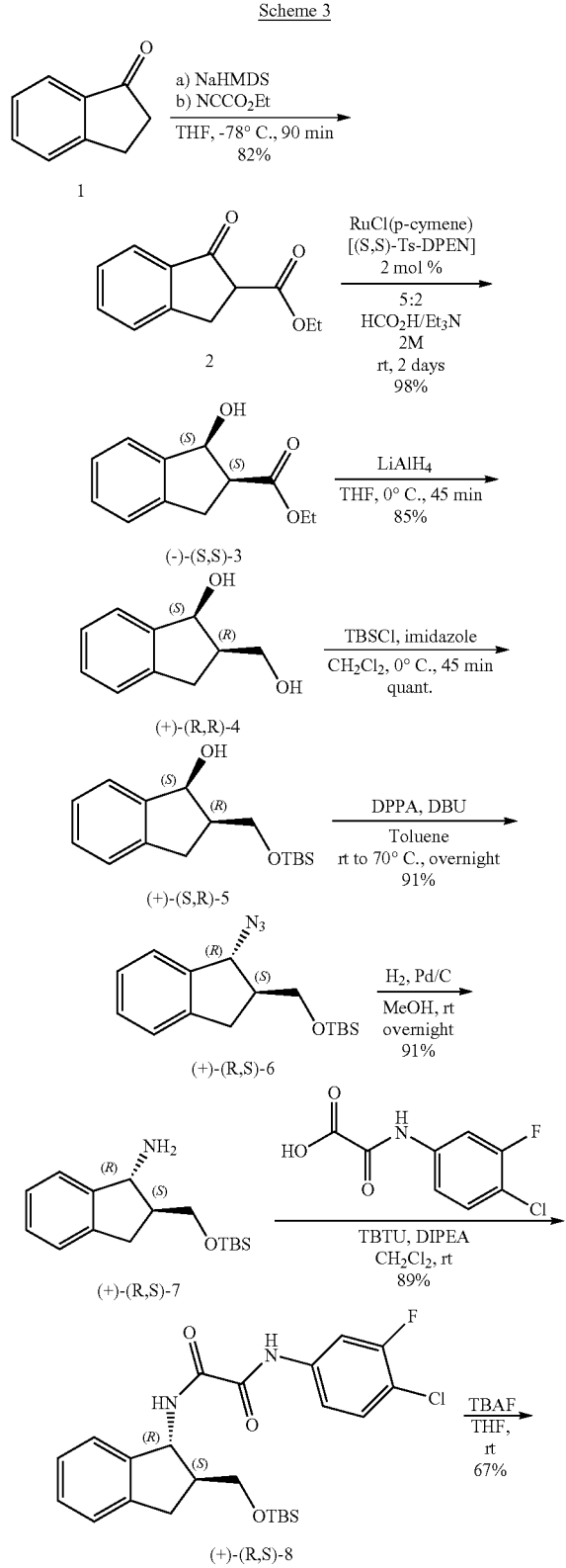

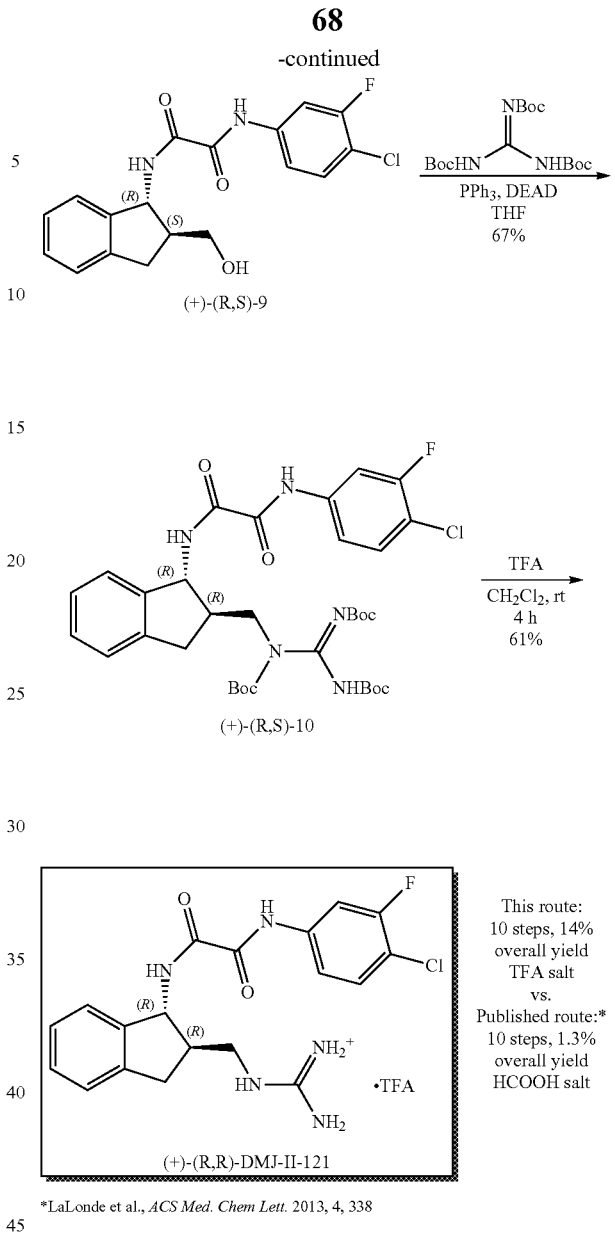

(+)-DMJ-II-121.TFA was prepared according to Scheme 3 and using the procedure outlined in Examples 1 and 2.

$^1$H NMR (500 MHz, DMSO-$d_6$) δ 11.09 (s, 1 H), 9.45 (d, J=8.7 Hz, 1 H), 7.98 (dd, J=11.7, 2.4 Hz, 1 H), 7.77 (dd, J=8.9, 1.6 Hz, 1 H), 7.54-7.66 (m, 2 H), 7.11-7.33 (m, 5 H), 5.20 (t, J=8.7 Hz, 1 H), 3.24-3.55 (m, 2 H), 3.12 (dd, J=15.7, 7.9 Hz, 1 H), 2.75-2.94 (m, 1 H), 2.67 (dd, J=15.6, 9.0 Hz, 1 H); $^{13}$C NMR (125 MHz, DMSO-$d_6$) δ 160.6, 158.7, 158.5 (d, $J_{CF}$=241 Hz), 156.5, 143.0, 141.7, 139.0 (d, $J_{CF}$=10 Hz), 131.2, 130.8, 128.4, 127.3, 125.3, 124.2, 118.0 (d, $J_{CF}$=3 Hz), 115.0 (d, $J_{CF}$=18 Hz), 109.0 (d, $J_{CF}$=26 Hz), 57.7, 45.8, 43.5, 34.5; HRMS (ES+) m/z=404.1290 ([M+H]$^+$; calcd for $C_{19}H_{20}N_5O_2ClF$: 404.1295); $[α]_D^{22}$ +22.7 (c 0.1, $CH_3OH$).

(−)-DMJ-II-121.TFA: data consistent with (+)-isomer-$[α]_D^{22}$ −43.6 (c 0.1, $CH_3OH$).

Example 5

Preparation of (+)-BNM-IV-125

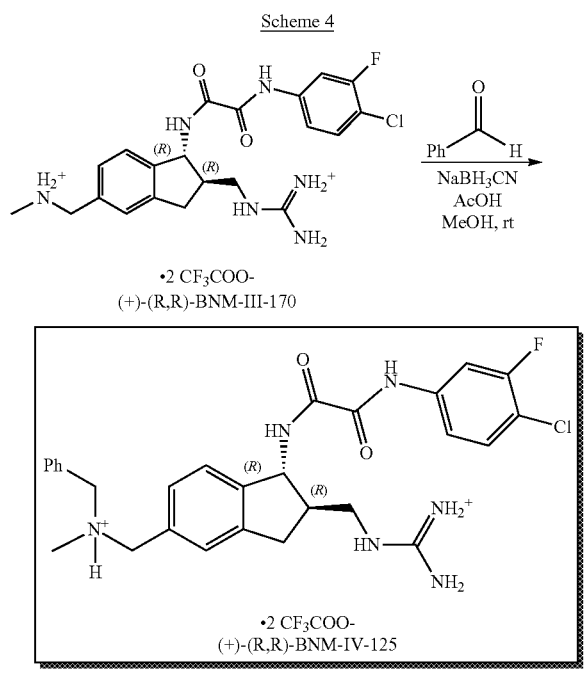

Scheme 4

•2 CF₃COO⁻
(+)-(R,R)-BNM-III-170

•2 CF₃COO⁻
(+)-(R,R)-BNM-IV-125

To a solution of (+)-(R,R)-BNM-III-170.2TFA (15 mg, 0.022 mmol) in MeOH (1.1 mL) at rt were added benzaldehyde (23 µL, 0.22 mmol) and acetic acid (1.5 µL, 0.027 mmol). The resulting mixture was stirred at rt for 10 min. Sodium cyanoborohydride (1.7 mg, 0.027 mmol) was then added and the resulting mixture was stirred at rt overnight. The reaction mixture was then concentrated under a stream of nitrogen. Water (1.3 mL), CH₃CN (0.2 mL) and TFA (0.1 mL) were added and the resulting mixture was purified by HPLC in a single injection. Eluant: 90:10 to 40:60 water/acetonitrile. Gradient time: 20 min. Flow rate: 15 mL/min. Product retention time: 10.7 min. Product fractions were combined and the resulting solution was deep-frozen (−78° C.) and lyophilized (0.08 mbar) to afford the bis-TFA salt of (+)-(R,R)-BNM-IV-125 as a white powder (14 mg, 82%).

$^1$H NMR (500 MHz, DMSO-$d_6$) δ 11.11 (s, 1 H), 10.13 (br. s., 1 H), 9.49 (d, J=8.5 Hz, 1 H), 7.99 (dd, J=11.9, 2.4 Hz, 1 H), 7.85 (t, J=5.4 Hz, 1 H), 7.77 (dd, J=8.9, 1.6 Hz, 1 H), 7.61 (t, J=8.7 Hz, 1 H), 7.45-7.55 (m, 6 H), 7.41 (s, 1 H), 7.36 (d, J=7.7 Hz, 1 H), 7.25 (d, J=7.9 Hz, 1 H), 5.20 (t, J=8.7 Hz, 1 H), 4.45 (d, J=12.1 Hz, 2 H), 4.21 (br. s., 2 H), 3.27-3.50 (m, 2 H), 3.13 (dt, J=15.1, 7.3 Hz, 1 H), 2.80-2.93 (m, 1 H), 2.66-2.77 (m, 1 H), 2.53 (br. s., 3 H); $^{13}$C NMR (125 MHz, DMSO-$d_6$) δ 160.1, 158.9, 158.3 (q, $J_{CF}$=32 Hz, TFA), 157.0, 156.8 (d, $J_{CF}$=244 Hz), 144.2, 141.9, 138.3 (d, $J_{CF}$=10 Hz), 131.3, 130.6, 129.8, 129.6, 129.4, 128.9, 127.5, 123.9, 117.3 (d, $J_{CF}$=3 Hz), 114.4 (d, $J_{CF}$=18 Hz), 108.5 (d, $J_{CF}$=26 Hz), 58.6, 56.9, 45.3, 42.9, 37.9, 33.8; HRMS (ES+) m/z=537.2183 ([M+H]⁺; calcd for $C_{28}H_{31}N_6O_2ClF$: 537.2181); $[\alpha]_D^{22}$ +11.3 (c 0.13, CH₃OH).

Example 6

Additional Compounds Prepared by Reductive Amination

The following compounds were prepared as outlined in Scheme 5 and using the reduction amination synthetic procedure of Example 5.

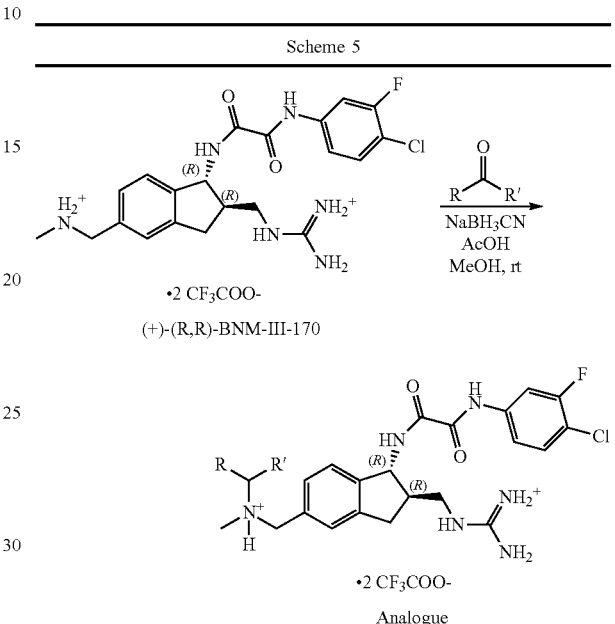

Scheme 5

•2 CF₃COO⁻
(+)-(R,R)-BNM-III-170

•2 CF₃COO⁻
Analogue

| Analogue | R | R' |
|---|---|---|
| BNM-IV-114 | Me | H |
| BNM-IV-117 | Me | Me |
| BNM-IV-123 | Et | H |
| BNM-IV-124 | i-Pr | H |
| BNM-IV-139 | Bn | H |
| BNM-IV-137 | COON | H |

Example 7

Biological Procedures

Compounds: Compounds are dissolved in dimethyl sulfoxide at a stock concentration of 10 mM, aliquoted, and stored at −20° C. Each compound is then diluted to 1 mM in serum-free Dulbecco's modified Eagle medium (DMEM) and used for different assays.

Cell Lines: 293T human embryonic kidney and Cf2Th canine thymocytes (ATCC) are grown at 37° C. and 5% $CO_2$ in Dulbecco's modified Eagle's medium (Invitrogen) containing 10% fetal bovine serum (Sigma) and 100 µg/mL penicillin-streptomycin (Mediatech, Inc.). Cf2Th cells stably expressing human CCR5 and CD4 are grown in medium supplemented with 0.4 mg/mL G418 and 0.2 mg/mL hygromycin (Invitrogen).

Recombinant Luciferase Viruses: 293T human embryonic kidney cells were co-transfected with plasmids expressing the pCMVΔP1Δenv HIV-1 Gag-Pol packaging construct, the R5 YU2 envelope glycoproteins, or the envelope glycoprotein of the control amphotropic murine leukemia virus (A-MLV), and the firefly luciferase-expressing vector at a DNA ratio of 1:1:3 µg using the Effectene transfection reagent (Qiagen). Co-transfection produced single-round, replication-defective viruses. The virus-containing supernatants were harvested 36-40 h after transfection, spun, aliquoted, and frozen at −80° C. until further use. The reverse transcriptase (RT) activities of all viruses were measured as described in Rho, H. M., et al. *Virology* 1981, 112, 355-360.

Infection by Single-Round Luciferase Viruses. Cf2Th-CCR5-CD4 target cells were seeded at a density of 6×10$^3$ cells/well in 96-well luminometer-compatible tissue culture plates (PerkinElmer) 24 h before infection. On the day of infection, CD4-mimetic compounds of interest (0-100 μM) were incubated with recombinant viruses (10,000 RT units) at 37° C. for 30 min. In the case of sensitization assays, a constant concentration of compounds was incubated with virus for 30 min at 37° C.; then, 17b or other antibodies (0-100 μg/mL) were added to the virus/compound mixture and incubated for an additional 30 min at 37° C. The mixtures were then added to the target cells and incubated for 48 h at 37° C.; after this time, the medium was removed from each well, and the cells were lysed by the addition of 30 μL passive lysis buffer (Promega) and three freeze-thaw cycles. An EG&G Berthold Microplate Luminometer LB 96V was used to measure the luciferase activity of each well after the addition of 100 μL of luciferin buffer (15 mM MgSO$_4$, 15 mM KPO$_4$, pH 7.8, 1 mM ATP, and 1 mM dithiothreitol) and 50 μL of 1 mM Firefly D-Luciferin Free Acid 99% (Prolume).

TABLE 1

| Compound | JR-FL (μM) | YU-2 (μM) | AD8 (μM) | A-MLV (μM) |
|---|---|---|---|---|
| (+)-DMJ-II-121 | 66.8 ± 9.5 | 3.8 ± 1.3 | 8.5 ± 2.1 | 94.3 ± 5.7 |
| (+)-JP-III-048 | 37.3 ± 13.8 | 2.1 ± 0.9 | 6.7 ± 0.6 | >100 |
| (−)-JP-III-048 | >100 | 87.8 ± 12.2 | >100 | >100 |
| (+)-BNM-III-170 | 14.2 ± 4.5 | 1.5 ± 0.8 | 6.4 ± 1.0 | >100 |
| (−)-BNM-III-170 | >100 | 21 | — | >100 |
| BNM-IV-114 | 10.0 ± 4.0 | — | — | >100 |
| BNM-IV-117 | 12.5 ± 2.0 | — | — | >100 |
| BNM-IV-123 | 8.0 ± 4.0 | — | — | >100 |
| BNM-IV-124 | 11.0 ± 3.0 | — | — | >100 |
| (+)-BNM-IV-125 | 14.0 ± 2.0 | — | — | >100 |
| BNM-IV-137 | 32.2 ± 6.4 | 2.2 ± 0.4 | 7.1 ± 1.0 | >100 |
| BNM-IV-139 | 17.1 ± 2.3 | 5.2 ± 0.5 | 15.3 ± 0.6 | >100 |
| (+)-BNM-IV-147 | 6.2 ± 0.5 | 0.8 ± 0.02 | 3.3 ± 0.2 | >100 |
| (−)-BNM-IV-197 | 19.5 ± 10.1 | 1.2 ± 0.3 | 1.3 ± 0.2 | 83.7 ± 16.4 |

Isothermal Titration Calorimetry. Thermodynamic parameters for the binding of the different inhibitors to gp120 were obtained by isothermal titration calorimetry (ITC) using a VP-ITC microcalorimeter from MicroCal/GE Healthcare (Northampton, Mass., USA). The titrations were performed at 25° C. by injecting 10 μL aliquots of inhibitor solution into the calorimetric cell (volume ~1.4 mL) containing monomeric YU-2 gp120 at a concentration of 2 μM. The inhibitor concentration in the syringe was 40-60 μM except for NBD-556, which was prepared at a concentration of 125 μM. In all titration experiments, gp120 and the different inhibitors were equilibrated with PBS, pH 7.4, with 2% DMSO. The heat evolved upon each injection of inhibitor was obtained by integration of the calorimetric signal. The heat associated with inhibitor binding to gp120 was obtained by subtracting the heat of dilution from the heat of reaction. The enthalpy change (ΔH) and association constant ($K_a = 1/K_d$) were obtained by nonlinear regression of the data and are shown in Table 2.

TABLE 2

| Compound | $K_D$ (μM) | ΔG (kcal/mol) | ΔH (kcal/mol) | −TΔS (kcal/mol) |
|---|---|---|---|---|
| (+)-DMJ-II-121 | 0.11 | −9.5 | −17.9 | +8.4 |
| (+)-JP-III-048 | 0.024 | −10.4 | −28.2 | +17.8 |
| (−)-JP-III-048 | 3.4 | −7.5 | −11.3 | +3.8 |
| (+)-BNM-III-170 | 0.047 | −10.0 | −20.7 | +10.7 |
| (−)-BNM-III-170 | 1.2 | −8.1 | −13.2 | +5.1 |
| (+)-BNM-IV-147 | 0.095 | −9.6 | −15.4 | +5.8 |
| (−)-BNM-IV-197 | 0.095 | −9.6 | −14.2 | +4.6 |

Assessment of the Maximum Tolerated Dose (MTD)

Procedure: (+)-BNM-III-170 was dissolved in DMSO to a final concentration of 10 mg/mL. This solution was then used for intraperitoneal administration to CD-1 mice at various doses to examine for visible signs of intolerance after compound dosing. This included an assessment of hyper- or hypoactivity, altered locomotion, ataxia, sedation, or other visible abnormalities. The compound was ultimately tested at three doses (30 mg/kg, 10 mg/kg and 3 mg/kg), as outlined below, with the amounts injected per mouse and the behavioral observations indicated for each dosing group.

Results:

a) 10 mg/kg (5-month old CD-1 female mice)

| Mouse ID | Weight (g) | Vol. injected (μL) |
|---|---|---|
| CD-1 | 43.4 | 43.4 |
| CD-2 | 51.3 | 51.3 |
| CD-3 | 43.3 | 43.3 |

Observations: The mice were asleep and quiet for the first 2 hours after dosing, and then resumed normal activities thereafter. This suggested a possible sedative effect, and a higher dose was subsequently examined.

b) 30 mg/kg (5-month old CD-1 female mice)

| Mouse ID | Weight (g) | Vol. injected (μL) |
|---|---|---|
| CD-1 | 47.3 | 141.9 |
| CD-3 | 41.1 | 123.3 |

Observations: The mice were asleep and quiet for over 6 hours, and resumed normal activities by the following morning. This confirmed the observations from the 10 mg/kg dosing, and suggested the compound had a sedative effect. A lower dose was subsequently investigated.

c) 3 mg/kg (2-month old CD-1 female mice)

| Mouse ID | Weight (g) | Vol. injected (μL) |
|---|---|---|
| CD-1 | 22.8 | 22.8 |
| CD-2 | 22.6 | 22.6 |

Observations: The mice behaved normally after compound dosing, with no signs of sedation or altered activity.

Conclusions: Based on the observations described above, (+)-BNM-III-170 appears to induce sedation in CD1 mice at doses of 10 mg/kg or higher, whereas no sedation was observed at 3 mg/kg. Thus, a maximum tolerated dose may be about 3 to about 9 mg/kg.

Evaluation of Blood-Brain Barrier

Compound BNM-III-170 was administered to mice under a protocol approved by the University of Pennsylvania Institutional Animal Care and Use Committee. Specifically, BNM-III-170, dissolved in DMSO, was administered IP at 5 mg/kg to 3 month old female CD1 mice. Mice were euthanized 1 hour post dose. Brain and plasma were then collected.

Hemi-brains were homogenized with 10 mM ammonium acetate pH 4.0 (50% w/v) using a sonic dismembrator. Brain homogenate and plasma were extracted with 4 parts (v/v) acetonitrile, vortexed, and centrifuged at 15,000 g for 10 minutes. Supernatants were analyzed by LC-MS/MS using a Waters Acuity UPLC-TQMS. Samples (5 µL) were separated using a BEH C18 column (1.7 µm, 2.1×50 mm) at 0.6 mL/min from 5 to 95% acetonitrile with 0.1% formic acid over 2 minutes. BNM-III-170 was detected in positive ion mode using selected reaction monitoring of a specific collision induced ion transition (447.3>184.1 m/z). Unknown peak areas were quantified against standard curves constructed with BNM-III-170 spiked mouse brain homogenate or plasma extracted as above to final concentrations from 1 to 1000 ng/mL.

Concentrations 1 hr Post IP at 5 mg/kg

| Mouse | Brain ng/g | Plasma ng/mL | B/P |
| --- | --- | --- | --- |
| 1 | 268 | 522 | 0.51 |
| 2 | 131 | 910 | 0.14 |
| 3 | 122 | 270 | 0.45 |
| AVG | 174 | 567 | 0.37 |
| SD | 82 | 322 | 0.20 |
| % RSD | 47 | 57 | 54 |

The contents of all references, patent applications, patents, and published patent applications, as well as the Figures, cited throughout this application are hereby incorporated by reference.

Those skilled in the art will recognize, or be able to ascertain using no more than routine experimentation, many equivalents to the specific embodiments of the disclosure described herein. Such equivalents are intended to be encompassed by the following claims.

We claim:

1. A compound of Formula I

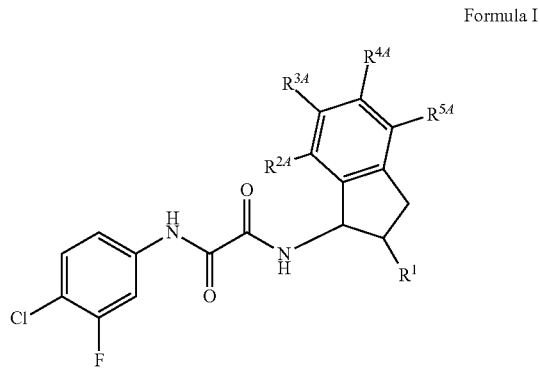

Formula I or a salt or solvate thereof, wherein, $R^1$ is

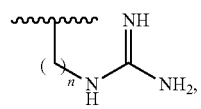

wherein n is 1;

$R^{2A}$ is H, optionally substituted alkylaminoalkyl, optionally substituted cycloalkylaminoalkyl, or

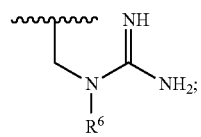

$R^{3A}$ is H, optionally substituted alkylaminoalkyl, optionally substituted cycloalkylaminoalkyl, or

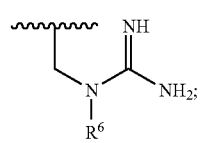

$R^{4A}$ is H, optionally substituted alkylaminoalkyl, optionally substituted cycloalkylaminoalkyl, or

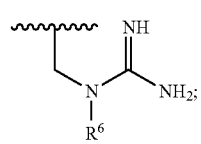

$R^{5A}$ is H, optionally substituted alkylaminoalkyl, optionally substituted cycloalkylaminoalkyl, or

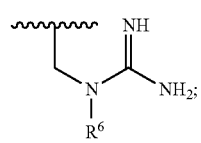

wherein $R^6$ is H, $C_{1-6}$alkyl, or $C_{3-8}$cycloalkyl;

provided at least one of $R^{2a}$, $R^{3A}$, $R^{4A}$, or $R^{5A}$ is optionally substituted alkylaminoalkyl, optionally substituted cycloalkylaminoalkyl, or

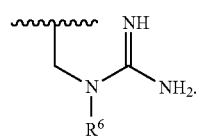

2. The compound of claim 1, wherein $R^{3A}$ is H.

3. The compound of claim 1, wherein $R^{3A}$ is methylaminoalkyl, ethylaminoalkyl, or propylaminoalkyl.

4. The compound of claim 1, wherein $R^{3A}$ is alkylamino-$CH_2$—.

5. The compound of claim 1, wherein $R^{3A}$ is $CH_3$—NH—$CH_2$— or $(CH_3)_2CH$—NH—$CH_2$—.

6. The compound of claim 1, wherein $R^{3A}$ is cyclopropylaminoalkyl, cyclobutylaminoalkyl, cyclopentylaminoalkyl, or cyclohexylaminoalkyl.

7. The compound of claim 1, wherein $R^{3A}$ is cyclopropylamino-$CH_2$—, cyclobutylamino-$CH_2$—, cyclopentylamino-$CH_2$—, or cyclohexylamino-$CH_2$—.

8. The compound of claim 1, wherein $R^{3A}$ is

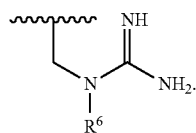

9. The compound of claim 1, wherein $R^6$ is H, methyl, ethyl, isopropyl, or cyclopropyl.

10. The compound of claim 1, wherein $R^{2A}$, $R^{4A}$, and $R^{5A}$ are H.

11. The compound of claim 1, wherein $R^{4A}$ is H.

12. The compound of claim 1, wherein $R^{4A}$ is methylaminoalkyl, ethylaminoalkyl, or propylaminoalkyl.

13. The compound of claim 1, wherein $R^{4A}$ is optionally substituted alkylamino-$CH_2$—.

14. The compound of claim 13, wherein $R^{4A}$ is $CH_3$—NH—$CH_2$—, $(CH_3)_2CH$—NH—$CH_2$—, $CH_3$—N($CH_2$-phenyl)-$CH_2$—, $CH_3$—N(—$CH_2CH_2$-phenyl)-$CH_2$— or $CH_3$—N($CH_2COOH$)—$CH_2$—.

15. The compound of claim 1, wherein $R^{4A}$ is cyclopropylaminoalkyl, cyclobutylaminoalkyl, cyclopentylaminoalkyl, or cyclohexylaminoalkyl.

16. The compound of claim 1, wherein $R^{4A}$ is cyclopropylamino-$CH_2$—, cyclobutylamino-$CH_2$—, cyclopentylamino-$CH_2$—, or cyclohexylamino-$CH_2$—.

17. The compound of claim 1, wherein $R^{4A}$ is

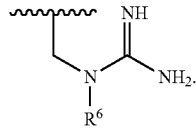

18. The compound of claim 17, wherein $R^6$ is H, methyl, ethyl, isopropyl, or cyclopropyl.

19. The compound of claim 1, wherein $R^{2A}$, $R^{3A}$, and $R^{5A}$ are H.

20. The compound of claim 1, wherein the compound is

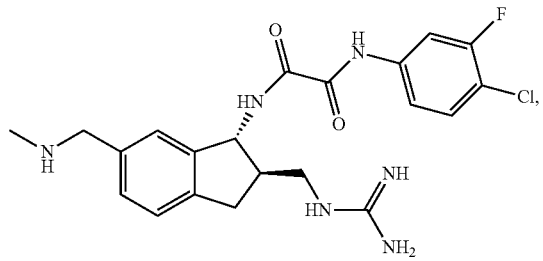

(+)-(R,R)-JP-III-048

-continued

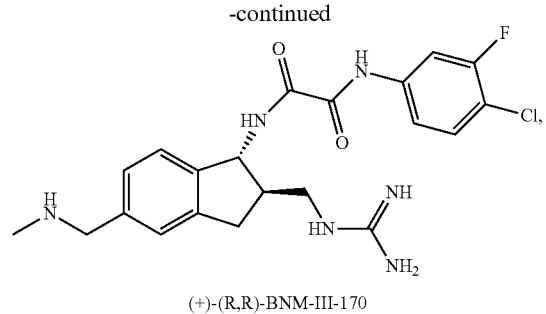

(+)-(R,R)-BNM-III-170

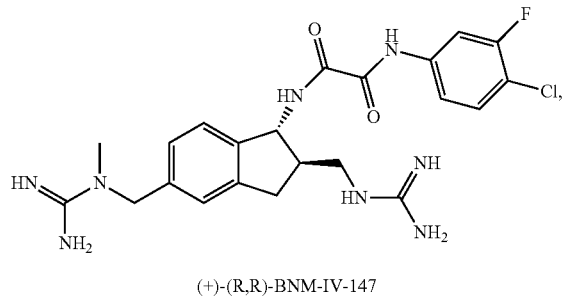

(+)-(R,R)-BNM-IV-147

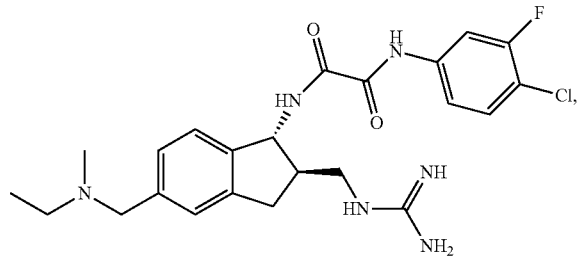

(R,R)-BNM-IV-114

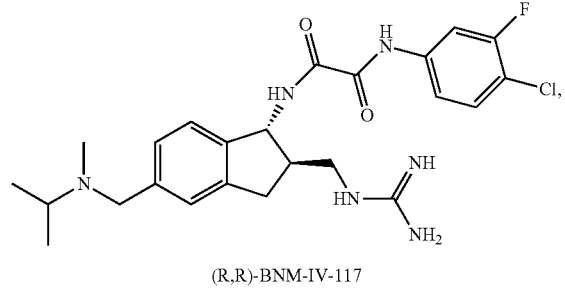

(R,R)-BNM-IV-117

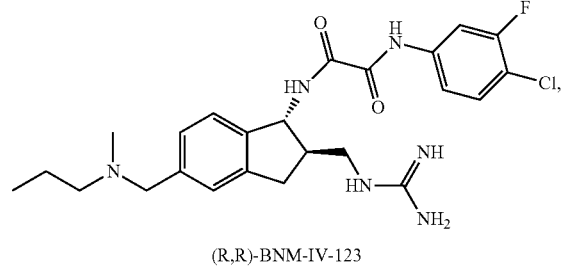

(R,R)-BNM-IV-123

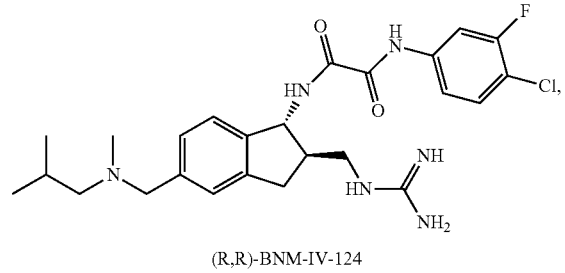

(R,R)-BNM-IV-124

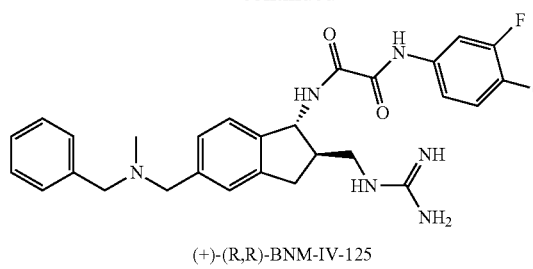

(+)-(R,R)-BNM-IV-125

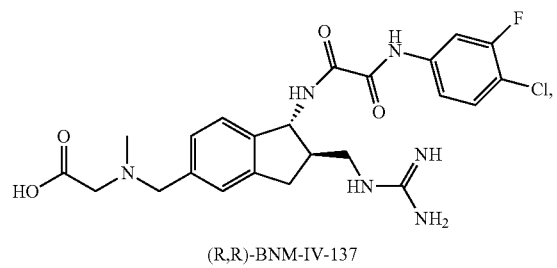

(R,R)-BNM-IV-137

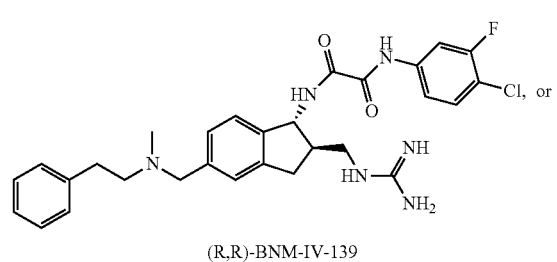

(R,R)-BNM-IV-139

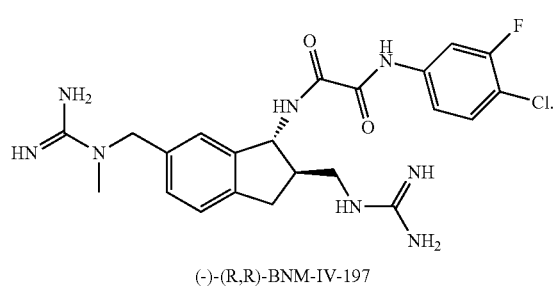

(-)-(R,R)-BNM-IV-197

21. The compound of claim 1, wherein the compound is a single stereoisomer.

22. The compound of claim 1, wherein the compound is the (R,R) stereoisomer.

23. A complex comprising (i) a compound of claim 1, (ii) gp120 in a functional conformational state, and (iii) optionally, an antibody.

24. The compound of claim 1, wherein the compound is:

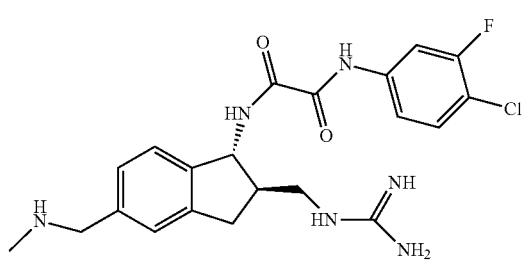 [SMILES: CNCc1ccc2c(c1)C[C@H](CNC(=N)N)[C@H]2NC(=O)C(=O)Nc1ccc(Cl)c(F)c1]

or a salt thereof.

25. The compound of claim 24, wherein the compound is:

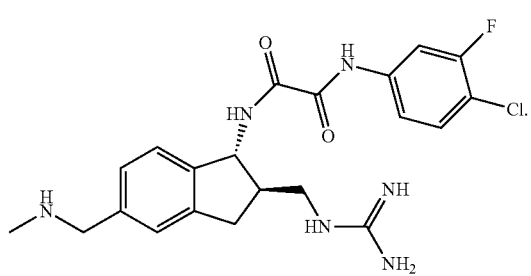 [SMILES: CNCc1ccc2c(c1)C[C@H](CNC(=N)N)[C@H]2NC(=O)C(=O)Nc1ccc(Cl)c(F)c1]

26. The compound of claim 24, wherein the compound is a salt of the compound that is:

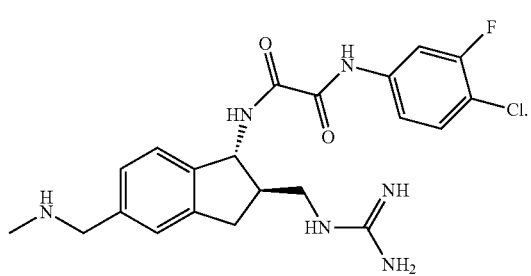 [SMILES: CNCc1ccc2c(c1)C[C@H](CNC(=N)N)[C@H]2NC(=O)C(=O)Nc1ccc(Cl)c(F)c1]

27. The compound of claim 24, that is:

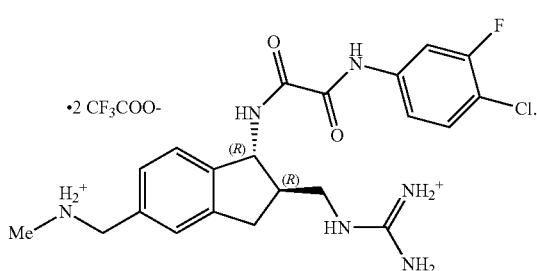

* * * * *

UNITED STATES PATENT AND TRADEMARK OFFICE
CERTIFICATE OF CORRECTION

PATENT NO. : 9,975,848 B2
APPLICATION NO. : 15/503207
DATED : May 22, 2018
INVENTOR(S) : Amos B. Smith, III et al.

Page 1 of 1

It is certified that error appears in the above-identified patent and that said Letters Patent is hereby corrected as shown below:

In the Claims

Claim 9, Column 75, at Line 21, delete "claim 1," and insert -- claim 8, --.

Signed and Sealed this
Second Day of April, 2019

Andrei Iancu
*Director of the United States Patent and Trademark Office*